(12) United States Patent
Molina

(10) Patent No.: US 11,491,149 B2
(45) Date of Patent: *Nov. 8, 2022

(54) ANTI-ANDROGENS FOR THE TREATMENT OF NON-METASTATIC CASTRATION-RESISTANT PROSTATE CANCER

(71) Applicant: Aragon Pharmaceuticals, Inc., San Diego, CA (US)

(72) Inventor: Arturo Molina, Los Altos Hills, CA (US)

(73) Assignee: Aragon Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/885,767

(22) Filed: May 28, 2020

(65) Prior Publication Data

US 2020/0352926 A1 Nov. 12, 2020
US 2022/0054468 A9 Feb. 24, 2022

Related U.S. Application Data

(63) Continuation of application No. 15/967,452, filed on Apr. 30, 2018, now Pat. No. 10,702,508.

(60) Provisional application No. 62/630,594, filed on Feb. 14, 2018, provisional application No. 62/617,745, filed on Jan. 16, 2018, provisional application No. 62/572,791, filed on Oct. 16, 2017.

(51) Int. Cl.
| | |
|---|---|
| A61K 31/4439 | (2006.01) |
| A61P 35/00 | (2006.01) |
| A61K 31/4166 | (2006.01) |
| A61K 31/4178 | (2006.01) |
| A61K 31/192 | (2006.01) |
| A61K 31/4365 | (2006.01) |
| A61K 31/496 | (2006.01) |
| A61K 31/427 | (2006.01) |
| A61K 9/00 | (2006.01) |
| A61K 31/4152 | (2006.01) |
| A61K 31/4155 | (2006.01) |
| A61K 31/426 | (2006.01) |
| A61K 31/00 | (2006.01) |
| G06Q 30/06 | (2012.01) |

(52) U.S. Cl.
CPC ........ *A61K 31/4439* (2013.01); *A61K 9/0053* (2013.01); *A61K 31/00* (2013.01); *A61K 31/192* (2013.01); *A61K 31/4152* (2013.01); *A61K 31/4155* (2013.01); *A61K 31/4166* (2013.01); *A61K 31/4178* (2013.01); *A61K 31/426* (2013.01); *A61K 31/427* (2013.01); *A61K 31/4365* (2013.01); *A61K 31/496* (2013.01); *A61P 35/00* (2018.01); *G06Q 30/0607* (2013.01)

(58) Field of Classification Search
CPC .... A61K 31/496; A61K 31/4439; A61P 35/00
See application file for complete search history.

(56) References Cited

U.S. PATENT DOCUMENTS

| | | |
|---|---|---|
| 3,823,240 A | 7/1974 | Sauli |
| 3,984,430 A | 10/1976 | Curran |
| 4,097,578 A | 6/1978 | Perronnet et al. |
| 4,229,447 A | 10/1980 | Porter |
| 4,234,736 A | 11/1980 | Bernauer et al. |
| 4,304,782 A | 12/1981 | Dumont et al. |
| 4,312,881 A | 1/1982 | Wootton |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,596,795 A | 6/1986 | Pitha |
| 4,608,392 A | 8/1986 | Jacquet et al. |
| 4,749,403 A | 6/1988 | Liebl et al. |
| 4,755,386 A | 7/1988 | Hsiao et al. |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schroeder et al. |
| 4,992,478 A | 2/1991 | Geria |
| 5,010,182 A | 4/1991 | Brake et al. |
| 5,011,692 A | 4/1991 | Fujioka et al. |

(Continued)

FOREIGN PATENT DOCUMENTS

| | | |
|---|---|---|
| AU | 0217893 | 6/1958 |
| AU | 217893 | 6/1958 |

(Continued)

OTHER PUBLICATIONS

Gomella, Effective Testosterone Suppression for Prostate Cancer: Is There a Best Castration Therapy?, Reviews in Urology, vol. 11, No. 2, pp. 52-60 (2009).*

(Continued)

*Primary Examiner* — Kevin E Weddington
(74) *Attorney, Agent, or Firm* — BakerHostetler

(57) ABSTRACT

Described herein are methods of treating non-metastatic castrate-resistant prostate cancer using an approved drug product comprising apalutamide, enzalutamide or darolutamide. Also described here are drug products containing apalutamide enzalutamide or darolutamide, and methods of selling or offering for sale an anti-androgen drug product.

10 Claims, 7 Drawing Sheets

(56) References Cited

U.S. PATENT DOCUMENTS

| | | |
|---|---|---|
| 5,017,381 A | 5/1991 | Maruyama et al. |
| 5,033,252 A | 7/1991 | Carter |
| 5,052,558 A | 10/1991 | Carter |
| 5,069,711 A | 12/1991 | Fischer et al. |
| 5,071,773 A | 12/1991 | Evans et al. |
| 5,166,358 A | 11/1992 | Seuron et al. |
| 5,229,135 A | 7/1993 | Philippon et al. |
| 5,323,907 A | 6/1994 | Kalvelage |
| 5,411,981 A | 5/1995 | Gaillard-Kelly et al. |
| 5,434,176 A | 7/1995 | Claussner et al. |
| 5,554,607 A | 9/1996 | Elokdah et al. |
| 5,556,983 A | 9/1996 | Claussner et al. |
| 5,589,497 A | 12/1996 | Claussner et al. |
| 5,614,620 A | 3/1997 | Liao et al. |
| 5,627,201 A | 5/1997 | Gaillard-Kelly et al. |
| 5,646,172 A | 7/1997 | Claussner et al. |
| 5,656,651 A | 8/1997 | Sovak et al. |
| 5,705,654 A | 1/1998 | Claussner et al. |
| 5,726,061 A | 3/1998 | Robbins et al. |
| 5,738,685 A | 4/1998 | Halm et al. |
| 5,739,136 A | 4/1998 | Ellinwood et al. |
| 5,750,553 A | 5/1998 | Claussner et al. |
| 5,783,707 A | 7/1998 | Elokdah et al. |
| RE35,956 E | 11/1998 | Gaillard-Kelly et al. |
| 5,837,284 A | 11/1998 | Mehta et al. |
| 5,840,329 A | 11/1998 | Bai |
| 5,958,936 A | 9/1999 | Claussner et al. |
| 5,968,875 A | 10/1999 | Bis et al. |
| 5,985,868 A | 11/1999 | Gray |
| 6,107,488 A | 8/2000 | Bouchet et al. |
| 6,172,076 B1 | 1/2001 | Embrey et al. |
| 6,235,910 B1 | 5/2001 | Beller et al. |
| 6,242,611 B1 | 6/2001 | Claussner et al. |
| 6,307,030 B1 | 10/2001 | French et al. |
| 6,350,763 B1 | 2/2002 | Kelly et al. |
| 6,472,415 B1 | 10/2002 | Sovak et al. |
| 6,479,063 B2 | 11/2002 | Weisman et al. |
| 6,489,163 B1 | 12/2002 | Roy et al. |
| 6,506,607 B1 | 1/2003 | Shyjan |
| 6,710,037 B2 | 3/2004 | Wang et al. |
| 6,828,471 B2 | 12/2004 | Sawyers et al. |
| 7,271,188 B2 | 9/2007 | Tachibana et al. |
| 7,709,517 B2 | 5/2010 | Sawyers et al. |
| 8,183,274 B2 | 5/2012 | Sawyers et al. |
| 8,445,507 B2 | 5/2013 | Jung et al. |
| 8,461,343 B2 | 6/2013 | Ouerfelli et al. |
| 8,470,829 B2 | 6/2013 | Tachibana et al. |
| 8,802,689 B2 | 8/2014 | Jung et al. |
| 8,987,452 B2 | 3/2015 | Ouerfelli et al. |
| 9,108,944 B2 | 8/2015 | Smith et al. |
| 9,126,941 B2 | 9/2015 | Sawyers et al. |
| 9,289,436 B2 | 3/2016 | Szmulewitz et al. |
| 9,340,524 B2 | 5/2016 | Chen et al. |
| 9,388,159 B2 | 7/2016 | Jung et al. |
| 9,481,664 B2 | 11/2016 | Smith et al. |
| 9,512,103 B2 | 12/2016 | Ouerfelli et al. |
| 9,675,586 B2 | 6/2017 | Chow et al. |
| 9,884,054 B2 | 2/2018 | Chen |
| 9,987,261 B2 | 6/2018 | Jung et al. |
| 10,052,314 B2 * | 8/2018 | Chen ................. A61K 31/4166 |
| 10,537,586 B2 | 1/2020 | Altschul et al. |
| 10,695,398 B2 | 6/2020 | Van Der Meulen et al. |
| 10,702,508 B2 | 7/2020 | Molina |
| 10,799,488 B2 | 10/2020 | Chen |
| 10,799,489 B2 * | 10/2020 | Chen ....................... A61P 35/00 |
| 10,849,888 B2 | 12/2020 | Chen |
| 10,857,139 B2 | 12/2020 | Jung et al. |
| 11,116,775 B2 | 9/2021 | Altschul et al. |
| 11,160,796 B2 | 11/2021 | Molina |
| 2002/0133833 A1 | 9/2002 | Sawyers et al. |
| 2003/0225138 A1 | 12/2003 | Sircar et al. |
| 2004/0009969 A1 | 1/2004 | Cleve et al. |
| 2004/0077605 A1 | 4/2004 | Salvati et al. |
| 2004/0116417 A1 | 6/2004 | Boubia et al. |
| 2005/0153968 A1 | 7/2005 | Bi et al. |
| 2006/0025589 A1 | 2/2006 | Binet et al. |
| 2006/0127902 A1 | 6/2006 | Madden et al. |
| 2007/0004753 A1 | 1/2007 | Sawyers et al. |
| 2007/0249697 A1 | 10/2007 | Tachibana et al. |
| 2007/0254933 A1 | 11/2007 | Jung et al. |
| 2008/0032935 A1 | 2/2008 | Engel et al. |
| 2009/0312295 A1 | 12/2009 | McKearn et al. |
| 2010/0190991 A1 | 7/2010 | Ouerfelli et al. |
| 2011/0003839 A1 | 1/2011 | Jung et al. |
| 2013/0045204 A1 | 2/2013 | Andersen et al. |
| 2013/0072511 A1 | 3/2013 | Jung et al. |
| 2013/0079241 A1 | 3/2013 | Luo et al. |
| 2013/0116258 A1 | 5/2013 | Smith et al. |
| 2013/0225821 A1 | 8/2013 | Ouerfelli et al. |
| 2013/0253035 A1 | 9/2013 | McDonnell et al. |
| 2014/0088129 A1 | 3/2014 | Chen |
| 2014/0187641 A1 | 7/2014 | Dalton et al. |
| 2014/0199236 A1 | 7/2014 | Chen et al. |
| 2014/0309262 A1 | 10/2014 | Jung et al. |
| 2014/0314860 A1 | 10/2014 | Shah et al. |
| 2015/0133481 A1 | 5/2015 | Dilhas et al. |
| 2016/0376252 A1 | 12/2016 | Smith et al. |
| 2018/0318277 A1 | 11/2018 | Chen |
| 2019/0151335 A1 | 5/2019 | Altschul et al. |
| 2019/0269667 A1 | 9/2019 | Chen |
| 2019/0269668 A1 | 9/2019 | Chen |
| 2021/0177821 A1 | 6/2021 | Chen et al. |
| 2021/0361675 A1 | 11/2021 | Altschul et al. |
| 2022/0054468 A9 | 2/2022 | Molina |

FOREIGN PATENT DOCUMENTS

| | | |
|---|---|---|
| AU | 2013323861 A1 | 4/2015 |
| AU | 2018206695 C1 | 10/2020 |
| CN | 101032483 A | 9/2007 |
| CN | 101032486 A | 9/2007 |
| CN | 101454002 A | 6/2009 |
| CN | 101528308 A | 9/2009 |
| CN | 101528309 A | 9/2009 |
| CN | 104661658 A | 5/2015 |
| CN | 104857157 A | 8/2015 |
| DE | 2102605 | 7/1971 |
| DE | 2614831 | 10/1977 |
| EA | 030128 | 6/2018 |
| EP | 0002259 A2 | 6/1979 |
| EP | 0017976 A2 | 10/1980 |
| EP | 0144098 A1 | 6/1985 |
| EP | 0331232 A2 | 9/1989 |
| EP | 0362179 A2 | 4/1990 |
| EP | 0494819 A1 | 7/1992 |
| EP | 0572191 A1 | 12/1993 |
| EP | 0578516 A1 | 1/1994 |
| EP | 0580459 A1 | 1/1994 |
| EP | 0721944 A1 | 7/1996 |
| EP | 0770613 A1 | 5/1997 |
| EP | 1632477 A1 | 3/2006 |
| EP | 1007080 B1 | 4/2007 |
| EP | 1790640 A1 | 5/2007 |
| EP | 2439196 A1 | 4/2012 |
| EP | 2900224 A1 | 8/2015 |
| EP | 3305285 A1 | 4/2018 |
| FR | 2693461 A1 | 1/1994 |
| FR | 2715402 A1 | 7/1995 |
| FR | 2845384 A1 | 4/2004 |
| FR | 2845385 A1 | 4/2004 |
| GB | 0800244 A | 8/1958 |
| HK | 1212221 A1 | 6/2016 |
| HU | 217893 | 5/2000 |
| ID | 2016/03647 | 5/2016 |
| ID | 16033432 | 5/2016 |
| JP | 59-210083 A | 11/1984 |
| JP | 60-239737 A | 11/1985 |
| JP | 64-009978 A | 1/1989 |
| JP | 1009978 | 1/1989 |
| JP | 02-019363 A | 1/1990 |
| JP | 08-009997 | 1/1996 |
| JP | 10-009978 A | 1/1998 |
| JP | 2845384 B2 | 1/1999 |
| JP | 2003-530348 | 10/2003 |

(56) References Cited

FOREIGN PATENT DOCUMENTS

| | | |
|---|---|---|
| JP | 2004-525175 | 8/2004 |
| JP | 2004-252175 A | 9/2004 |
| JP | 2006-022118 A | 1/2006 |
| JP | 2006-510600 | 3/2006 |
| JP | 2006-265244 A | 10/2006 |
| JP | 2008-512419 A | 4/2008 |
| JP | 2008-099977 A | 5/2008 |
| JP | 2008-540523 | 11/2008 |
| JP | 2009-531439 | 9/2009 |
| JP | 2010-500975 A | 1/2010 |
| JP | 2010-504307 A | 2/2010 |
| JP | 2011-503075 A | 1/2011 |
| JP | 2011-068653 A | 4/2011 |
| JP | 2012-211190 A | 11/2012 |
| JP | 2012-236843 A | 12/2012 |
| JP | 5133975 B2 | 1/2013 |
| JP | 2015-534582 A | 12/2015 |
| JP | 2016-508991 A | 3/2016 |
| JP | 6351597 B2 | 7/2018 |
| JP | 2018-150365 A | 9/2018 |
| MX | 2015003909 A | 1/2016 |
| NZ | 705815 A | 8/2018 |
| UA | 117663 | 9/2018 |
| WO | 90/13646 A1 | 11/1990 |
| WO | 97/00071 A1 | 1/1997 |
| WO | 97/13646 A1 | 4/1997 |
| WO | 97/19064 A1 | 5/1997 |
| WO | 97/19931 A1 | 6/1997 |
| WO | 00/17163 A1 | 3/2000 |
| WO | 00/26195 A1 | 5/2000 |
| WO | 00/44731 A1 | 8/2000 |
| WO | 01/07048 A1 | 2/2001 |
| WO | 01/92253 A2 | 12/2001 |
| WO | 01/94346 A1 | 12/2001 |
| WO | 02/53155 | 7/2002 |
| WO | 02/81453 | 10/2002 |
| WO | 03/29245 | 4/2003 |
| WO | 03/32994 | 4/2003 |
| WO | 03/57220 | 7/2003 |
| WO | 03/93243 | 11/2003 |
| WO | 03/96980 | 11/2003 |
| WO | 2004/022572 A1 | 3/2004 |
| WO | 2004/030633 A2 | 4/2004 |
| WO | 2004/031160 A2 | 4/2004 |
| WO | 2004/070050 A2 | 8/2004 |
| WO | 2004/111031 A1 | 12/2004 |
| WO | 2005/042488 A1 | 5/2005 |
| WO | 2005/059109 A2 | 6/2005 |
| WO | 2005/060661 A2 | 7/2005 |
| WO | 2005/089752 A2 | 9/2005 |
| WO | 2005/099693 A2 | 10/2005 |
| WO | 2006/010642 A1 | 2/2006 |
| WO | 2006/027266 A1 | 3/2006 |
| WO | 2006/028226 A1 | 3/2006 |
| WO | 2006/124118 A1 | 11/2006 |
| WO | 2007/012661 A1 | 2/2007 |
| WO | 2007/045877 A1 | 4/2007 |
| WO | 2007/126765 A2 | 11/2007 |
| WO | 2007/127010 A2 | 11/2007 |
| WO | 2008/034909 A2 | 3/2008 |
| WO | 2008/119015 A2 | 10/2008 |
| WO | 2009/055053 A2 | 4/2009 |
| WO | 2009/061587 A1 | 5/2009 |
| WO | 2009/101530 A1 | 8/2009 |
| WO | 2010/099238 A1 | 9/2010 |
| WO | 2011/103202 A2 | 8/2011 |
| WO | 2011/106570 A1 | 9/2011 |
| WO | 2012/018948 A2 | 2/2012 |
| WO | 2012/142208 A1 | 10/2012 |
| WO | 2012/145330 A1 | 10/2012 |
| WO | 2012/158884 A1 | 11/2012 |
| WO | 2013/066440 A1 | 5/2013 |
| WO | 2013/079964 A1 | 6/2013 |
| WO | 2013/152342 A1 | 10/2013 |
| WO | 2013/153342 A1 | 10/2013 |
| WO | 2013/184681 A1 | 12/2013 |
| WO | 2014/043208 A1 | 3/2014 |
| WO | WO-2014052237 A1 * | 4/2014 ............ A61P 35/00 |
| WO | 2014/113260 A1 | 7/2014 |
| WO | 2016/090098 A1 | 6/2016 |
| WO | 2016/090101 A1 | 6/2016 |
| WO | 2016/090105 A1 | 6/2016 |

OTHER PUBLICATIONS

De Bono et al., "Abiraterone and Increase Survival in Metastatic Prostate Cancer", The New England Journal of Medicine, vol. 364, No. 21, pp. 1995-2005 (2011).*

Reagan-Shaw, et al., "Dose Translation from Animal to Human Studies Revisited", 2007, 22, 659-661.

Remington: Practice of The Science and Pharmacy, 19th Edition, Table of Contents, Gennaro (ed.), 1995, Mack Publishing Company, Easton, PA, 5 pages.

Richards, et al., "Interactions of Abiraterone, Eplerenone, and Prednisolone with Wild-type and Mutant Androgen Receptor: A Rationale for Increasing Abiraterone Exposure or Combining with MDV3100", Cancer Research, US, (Mar. 12, 2012), vol. 72, No. 9, doi: 10.1158/0008-5472.CAN-11-3980, ISSN 0008-5472, pp. 2176-2182.

Riegman, et al., Molecular Endocrinology, The Promoter of the Prostate-Specific Antigen Gene Contains a Functional Androgen Responsive Element, 1991, pp. 1921-1930.

Rooseboom et al., "Enzyme-Catalyzed Activation of Anticancer Prodrugs", Pharmacological Reviews, 2004, 56, 53-102.

Ryan et al., "Abiraterone in Metastatic Prostate Cancer without Previous Chemotherapy", New England Journal of Medicine, Jan. 10, 2013, vol. 368, No. 2, 138-148.

Sack et al., "Crystallographic Structures of the Ligand-Binding Domains of the Androgen Receptor and its T877A Mutant Complexed with the Natural Agonist Dihydrotestosterone", Proc Natl Acad Sci, 2001, 98(9), 4904-4909.

Sambrook et al., "Molecular Cloning: A Laboratory Manual", 2.sup.nd Edition, Table of Contents, Cold Spring Harbor Laboratory Press, Cold Spring Harbor, 1989, 30 pages.

Sarker et al., "Targeting the PI3K/AKT Pathway for the Treatment of Prostate Cancer", Clinical Cancer Research, 2009, vol. 15, No. 15, 4799-4805.

Sartor, Urology, 2003; 61 (Supppl 2A): 25-31.

Sartor; Progression of metastatic castrate-resistant prostate cancer: impact of therapeutic intervention in the post-docetaxel space Journal of Hematology & Oncology 2011, 4:18; 1-7.

Saunders et al., "Point Mutations Detected in the Androgen Receptor Gene of Three Men with Partial Androgen Insensitivity Syndrome", Clin. Endocrinol., 1992, 37, 214-220.

Sauveur-Michel Maira et al., "Identification and characterization of NVP-BKM120, an orally available pan-class I PI3-kinase inhibitor", Molecular Cancer Therapeutics, vol. 11, No. 2, published on Dec. 21, 2011, pp. 317-328.

Schellhammer et al., "Prostate Specific Antigen Decreases after Withdrawal of Antiandrogen Therapy with Bicalutamide or Flutamide in Patients Receiving Combined Androgen Blockade", J Urol, 1997, 157, 1731-1735.

Scher et al., "Antitumour activity of MDV3100 in castration-resistant prostate cancer: a phase 1-2 study", Lancet, Apr. 24, 2010, 375(9724), 1437-1446.

Scher et al., "The Flutamide Withdrawal Syndrome: Its Impact on Clinical Trials in Hormone-Refractory Prostatic Cancer", J Clin Oncol 1993, 11, 1566-1572.

Scott, et al: Abiraterone Acetate: A Guide to Its Use in Metastatic Castration-Resistant Prostate Cancer; ADIS Drug Clinical; Drugs and Aging, 2012, vol. 29, vol. 3, 243-248.

Sderholm et al., "Three-Dimensional Structure-Activity Relationships of Nonsteroidal Ligands in Complex with Androgen Receptor Ligand-Binding Domain," J. Med. Chem., 2005, 48(4), 917-925.

Shang et al., "Molecular Determinants for the Tissue Specificity of SERMs", Science, 2002, 295, 2465-2468.

Shang, Y., Myers, M. & Brown, M. Formation of the androgen receptor transcription complex. Mol Cell 9, 2002, 601-10.

(56) References Cited

OTHER PUBLICATIONS

Sharifi et al., Advanced Drug Delivery Reviews, vol. 28, No. 1, 1997, pp. 121-138.
Shi, Xu-Bao, et al., "Functional analysis of 44 mutant androgen receptors from human prostate cancer", Cancer Research 62 (5), pp. 1496-1502 (Mar. 1, 2002).
Shiau et al., "The Structural Basis of Estrogen Receptor/Coactivator Recognition and the Antagonism of this Interaction by Tamoxifen", Cell, 1998, 95, 927-937.
Shore et al.: "Novel Antiandrogen ARN-509 in High-Risk Nonmetastatic CastrationResistant Prostate Cancer", The Journal of Urology, vol. 193, No. 4S, May 19, 2015 (May 19, 2015).
Shore: "Darolutamide (ODM-201) for the treatment of prostate cancer", Expert Opinion on Pharmacotherapy, vol. 18, No. 9, Jun. 13, 2017 (Jun. 13, 2017), pp. 945-952, London, UK, ISSN: 1465-6566, DOI: 10.1080/14656566.2017.1329820.
Simone, "Oncology", Cecil Textbook of Medicine, 20th Edition, 1996, vol. 1, 1004-1010.
Singh et al. "Self-Emulsifying Drug Delivery Systems (SEDDS): Formulation Development, Characterization, and Applications "Critical Reviews"" in Therapeutic Drug Carrier Systems, 26 (5), 427-521 (2009).
Singh et al., "Androgen Receptor Antagonists (Antiandrogens): Structure-Activity Relationships", Current Medicinal Chemistry, 2000, 7, 211-247.
Smith et al., "ARN-509 in Men With High Risk Nonmetastatic Castration-Resistant Prostate Cancer", Annals of Oncology; Abstract Book of the 37th ESMO Congress, Kluwer, Dordrecht, Vienna, Austria, vol. 23, No. Suppl. 9, Sep. 17, 2012 (Sep. 17, 2012), p. 303.
Smith Matthew R et al: "Phase 2 Study of the Safety and Antitumor Activity of Apalutamide (ARN-509), a Potent Androgen Receptor Antagonist, in the High-risk Non metastatic Castrationresistant Prostate Cancer Cohort", European Urology, Elsevier, Amsterdam, NL, vol. 70, No. 6, May 6, 2016 (May 6, 2016), pp. 963-970, ISSN: 0302-2838, DOI: 10.1016/J.EURUR0.2016.04.023.
Sonpavde, "Abiraterone acetate for metastatic prostate cancer" Lancet Oncology (2012), vol. 12, Issue 10, pp. 958-959.
Soto et al., "Control of Cell Proliferation: Evidence for Negative Control on C141 Estrogen-Sensitive T47D Human Breast Cancer Cells", Cancer Research, 1986, 46, 2271-2275.
Sperry et al., Androgen Binding Profiles of Two Distinct Nuclear Androgen Receptors in Atlantic Croaker (Micropogonias Undulates), Journal of Steroid Biochemistry & Molecular Biology, 2000, 73, 93-103.
Stinchcomb et al., "Isolation and Characterisation of a Yeast Chromosomal Replicator", 1979, 282, 39-43.
Su et al., "Polymorphisms of Androgen Receptor Gene in Childhood and Adolescent Males with First-Onset Major Depressive Disorder and Association with Related Symptomatology", Int. J. Neurosci., 2007, 117, 903-917.
Sweet et al., "A Unique Point Mutation in the Androgen Receptor Gene in a Family with Complete Androgen Insensitivity Syndrome", Fertil. Steril., 1992, 58(4), 703-707.
Szelei et al., Androgen-Induced Inhibition of Proliferation in Human Breast Cancer MCF7 Cells Transfected with Androgen Receptor. Endocrinology. 1997. v. 138 (4). pp. 1406-1412.
Takemoto et al., "Novel Pottasium Chanel Openers: Synthesis and Pharmacological Evaluation of New N-(substituted-3-pyridyl)-N'-alkylthioureasand Related Compounds", J Med. Chem., 1994, 37(1), 18-25.
Taplin et al. "Selection for Androgen Receptor Mutations in Prostate Cancers Treated with Androgen Antagonist", Cancer Res, 1999, 59, 2511-2555.
Taplin et al., "Androgen Receptor Mutations in Androgen-Independent Prostate Cancer: Cancer and Leukemia Group B Study 9663", J Clin Oncol, 2003, 21, 2673-2678.
Taplin et al., "Mutation of the Androgen-Receptor Gene in Metastatic Androgen Independent Prostate Cancer", N Engl J Med, 1995, 332(21), 1393-1398.
Tenuta, et al., "Clinical trial risk in castration-resistant prostate cancer: immunotherapies show promise", BJU Int 2014; 113; E82-E89.
Teutsch et al., "Non-steroidal Antiandrogens: Synthesis and Biological Profile of High-affinity Ligands for the Androgen Receptor", J. Steroid Biochem. Mol. Biol., 1994, 48, 111-119.
The Pharmacological Basis of Therapeutics, Goodman and Gilman, eds., Macmillan Publishing Co., New York, 1941.
Tombal, "Non-metastatic CRPC and asymptomatic metastatic CRPC: which treatment for which patient?", Annals of Oncology, 2012, 23(Suppl. 10), x251-x258.
Tran, Chris et al., "Development of a Second-Generation Anti androgen for Treatment of Advanced Prostate Cancer", Science (Washington D C), vol. 324, No. 5928, May 2009 (May 2009), pp. 787-790.
Tremblay et al., "Ligand-Independent Recruitment of SRC-1 to Estrogen Receptor Beta through Phosphorylation of Activation Function AF-1", Mol Cell, 1999, 3, 513-519.
Tschumper et al., "Sequence of a Yeast DNA Fragment Containing a Chromosomal Replicator and the TRP1 Gene", Gene, 1980, 10, 157-166.
U.S. Appl. Jung et al., filed Mar. 27, 2006., U.S. Appl. No. 60/785,978.
Urlaub et al., "Isolation of Chinese Hamster Cell Mutants Deficient In Dihydrofolate Reductase Activity", Proc. Natl. Acad. Sci. USA, 1980, 77(7), 4216-4220.
Abstract submitted by Samedy Ouk, Prostate Cancer Foundation Scientific Retreat, Scottsdale, Arizona, Sep. 29-Oct. 1, 2005.
Al-Salama Zaina T: "Apalutamide: First Global Approval", Drugs, ADIS International Ltd, NZ, vol. 78, No. 6, Mar. 31, 2018 (Mar. 31, 2018), pp. 699-705, ISSN: 1179-1950, DOI: 10.1007/S40265-018-0900-Z.
Alva et al., "1. Phase II study of Cilengitide (EMD 121974, NSC 707544) in Patients with Non-Metastatic Castration Resistant Prostate Cancer, NCI-6735. A study by the DOD/PCF Prostate Cancer Clinical Trials Consortium", Investigational New Drugs, 2012, 30(2), 749-757.
Amaral et al., "Castration-Resistant Prostate Cancer: Mechanisms, Targets, and Treatment", Hindawi Publishing Corporation, Prostate Cancer, Epub Mar. 5, 2012, vol. 2012, Article ID 327253, 11 pages.
American Urological Association—Castration-Resistant Prostate Cancer—https://www.auanet.org/education/guidelines/castration-resistant-prostate-cancer.cfm.
Anonymous, "A Study to Determine Safety and Tolerability of Enzalutamide (MDV3100) in Combination With Abiraterone Acetate in Bone Metastatic Castration-Resistant Prostate Cancer Patients-", (Jul. 26, 2012), pp. 1-12, URL: https://clinicaltrials.gov/ct2/show/NCT01650194, (Jan. 7, 2020).
Anonymous: "NCT01946204 on Sep. 18, 2013: A Study of ARN-509 in Men With Non-Metastatic Castration-Resistant Prostate Cancer", ClinicalTrials.gov Archive, Sep. 18, 2013 (Sep. 18, 2013), pp. 1-4, XP55251019, Retrieved from the Internet: URL:https://clinicaltrials.gov/archive/NCT01946204/2013_09_18 [retrieved on Feb. 17, 2016].
Antonarakis, Eur Urol Rev., Management of metastatic castration-resistant prostate cancer, 2011 ; 6(2): 90-96.
ARN-509 Update: Phase I Study—Prostate Cancer, HealingWell.com, 2014, 3 pages.
Auricchio et al., "VAL 201—An Inhibitor of Androgen Receptor-associated Src and a Potential Treatment of Castration-resistant Prostate Cancer", European Oncology & Hematology, 2012, vol. 8, No. 1, 32-35.
Ausubel et al., "Current Protocols in Molecular Biology", Wiley Interscience Publishers, 1995, 2, 18 pages.
Baek et al., "Exchange of N-CoR Corepressor and Tip60 Coactivator Complexes Links Gene Expression by NF-kappaB and Beta-Amyloid Precursor Protein", Cell, 2002, 110, 55-67.
Baibas et al., "Overcoming mutation-based resistance to antiandrogens with rational drug design", eLife, Apr. 2013, e00499.
Balk, "Androgen Receptor as a Target in Androgen-Independent Prostate Cancer", Urology, 2002, 60(3A), 132-138.

(56) References Cited

OTHER PUBLICATIONS

Batch et al., "Androgen Receptor Gene Mutations Identified by SSCP in Fourteen Subjects with Androgen Insensitivity Syndrome", Hum. Mol. Genet., 1992, 1(7), 497-503.
Body, "Prevention and treatment of side-effects of systemic treatment: bone loss", Annals of Oncology, 2010, vol. 21, Supplement 7, vii180-vii185.
Bohl et al., "Structural Basis for Antagonism and Resistance of Bicalutamide in Prostate Cancer", Proc. Nat. Acad. Sci., 2005, 102(17), 6201-6206.
Bredenberg, S. et al. (Jan. 1, 2003). "New Concepts in Administration of Drugs in Tablet Form," Comprehensive Summaries of Uppsala Dissertations from the Faculty of Pharmacy ACTA Universitatis Upsaliensis Uppsala, 83 pages.
Brockschmidt et al., "The Two Most Common Alleles of the Coding GGN Repeat in the Androgen Receptor Gene Cause Differences in Protein Function", J. Mol. Endocrinol., 2007, 39, 1-8.
Bundgaard, "Design of Application of Prodrugs", Harwood Academic Publishers, 1991, Chapter 5, 113-191.
Burnstein et al. Androgen Glucocorticoid Regulation of Androgen Receptor cDNA Expression. Molecular and Cellular Endocrinology. 1995. v. 115, p. 177-186.
Butler, "Mammalian Cell Biotechnology: A Practical Approach", 1991, 6 pages.
Cai et al., "c-Jun Has Multiple Enhancing Activities in the Novel Cross Talk Between the Androgen Receptor and ETS Variant Gene 1 In Prostate Cancer", Mol. Cancer Res., 2007, 5(7), 725-735.
Carver et al., "Reciprocal Feedback Regulation of P13K and Androgen Receptor Signaling in PTEN-Deficient Prostate Cancer", Cancer Cell., 2011, 19, 575-586.
Castration-Resistant Prostrate Cancer, American Urological Association, www.auanet.org/education/guidelines/castration-resistant-prostate-cancer-cfm, 2015, 21 pages.
Chang et al., "Molecular Cloning of Human and Rat Complementary DNA Encoding Androgen Receptors", Science, 1988, 240, 324-326.
Chen, et al., Molecular determinants of resistance to antiandrogen therapy; Nature Medicine; vol. 10, No. 1, Jan. 2014; 33-39.
Chobanian et al., "A Facile Microwave-Assisted Palladium-Catalyzed Cyanation of Aryl Chlorides", Tetrahed Lett., 2006, 47(19), 3303-3035.
Cinar et al. "Androgen Receptor Mediates the Reduced Tumor Growth, Enhanced Androgen Responsiveness, and Selected Target Gene Transactivation in Human Prostate Cancer Cell Line", Cancer Research, 2001, 61, 7310-7317.
Classification of Powders, The Pharmaceutics and Compounding Laboratory, http://pharmlabs.unc.edu/labs/powders/classification.htm, accessed Aug. 9, 2016, 2 pages.
Clegg et al. (2012) ARN-509: A Novel Antiandrogen for Prostate Cancer Treatment. Cancer Research, 72(6):1494-1503 (Year: 2012).
Cook et al., "Development of GnRH Antagonists for Prostate Cancer: New Approaches to Treatment", The Oncologist, 2000, 5, 162-168.
Cousty-Berlin, et al., "Preliminary Pharmacokinetics and Metabolism of Novel Non-steroidal Antiandrogens in the Rat: Relation of their Systemic Activity to the Formation of a Common Metabolite," J. Steroid Biochem. Malec. Biol., vol. 51, No. 1/2, pp. 47-55 (1994).
Craft et al., "A Mechanism for Hormone-Independent Prostate Cancer Through Modulation of Androgen Receptor Signaling by the HER-2/Neu Tyrosine Kinase", Nature Medicine, 1999, 5(3), 280-285.
Craft et al., "Evidence for Clonal Outgrowth of Androgen-Independent Prostate Cancer Cells from Androgen-Dependent Tumors Through a Two-Step Process", Cancer Res, 1999, 59, 5030-5036.
Creaven et al., "Pharmacokinetics and Metabolism of Nilutamide", Supp. Urology, 1991, 37(2), 13-19.
Depalo et al., "GnRH agonist versus GnRH antagonist in in vitro fertilization and embryo transfer (IVF/ET)", Reproductive Biology and Endocrinology, 2012, 10, 26-33.

DePrimo et al. "Transcriptional Programs Activated by Exposure of Human Prostate Cancer Cells to Androgen", Genome Biology, 2002, 3(7), 1-12.
Design of Prodrugs, edited by H. Bundgaard, (Elsevier, 1985).
Dhal et al., "Synthesis of Thiohydantoins, Thiazolidones and their Derivatives from N1-(4'-aryl thiazole 2'-YL) Thioureas", J. Indian Chem. Soc., 1973, 50(1), 680-684.
Dorwald, F. Zaragoza. Side Reactions in Organic Synthesis: A Guide to Successful Synthesis Design, Weinheim: WILEY-VCH Verlag GmbH & Co. KGaA, 2005, Preface.
Edwards et al., "Androgen Receptor Gene Amplification and Protein Expression in Hormone Refractory Prostate Cancer", British Journal of Cancer, 2003, 89, 552-556.
Ellis et al., "Characterization of a Novel Androgen-Sensitive, Prostate-Specific Antigen-Producing Prostatic Carcinoma Xenograft: LuCaP 23", Clin Cancer Res, 1996, 2, 1039-1048.
Ellwood-Yen et al., "Myc-Driven Murine Prostate Cancer Shares Molecular Features with Human Prostate Tumors", Cancer Cell, 2003, 4(3), 223-238.
Elokdah, Hassan, et al., "Design, synthesis, and biological evaluation of thio-containing compounds with serum HDL-cholesterol-elevating properties", J. Med. Chem. 47:681-695 (2004).
Fact Sheet-Prostrate-Specific Antigen (PSA) Test, 2014, National Cancer Institute, 6 pages.
FDA ODAC Briefing Document; "Issues Concerning the Development of Products for the Treatment of Patients with Non-Metastatic Castration-Resistant Prostate Cancer"; Sep. 4, 2011; 9 pages.
FDA: "FDA approves new treatment for a certain type of prostate cancer using novel clinical trial endpoint", Feb. 14, 2018 (Feb. 14, 2018), Retrieved from the Internet: URL:https//www.fda.gov/newsevents/newsroom/pressannouncements/ucm596768.htm [retrieved on Jul. 12, 2018] XP-002783009; 4 pages.
Feher et al., "BHB: A Simple Knowledge-Based Scoring Function to Improve the C95 Efficiency of Database Screening", J. Chem. Inf. Comput. Sci., 2003, 43(4), 1316-1327.
Feldman et al., "The Development of Androgen-Independent Prostate Cancer", Nature Reviews Cancer, 2001, 1, 34-45.
Van Dort et al., "Design, Synthesis, and Pharmacological Characterization of 4-[ 4,4-Dimethyl-3-(4-hydroxybutyl)-5-oxo-2-thioxo-1-imidazolidinyl]-2-iodobenzonitrile as a High-Affinity Nonsteroidal Androgen Receptor Ligand", J. Med. Chem., 2000, 43, 3344-3347.
Vargas, et al., The Journal of Nuclear Medicine; Reproducibility and Repeatability of Semiquantitative 18 F-Fluorodihydrotestosterone Uptake Metrics in Castration-Resistant Prostate Cancer Metastases: A Prospective Multicenter Study; Oct. 2018; vol. 59, No. 10; pp. 1516-1523.
Veldscholte et al., "A Mutation in the Ligand Binding Domain Of The Androgen Receptor of Human LNCaP Cells Affects Steroid Binding Characteristics and Response to Antiandrogens", Biochem Biophys Res Commun, 1990, 173, 534-540.
Visakorpi et al., "In Vivo Amplification of the Androgen Receptor Gene and Progression of Human Prostate Cancer", Nat Genetics, 1995, 9, 401-406.
Vogelzang, Nicholas, et al: Goserlin Versus Orchiectomy in the Treatment of Advanced Prostate Cancer: Final Results of a Randomized Trial; Urology, 46 (2), 1995, 220-226.
Wainstein et al., "CWR22: Androgen-Dependent Xenografl Model Derived from a Primary Human Prostatic Carcinoma", Cancer Res, 1994, 54, 6049-6052.
Wallen et al., "Androgen Receptor Gene Mutations in Hormone-Refractory Prostate Cancer", J. Pathology 1999, vol. 189, pp. 559-563.
Wang et al., "Overexpressed Androgen Receptor Linked to p21 WAF1 Silencing May Be Responsible for Androgen Independence and Resistance to Apoptosis of a Prostate Cancer Cell Line", Cancer Research, 2001, 61(20), 7544-7551.
Wang et al., "Prostate-Specific Deletion of the Murine Pten Tumor Suppressor Gene Leads to Metastatic Prostate Cancer", Cancer Cell, 2003, 4, 209-221.
Wermuth et al., "Designing Prodrugs and Bioprecursors, I: Carrier Prodrugs", The Pharmacological Basis of Therapeutics, The Practice of Medicinal Chemistry, Goodman and Gilman, eds., Macmillan Publishing Co., New York, Chapter 31, 1996, 28 pages.

(56) References Cited

OTHER PUBLICATIONS

Wermuth, "Molecular Variations Based on Isosteric Replacements", The Practice of Medicinal Chemistry, 1996, 13, 203-237.
Wolf, et al, Molecular Endocrinology, Transcriptional Regulation of Prostate Kallikrein-Like Genes by Androgen, 1992, vol. 6, No. 5, pp. 753-762.
Wooster et al., "A Germline Mutation in the Androgen Receptor Gene in Two Brothers with Breast Cancer and Reifenstein Syndrome", Nat. Genet., 1992 ,2, 132-134.
Yoshino et al., Design and synthesis of an androgen receptor pure antagonist (CH5137291) for the treatment of castration-resistant prostate cancer. Bioorg Med Chem. Dec. 1, 2010;18(23):8150-7. doi: 10.1016/j.bmc.2010.10.023. Epub Oct. 15, 2010.
Zakikhani et al., "Metformin is an AMP Kinase-Dependent Growth Inhibitor for Breast Cancer Cells", Cancer Res, 2006, 66(21), 10269-10273.
Zarghami et al., "Steroid Hormone Regulation of Prostate-Specific Antigen Gene Expression in Breast Cancer", British Journal of Cancer, 1997, 75(4), 579-588.
Zhau et al., "Androgen-Repressed Phenotype in Human Prostate Cancer", Proc Natl Acad Sci USA, 1996, 93, 15152-15157.
Zheng, Q., et al., "Synthesis and Nonlinear Optical Properties of p-(Dimethylamino) benzylidene Dyes Containing Different Acceptors," Chemistry Letters 29, 2000, (12):1426-1427.
Zhou et al., "A Ligand-Dependent Bipartite Nuclear Targeting Signal in the Human Androgen Receptor, Requirement for the DNA-Binding Domain and Modulation by NH2-Terminal and Carboxyl-Terminal Sequences", J Bio Chem, 1994, 269(18), 13115-13123.
Zoppi et al., "Amino Acid Substitutions in the DNA-Binding Domain of the Human Androgen Receptor are a Frequent Cause of Receptor-Binding Positive Androgen Resistance", Mol. Endo., 1992, 6, 409-415.
Kuethe et al., "Synthesis of Disubstituted Imidazo[4,5-b]pyridin-2-ones", J. Org. Chem., 2004, 29, 69(22), 7752-7754.
Laitinen et al., "Chromosomal Aberrations in Prostate Cancer Xenografts Detected by Comparative Genomic Hybridization", Genes Chromosomes Cancer, 2002, 35, 66-73.
Lawrentschuk, et al: 11 Efficacy of a Second Line Luteinizing Hormone-Releasing Hormone Agonist After Advanced Prostate Cancer Biochemical Recurrence 11 , Journal of Urology, vol. 185, No. 3, Mar. 2011 (Mar. 2011), pp. 848-854, XP028358931.
Le et al. (2003). Plant-derived 3,3'-diindolylmethane Is a Strong Androgen Antagonist in Human Prostatic Cancer Cells. The Journal of Biological Chemistry, vol. 278(23), pp. 21136-21145.
LeRoith et al., "The insulin-like growth factor system and cancer", Cancer Letters, 2003, 195, 127-137.
Li et al., "Heterogeneous Expression and Functions of Androgen Receptor Co-Factors in Primary Prostate Cancer", Am J Pathol, 2002, 161(4), 1467-1474.
Linja et al., "Amplification and Overexpression of Androgen Receptor Gene in Hormone-Refractory Prostate Cancer", Cancer Research, 2001, 61, 3550-3555.
Liu et al: "Lineage relationship between LNCaP and LNCaP-derived prostate cancer cell lines", Prostate., vol. 60, No. 2, Jan. 1, 2004 (Jan. 1, 2004), pp. 98-108.
Lobaccaro et al., "Molecular Modeling and In Vitro Investigations of the Human Androgen Receptor DNA-Binding Domain: Application for the Study of Two Mutations", Mol. Cell. Endocrinol., 1996, 116, 137-147.
Lodde, Michele, et al,, Urology 76 (5), 2010, pp. 1189-1193.
Lodish et al., "Endocrine side effects of broad-acting kinase inhibitors", Endocrine-Related Cancer, 2010, 17 , R233-R244.
Lonergan, et al., Journal of Carcinogenesis, Androgen receptor signaling in prostate cancer development and progression, 2011, 19 pages.
Lu et al. "Molecular Mechanisms of Androgen-Independent Growth of Human Prostate Cancer LNCaP-AI Cells", Endocrinology 1999, vol. 140, No. 11, pp. 5054-5059.
Madan et al. (2008). Analysis of Overall Survival in Patients with Nonmetastatic Castration-Resistant Prostate Cancer Treated with Vaccine, Nilutamide, and Combination Therapy. Cancer Therapy: Clinical, vol. 14(14), pp. 4526-4531.
Manolagas et al., "Sex Steroids and Bone", Recent Prog Harm Res, 2002, 57, 385-409.
Mansour et al., "Disruption of the Proto-Oncogene int-2 In Mouse Embryo-Derived Stem Cells: A General Strategy for Targeting Mutations to Non-Selectable Genes", Nature, 1988, 336, 348-352.
Marhefka et al., "Homology Modeling Using Multiple Molecular Dynamics Simulations and Docking Studies of the Human Androgen Receptor Ligand Binding Domain Bound to Testosterone and Nonsteroidal Ligands", J. Med. Chem., 2001, 44(11), 1729-1740.
Masiello et al., "Bicalutamide Functions as an Androgen Receptor Antagonist by Assembly of a Transcriptionally Inactive Receptor", J Biol Chem, 2002, 277(29), 26321-26326.
Matias et al., "Local Inhibition of Sebaceous Gland Growth by Topically Applied RU 58841", NY Acad. Sci., 1995, 761, 56-65.
Matias et al., "Structural Basis for the Glucocorticoid Response in a Mutant Human Androgen Receptor (AR(ccr)) Derived from an Androgen-Independent Prostate Cancer", J Med Chem, 2002, 45, 1439-1446.
Matias et al., "Structural Evidence for Ligand Specificity in the Binding Domain of the Human Androgen Receptor: Implications for Pathogenic Gene Mutations", J Biol Chem, 2000, 275(34), 26164-26171.
Matsubara, et al., "Phase 1 study of darolutamide (ODM-201): a new-generation androgen receptor antagonist, in Japanese patients with metastatic castration-resistant prostate cancer"; Cancer Chemother Pharmacol, 2017, 80:1063-1072.
Matthew R. Smith et al., "Apalutamide Treatment and Metastasis-free Survival in Prostate Cancer", The New England Journal of Medicine—NEJM—, Apr. 12, 2018, vol. 378, No. 15, pp. 1408-1418.
McDonnell et al., "Expression of the Protooncogene bcl-2 in the Prostate and its Association with Emergence of Androgen-Independent Prostate Cancer", Cancer Res, 1992, 52, 6940-6944.
Migliaccio et al., "Steroid-Induced Androgen Receptor-Oestradiol Receptor beta-SRC Complex Triggers Prostate Cancer Cell Proliferation", Embo J, 2000, 19(20), 5406-5417.
Millennium-Takeda, "Press Release: Clinical Data Presented on Orteronel (TAK-700) Without Steroids in Non-Metastatic Prostate Cancer", 2012, 2 pages.
Mitsiades, et al., "Clinical appraisal of abiraterone in the treatment of metastatic prostatic cancer: patient considerations, novel opportunities, and future directions", Oncotargets and Therapy, (Jan. 1, 2013), doi:10.2147/OTT.S24941, p. 9.
Molina et al., Phase 1 study of apalutamide (ARN) plus abiraterone acetate (AA), docetaxel (D) in patients (pts) with metastatic castrate-resistant prostate cancer (mCRPC), Annals of Oncology, vol. 28, Supplement 5, Abstract No. 837TiP, Sep. 2017.
Morgan et al., "(RAD001 (Everolimus) Inhibits Growth of Prostate Cancer in the Bone and the Inhibitory Effects Are Increased by Combination With Doxetaxel and Zoledronic Acid", The Prostate, Jun. 1, 2008, 861-871.
Mulholland et al., "Cell Autonomous Role of PTEN in Regulating Castration-Resistant Prostate Cancer Growth", Cancer Cell., 2011, 19, 792-804.
Muller et al., "BCR First Exon Sequences Specifically Activate the BCRIABL Tyrosine Kinase Oncogene of Philadelphia ChromosomePositive Fluman Leukemias", Mol. & Cell, Biol., 1991,11(4), 1785-1792.
Naik et al., "Synthesis, Spectroscopic and Thermal Studies of Bivalent Transition Metal Complexes with the Hydrazone Derived from 2 Benzimidazolyl Mercaptoaceto Hydrazile and o-Hydroxy Aromatic Aldehyde", Indian Journal of Chemistry, 2008, 1793-1797.
Nam et al., Action of the Src Family Kinase Inhibitor, Dasatinib (BMS-354825), on Human Prostate Cancer Celle, Cancer Res., 2005, v. 65(20), pp. 9185-9189.
Navone et al., "Model Systems of Prostate Cancer: Uses and Limitations", Cancer Metastasis, 1999, 17, 361-371.
NCBI, "Definition: *Homo sapiens* Androgen", Nucleotide, 2007, 7 pages NM.sub.-000044<http://www.ncbi.nlm.nih.gov:80/entrez/viewer.fcgi?cmd=- Retrieve&db=nucleotide&list.sub.- uids=

(56) References Cited

OTHER PUBLICATIONS

21322251 &dopt=Gen Ban k&term=sapiens+AR+androgen+receptor+prostate+cancer&qty= 1>gi:21322251.
Norris et al. "Peptide Antagonists of the Human Estrogen Receptor", Science, 1999, 285, 744-746.
Okegawa et al., International Journal of Urology, 2010; 17:950-955 (Year: 2010).
Osanto et al., "Emerging novel therapies for advanced prostate cancer", Therapeutic Advances in Urology, 2012, vol. 4, No. 1 ,3-12.
Ouaissi et al., "Rationale for Possible Targeting of Histone Deacetylase Signaling in Cancer Diseases with a Special Reference to Pancreatic Cancer", Journal of Biomedicine and Biotechnology, 2011, 8 pages.
Ouk et al., "Development of Androgen Receptor Inhibitors for Hormone-Refractory Prostate Cancer", Prostate Cancer Foundation Meeting, Scottsdale, AZ, Sep. 29-Oct. 1, 2005, 1 page.
Penson et al: "Enzalutamide Versus Bicalutamide in Castration-Resistant Prostate Cancer: The STRIVE Trial" Journal of Clinical Oncology, vol. 34, No. 18, Jun. 20, 2016 (Jun. 20, 2016), pp. 2098-2106, US, ISSN: 0732-183X, DOI: 10.1200/JC0.2015.64.9285.
Perou et al., "Molecular Portraits of Human Breast Tumors", Nature, 2000, 406, 747-752.
Presentation of Charles Sawyers, Prostate Cancer Foundation Scientific Retreat, Scottsdale, Arizona, Sep. 29-Oct. 1, 2005.
Prostate-Specific Antigen (PSA) Test, National Cancer Institute, 2012, 6 pages.
Raffo et al. Overexpression of bcl-2 Protects Prostate Cancer Cells from Apoptosis in Vitro and Confers Resistance to Androgen Depletion in Vivo. Cancer Research. 1995. v. 55. 4438-4445.
Rathkopf et al, "A phase II study of the androgen signaling inhibitor ARN—509 in patients with castration—resistant prostate cancer (CRPC)", Journal of Clinical Oncology, May 2012 Annual Meeting of The American Society of Clinical Oncology, ASCO, vol. 30, No. 15 Supplement, Abstract TPS4697, 1 page.
Rathkopf et al., "A First-In-Human. Open-Label. Phase I/II Safety. Pharmacokinetic and Proof-of-Concept Study of ARN—509 in Patients with Progressive Advanced Castration—Resistant Prostate Cancer (CRPC )", J. of Clin. Oncol.; ASCO Annual Meeting, 2011, 29(15), 2 pages.
Rathkopf et al., "Phase I/II safety and pharmacokinetic (PK) study of ARN-509 in patients with metastatic castration—resistant prostate cancer (mCRPC): Phase I results of a Prostate Cancer Clinical Trials Consortium study", Journal of Clinical Oncology, Feb. 2012, vol. 30, No. 5 Supplement, Abstract 43, 2 pages.
Rathkopf et al: "A phase I study of the androgen signaling inhibitor ARN-509 in patients with metastatic castration-resistant prostate cancer (mCRPC).", J. Clin. Oncol. 30, Suppl. Abstr. 4548, May 30, 2012 (May 30, 2012).
Rathkopf, Dana et al: "Phase I study of ARN-509, a novel antiandrogen, in the treatment of castration-resistant prostate cancer", J Clin Onc,vol. 31 (28), Oct. 1, 2013, pp. 3525-3530, XP008166079.
U.S. Appl. No. 15/967,452, filed Apr. 30, 2018.
Fizazi et al., "Activity and safety of ODM-201 in patients with progressive metastatic castration-resistant prostate cancer (ARADES): an open-label phase 1 dose-escalation and randomized phase 2 dose expansion trial", Lancet Oncology, vol. 15, No. 9, pp. 975-985 (2014).
Foks et al., "Synthesis, Fungicidal and Antibacterial Activity of New Pyridazine Derivatives", Heterocycles, 2009, 78(4), 961-975.
Font de Mora et al., "AIB1 is a Conduit for Kinase-Mediated Growth Factor Signaling to the Estrogen Receptor", Mol. Cell. Biol., 2000, 20(14), 5041-5047.
Foury et al., "Control of the Proliferation of Prostate Cancer Cells by an Androgen and Two Antiandrogens. Cell Specific Sets of Responses", J. Steroid Biochem. Molec. Bioi., 1998, 66(4), 235-240.
Fu, et al., Biochim Biophys Acta., Progress of molecular targeted therapies for prostate cancers, 2012; 1825(2): 140-152; 27 pages.

Gelmann, "Molecular Biology of the Androgen Receptor", J. Clin. Oncol., 2002, 20, 3001- 3015.
Genentech, "A Phase I, Open-Label Study of the Safety and Pharmacokinetics of Escalating Doses of DSTP 3086S in Patients with Metastatic Castration-Resistant Prostate Cancer", Oct. 2011, 2 pages.
Geynisman Daniel M et al: "Second-generation Androgen Receptor-targeted Therapies in Nonmetastatic Castration-resistant Prostate Cancer: Effective Early Intervention or Intervening Too Early?", European Urology, Elsevier, Amsterdam, NL, vol. 70, No. 6, May 26, 2016 (May 26, 2016), pp. 971-973, ISSN: 0302-2838, DOI: 10.1016/J.EURUR0.2016.05.026.
Gioeli et al., "Androgen Receptor Phosphorylation Regulation and Identification of the Phosphorylation Sites", J Biol Chem, 2002, 277(32), 29304-29314.
Glass et al., "The Coregulator Exchange on Transcriptional Functions of Nuclear Receptors", Genes Dev., 2000, 14, 121-141.
Godbole et al., "New Insights into the Androgen-Targeted Therapies and Epigenetic Therapies in Prostate Cancer", Prostate Cancer, 2011, 1-13.
Golub et al., "Molecular Classification of Cancer: Class Discovery and Class Prediction by Gene Expression Monitoring", Science, Oct. 1999, vol. 286, 531-537.
Goubet et al., "Conversion of a Thiohydantoin to the Corresponding Hydantoin via a Ring-Opening/Ring Closure Mechanism", Tetrahedron Letters, 1996, 37(43), 7727-7730.
Grad et al., "Multiple Androgen Response Elements and a Myc Consensus Site in the Androgen Receptor (AR) Coding Region are Involved in Androgen-Mediated Up-Regulation of AR Messenger RNA", Mol Endocrinol, 1999, 13, 1896-1911.
Graham et al., "A New Technique for the Assay of Infectivity of Human Adenovirus 5 DNA", Virology, 1973, 52, 456-467.
Gregory et al., "A Mechanism for Androgen Receptor-Mediated Prostate Cancer Recurrence After Androgen Deprivation Therapy", Cancer Res., 2001, 61, 4315-4319.
Gregory et al., "Androgen Receptor Stabilization in Recurrent Prostate Cancer is Associated with Hypersensitivity to Low Androgen", Cancer Res, 2001, 61, 2892-2898.
Gullapalli, Rampurna Prasad: "Soft gelatin capsules (softgels)", Journal of Pharmaceutical Sciences, vol. 99, No. 10, Oct. 18, 2010 (Oct. 18, 2010), pp. 4107-4148, XP055090285.
Gura, "Cancer Models: Systems for Identifying New Drugs Are Often Faulty", Science, Nov. 1997, vol. 278, No. 5340, 1041-1042.
Hamilton-Reeves et al, "Isoflavone-Rich Soy Protein Isolate Suppresses Androgen Receptor Expression Without Altering Estrogen Receptor-Beta Expression or Serum Hormonal Profiles in Men at High Risk of Prostate Cancer", J. Nutr., 2007, 137, 1769-1775.
Heath Elisabeth, et al., A phase 1 dose-escalation study of oral BR-DIM (BioResponse 3,3-Diindolylmethane) in castrate-resistant, non-metastatic prostate cancer, American Journal of Translational Research, vol. 2, No. 4, 2010, pp. 402-411.
Higuchi et al., "Pro-Drugs as Novel Delivery Systems", 1975, vol. 14 of the A.C.S. Symposium Series, 6 pages.
Holzbeierlein et al., "Gene Expression Analysis of Human Prostate Carcinoma During Hormonal Therapy Identifies Androgen-Responsive Genes and Mechanisms of Therapy Resistance", Am. J. Pathology, 2004, 164(1), 217-227.
Homma et al., "Differential Levels of Human Leukocyte Antigen-Class I, Multidrugresistance 1 and Androgen Receptoi Expressions in Untreated Prostate Cancer Cells: The Robustness of Prostate Cancer", Oncol. Rep., 2007, 18, 343-346.
Hong et al., "Non Metastatic Castration-Resistant Prostate Cancer", Korean Journal of Urology, 2014, 55, 153-160.
Hormonal Treatments for Uterine Fibroids (http://www.uterine-fibroids.org/Hormonal_Treatments.html, 2010).
Horoszewicz et al., "LNCaP Model of Human Prostatic Carcinoma", Cancer Res., 1983, 43, 1809-1818.
Hou, et al., Hindawi Publishing Corpration, Advances in Urology, Redefining Hormone Sensitive Disease in Advanced Prostate Cancer, vol. 2012, Article ID ID 978531, 6 pages.
Huang et al., "AR Possess an Intrinsic Hormone-Independent Transcriptional Activity", Mol Endocrinol., 2002, 16(5), 924-937.

(56) References Cited

OTHER PUBLICATIONS

Hwang et al., "Angiogenesis inhibitors in the treatment of prostate cancer", Journal of Hematology & Oncology, 2010, vol. 3, No. 26, 1-12.
Janssen Pharmaceutical Companies: "ERLEADA safety and efficacy". See full prescribing information for ERLEADA. Retrieved from the Internet: URL:https://www.accessdata.fda.gov/drugsatfda_ docs/label/2018/21 0951 s000lbl.pdf, [retrieved on Feb. 5, 2020].
Janssen: "Submits New Drug Application to U.S. FDA for Apalutamide (ARN-509) to Treat Men with Non-Metastatic Castration-Resistant Prostate Cancer", Oct. 11, 2017 (Oct. 11, 2017) Retrieved from the Internet: URL:https://www.prnewswire.com/news-releases/janssen-submits-new-drug-application-to-usfda-for-apalutamide-arn-509-to-treat-men-with-non-metastatic-castration-resistant-prostatecancer-300534 704. html [retrieved on Jul. 12, 2018].
Johnson et al., "Relationships between drug activity in NCI preclinical in vitro and in vivo models and early clinical trials", British Journal of Cancer, 2001, 84(10), 1424-1431.
Jones, "Proteinase Mutants of *Saccharomyces erevisae*", Genetics, 1977, 85, 23-33.
Jordan, V. C. Nature Reviews: Drug Discovery, 2, 2003, 205.
Jung et al., Structure-activity relationship for thiohydantoin androgen receptor antagonists for castration-resistant prostate cancer (CRPC). J Med Chem. Apr. 8, 2010;53(7):2779-96. doi: 10.1021/jm901488g. Epub Sep. 27, 2011, 59 pages.
Kagabu, "Methyl, Trifluoromethyl, and Methoxycarbonyl-Introduction to the Fifth Position on the Pyridine Ring of Chloronicotinyl Insecticide Imidacloprid", Synth Comm. 2006, 36(9), 1235-1245.
Kapoor, et al., BMC Cancer; A phase II randomized placebo-controlled double-blind study of salvage radiation therapy plus placebo versus SRT plus enzalutamide with high-risk PSA-recurrent prostate cancer after radical prostatectomy (SALV-ENZA); 2019; 10 pages.
Karp et al., "Prostate Cancer Prevention: Investigational Approaches and Opportunities", Cancer Res., v. 56 (Dec. 15, 1996) pp. 5547-5556.
Karvonen et al., "Interaction of Androgen Receptors with Androgen Response Element in Intact Cells", The Journal of Biological Chemistry, 1997, 272(25), 15973-15979.
Kato et al., "Activation of the Estrogen Receptor through Phosphorylation by Mitogenactivated Protein Kinase", Science, 1995, 270, 1491-1494.
Kawai et al., "Site-Specific Fluorescent Labeling Of Rna Molecules By Specific Transcription Using Unnatural Base Pairs", J. Am Chem. Soc., 2005, 127(49), 17286-17295.
Kemppainen et al., "Distinguishing Androgen Receptor Agonists and Antagonists: Distinct Mechanisms of Activation by Medroxyprogesterone Acetate and Dihydrotestosterone", Mol. Endocrinol., 1999, 13, 440-454.
Keown et al., "Methods for Introducing DNA Into Mammalian Cells", Methods in Enzymology, 1990, 185, 527-537.
Kim, et al., Korean Journal of Urology, Current Treatment Strategies for Castration-Resistant Prostate Cancer, 2011, pp. 157-165.
Kingsman et al., "Replication in *Saccharomyces cerevisiae* of Plasmid pBR313 Carrying DNA from the Yeast trpl REGION", Gene, 1979, 7, 141-152.
Kinoshita et al., "Methylation of the Androgen Receptor Minimal Promoter Silences Transcription in Human Prostate Cancer", Cancer Res, 2000, 60, 3623-3630.
Klein et al., "Progression of Metastatic Human Prostate Cancer to Androgen Independence in Immunodeficient SCID Mice", Nat Med, 1997, 3(4), 402-408.
Kliment, "Re: Salvage Therapy with Bicalutamide 150 mg in Nonmetastatic Castration-Resistant Prostate Cancer", European Urology, 2011, 59(6), 1066-1067.
Kousteni et al., "Nongenotropic, Sex-Nonspecific Signaling through the Estrogen or Androgen Receptors: Dissociation from Transcriptional Activity", Cell, 2001, 104, 719-730.
Xu Guan Yu et al., "Chinese Prescription Drugs", vol. 10, No. 4, New drugs will change the current status of prostate cancer treatment, pp. 28-30.
"Endpoints in asthma drug trials—what do they means?" Drug and Therapeutics Bulletin vol. 6, vol. 44, No. 3, 2006, vol. 44, No. 3, pp. 21.
Akaza et al., "Combined Androgen Blockade With Bicalutanlide for Advanced Prostate Cancer", Cancer, 2009, pp. 3437-3445.
Amm et al., "Metastatic Castration-Resistant Prostate Cancer: Critical Review of Enzalutamide", Clinical Medicine Insights: Oncology, vol. 7, 2013, pp. 235-245.
AUA 2018, "Results from Spartan: PSA Outcomes in Patients with Nonmetastatic Castration-Resistant Prostate Cancer Treated with Apalutamide".
BIO Industry Analysis: Clinical Development Succes Rates 2006-2015.
Casodex (Registered) 1995 FDA review pp. 26, 43 and 49, accessed via https ://www. accessdata. fda. gov/drug satfda*_ docs/nda/pre96/020498Orig1 s000rev.pdf.
Casodex (Registered) 2008 FDA label.
Clinical study protocol for NCT00510718, archive version vol. 9, No. 3, Apr. 2012.
Clinical study protocol for NCT00974311; archive version, Jul. 10, 2012.
Clinical study protocol for NCT01171898, archive version 5 Mar. 22, 2012.
Clinical study protocol for NCT01212991, archive version 34, Jun. 11, 2012.
Clinical study protocol for NCT01288911, archive version 18, Aug. 24, 2012.
Clinical study protocol for NCT01317641, archive version 4 Aug. 6, 2012.
Clinical study protocol for NCT01337518, archive version 1 Apr. 18, 2012.
Clinical study protocol for NCT01664923, archive version 2 Aug. 30, 2012.
ClinicalTrials.gov search results for the term "apalutamide", first posted until Sep. 22, 2013.
Courtney et al., "The evolving paradigm of second-line hormonal therapy options for castration-resistant prostate cancer", Curr. Opin. Oneal., vol. 24, No. 3, May 2012, pp. 272-277.
Excerpt from "ESMO 2012 late-breaking, press and deferred publication abstracts", Annals of Oncology, Abstract Book of the 37th ESMO Congress, vol. 23, No. Suppl. 9, Sep. 17, 2012, p. ixe1.
Excerpt from clinicaltrials.gov: clinical study NCT0 1790126, as it was available on Sep. 12, 2013.
Excerpt from clinicaltrials.gov: clinical study NCT01547299, as it was available on Jul. 9, 2012.
Excerpt from the USPTO's assignment-register 502648248 of Jan. 23, 2014.
FDA-label for CASODEX 9 (Registered) (bicalutamide) of Nov. 2009.
FDA-label for EULEXIN® (flutamide) of Jun. 2001.
FDA-label for NOVANTRONE (Registered), (mitoxantrone) of Aug. 2008.
FDA-label for XTANDI (Registered) (enzalutamide) of Aug. 2012.
Goa L.K., Bicalutamide in advanced prostate cancer. A review, Drugs aging, vol. 12, May 1998, pp. 401-422.
Golshayan et al., "Enzalutamide: an evidence-based review of its use in the treatment of prostate cancer", Core Evidence, vol. 8, 2013, pp. 27-35.
Gomella, "Effective Testosterone Suppression for Prostate Cancer: Is There a Best Castration Therapy?", Reviews in Urology, vol. 11, No. 2, 2009, pp. 52-60.
Harrison et al., "Gonadotropin-releasing hormone and its receptor in normal and malignant cells", Endocrine-Related Cancer, vol. 11, 2004, pp. 725-748.
Heidenreich, "Guidelines and Counselling for Treatment Options in the Management of Prostate Cancer" in Prostate Cancer Springer, Berlin Heidelberg, 2007, pp. 131-162.
Jones et al., "Re: Acceptance and Durability of Surveillance as a Management Choice in Men with Screen-Detected, Low-Risk Pros-

(56) References Cited

OTHER PUBLICATIONS tate Cancer: Improved Outcomes with Stringent Enrollment Criteria", European Urology, vol. 59, 2011, pp. 1066-1070.
Leibowitz et al., "Targeting the androgen receptor in the management of castration-resistant prostate cancer: rationale progress, and future directions", Curr. Oncol., vol. 19, 2012, pp. 322-331.
McCutcheon, "Enzalutamide: A New Agent for the Prostate Cancer Treatment Armamentarium", Journal of the Advanced Practitioner in Oncology, vol. 4, No. 3, May 2013, pp. 182-185.
Menon et al., "Enzalutamide, a Second Generation Androgen Receptor Antagonist: Development and Clinical Applications in Prostate Cancer", Curr. Oneal. Rep., vol. 15, 2013, pp. 69-75.
Overview on clinical study NCT01171897 of Mar. 22, 2012, accessible via: https://clinicaltrials.gov/ct2/history/NCT01171898?V_5=View#StudyPageTop.
Ryan et al., "Androgen Receptor Rediscovered: The New Biology and Targeting the Androgen Receptor Therapeutically", Journal of Clinical Oncology, vol. 29, No. 27, Sep. 20, 2011, pp. 3651-3658.
Sadar, "Advances in small molecule inhibitors of androgen receptor for the treatment of advanced prostate cancer", World J. Urology, vol. 30, 2012, pp. 311-318.
Scher et al., "Design and End Points of Clinical Trials for Patients With Progressive Prostate Cancer and Castrate Levels of Testosterone: Recommendations of the Prostate Cancer Clinical Trials Working Group", vol. 26, No. 7, Mar. 1, 2008, pp. 1148-1159.
Schweizer et al., "Abiraterone and other novel androgen-directed strategies for the treatment of prostate cancer: a new era of hormonal therapies is born", Therapeutic Advances in Urology, vol. 4, No. 4, 2012, pp. 167-178.
Screenshot of webpage of Comprehensive Cancer Center Vienna regarding Abstract-Deadline of ESMA 2012 congress; accessible via: www.ccc.ac.at/news/singleview/kongress-deresmo-2012-in-wienabstract-deadline-ist-der-16-mai/04b878b896bfd0bbcfdab5498367 4ced/.
Small et al., "Prostate Specific Antigen Outcomes in Patients with Nonmetastatic Castration Resistant Prostate Cancer Treated with Apalutamide: Results from Phase 3 SPARTAN Study", presented at AUA 2018, May 18-21.
Table of Content, Annals of Oncology; Abstract Book of the 37th ESMO Congress, Kluver, Dordrecht, NL; Vienna, Austria, vol. 23, No. Suppl. 9, Sep. 17, 2012.
Vermorken et al., "Official Journal of the European Society for Medical Oncology and the Japanese Society of Medical Oncology", Annals of Oncology, vol. 23, No. 9, 2012, pp. i-ii.
Wayback Machine capture of https://www.esmo.org/events/vienna-2012-congress/abstract-submission.html, taken on Sep. 4, 2012.
Arneson, T.J., et al., "Androgen deprivation therapy (ADT) use in Medicare beneficiaries with nonmetastatic (M0) prostate cancer (PC) in the United States," Journal of Clinical Oncology, vol. 30, Issue 15, May 2012, pp. e15169-e15169 (Abstract).
Hager, J.H., et al., "Effect of the novel anti-androgen ARN-509 on response and seizure in castration-resistant prostate cancer models," Journal of Clinical Oncology, vol. 29, Issue 7, Mar. 2011 (abstract).
Labrie, F., et al., "Gonadotropin-Releasing Hormone Agonists in the Treatment of Prostate Cancer," Endocrine Reviews, vol. 26, No. 3, May 2005, pp. 361-379.
Massard, C., et al., "Targeting Continued Androgen Receptor Signaling in Prostate Cancer," Clinical Cancer Res., vol. 17, No. 12, Jun. 15, 2011, pp. 3876-3883.
Sundaram, S., et al., "Luteinizing hormone-releasing hormone receptor-targeted deslorelin-docetaxel conjugate enhances efficacy of docetaxel in prostate cancer therapy," Molecular Cancer Therapeutics, Vil. 8, No. 6, Jun. 2009, pp. 1655-1665.
"Pfizer and Astellas Announce Positive Top-Line Resultstrom Phase 3 PROSPER Trial of XTANDI (enzalutamide)in Patients with Non-Metastatic Castration-ResistantProstate Cancer," Pfizer, retrieved at https://www.pfizer.com/news/press-release/press-release-detail/pfizer_and_astellas_announce_positive_top_line_results_from_phase_3_prosper_trial_of_xtandi_enzalutamide_in_patents_with_non_metastatic_castration_resistant_prostate_cancer, (2017).

Higano, C. et al "Antitumor activity of MDV3100 in pre- and post-docetaxel advanced prostate cancer long-term follow-up of the phase 1-2 study," (poster presented at American Society of Clinical Oncology Genitourinary Cancers Symposium, Orlando, FL, Chicago, IL, Feb. 17, 2011).
Mukherji, D. et al. "Management of Metastatic Castration-Resistant Prostate Cancer," (2012) vol. 72, Issue 8, Cancer, pp. 1011-1028.
Tombal, B., et al., "SPARTAN—A Randomized Double-Blind, Comparative Study of ARN-509 Plus Androgen Deprivation Therapy (ADT) VS ADT Alone in Non-Metastatic Castration-Resistant Prostate Cancer (M0-CRPC)," Genitourinary Tumours, Prostate, Annals of Oncology 25 (Supplement 4):, 2014, iv255-iv279.
Smith M R. et al, "Natural History of Rising Serum Prostate-Specific Antigen in Men With Castrate Nonmetastatic Prostate Cancer," Journal of Clinical Oncology, vol. 23, Issue 13, May 2005, pp. 2918-2925.
Smith M. et al, "Denosumab and bone-metastasis-free survival in men with castration-resistant prostate cancer: results of a phase 3, randomised, placebo-controlled trial," Lancet, vol. 379, 2012, pp. 39-46.
Smith M. R. et al: "ARN-509 in Men with High Risk Non-Metastatic Castration-Resistant Prostate Cancer", poster presentation at the ESMO 2012; accessible via https://register.event-works.com/elsevier/esmo2012/ps/sf/.
Taylor R A. et al, "Stem cells in prostate cancer: treating the root of the problem," Endocrine-Related Cancer, vol. 17, 2010, pp. R273-R285.
Visentin et al. Heparin is not required for detection of antibodies associated with heparin-induced thrombocytopenia/thrombosis. J Lab Clin Med 138, 22-31 (2001).
"A Phase 1 Study of MDV3100 in Patients With Castration-Resistant (Hormone-Refractory) Prostate Cancer," NCT00510718, Apr. 14, 2009 (v8).
"A Phase 1 Study of MDV3100 in Patients With Castration-Resistant (Hormone-Refractory) Prostate Cancer," NCT00510718, Jul. 31, 2007 (v1).
"A Study of Apalutamide (ARN-509) in Men With Non-Metastatic Castration-Resistant Prostate Cancer (SPARTAN)," ClinicalTrials.gov Identifier: NCT01946204, 2021, pp. 1-8.
"IMAAGEN : Impact of Abiraterone Acetate in Prostate-Specific Antigen History of Changes for Study NCT01314118," Clinical Trials.gov, Sep. 11, 2012 (V18), pp. 1-7.
"Medivation and Astellas Complete Enrollment in Phase 3 Affirm Trial of MDV3100 in Advanced Prostate Cancer;—Clinical development of MDV3100 also initiated in Japan—," LexisNexis, 2010, pp. 1-3.
"Medivation Announces Initiation of Phase 3 Clinical Trial of MDV3100 in Advanced Prostate Cancer," LexisNexis, 2009, pp. 1-3.
"Medivation Announces Positive New Efficacy Data From Phase 1-2 Trial of MDV3100 in Advanced Prostate Cancer Patients," LexisNexis, 2009, pp. 1-3.
"Medivation Reports Second Quarter Financial Results and Provides Corporate Update," Conference Call Today at 4.30pm Eastern Time', Marketwire, Aug. 9, 2012.
"Positive data on Antisoma's ASA404 presented at ASCO," Retrieved at Small Molecules, Retrieved on Jun. 2, 2008, pp. 1-3.
Ahmed M, et al, "Adaptation and clonal selection models of castration-resistant prostate cancer: Current perspective," International Journal of Urology, vol. 20, 2013, pp. 362-371.
Bono J S D. et al, "Prednisone plus cabazitaxel or mitoxantrone for metastatic castration-resistant prostate cancer progressing after docetaxel treatment: a randomised open-label trial," Lancet, vol. 376, 2010, pp. 1147-1154.
Cougar Biotechnology, Cougar Biotechnology presents positive CB7630 Clinical Data at AACR Annual Meeting Late-Breaking Clinical Trials Session, Cougar Biotechnology, Apr. 17, 2007.
Danila D. C. et al., "Abiraterone acetate and prednisone in patients (Pts) with progressive metastatic castration resistant prostate cancer (CRPC) after failure of docetaxel-based chemotherapy," Journal of Clinical Oncology, vol. 26, Issue 15, 2008, pp. 5019.
Danila et al.., "Abiraterone acetate and prednisone in patients (Pts) with progressive metastatic castration resistant prostate cancer

(56) References Cited

OTHER PUBLICATIONS (CRPC) after failure of docetaxel-based chemotherapy," J. Clin. Oncol. (Meeting abstracts), vol. 26 (May 20 Supplement), abstract No. 5019 (2008).
De Bono et al.., "Anti-tumor activity of abiraterone acetate (AA), a CYP17 inhibitor of androgen synthesis, in chemotherapy naive and docetaxel pre-treated castration resistant prostate cancer (CRPC)," J. Clin. OncoL (Meeting abstracts),. vol. 26 (May 20 Supplement), abstract No. 5005 (2008).
Eisenberger M A. et al, "Comparison of two doses of cabazitaxel plus prednisone in patients (pts) with metastatic castration-resistant prostate cancer (mCRPC) previously treated with a docetaxel(D)-containing regimen," Journal of Clinical Oncology, vol. 30, Issue 15, 2012.
Form 10-Q filed with the United States Securities and Exchange Commission by Medivation, Inc. for the quarterly period that ended on Jun. 30, 2012.
Gocmen et al., In Vitro Investigation of the Antibacterial Effect of Ketamine; Upsala J Med Sci 113 (1) 2008: pp. 39-46.
Hoimes C J. et al, "Redefining hormone resistance in prostate cancer," Ther Adv Med Oncol, vol. 2, Issue 2, 2010, pp. 107-123.
Lara P N. et al, Randomized Phase III Placebo-Controlled Trial of Carboplatin and Paclitaxel With or Without the Vascular Disrupting Agent Vadimezan (ASA404) in Advanced Non-Small-Cell Lung Cancer, Journal of Clinical Oncology, vol. 29, Issue 22, Aug. 2011, pp. 2965-2971.
Logothetis C. J. et al, "Identification of an androgen withdrawal responsive phenotype in castrate resistant prostate cancer (CRPC) patients (pts) treated with abiraterone acetate (AA)," Journal of Clinical Oncology, vol. 26, Issue 15, 2008, pp. 5017-5017.
Logothetis et al., "Identification of an androgen withdrawal responsive phenotype in castrate resistant prostate cancer (CRPC) patients (pts) treated with abiraterone acetate (AA)," J. Clin. Oncol. (Meeting abstracts), vol. 26 (May 20 Supplement), abstract No. 5017 (2008).
LoRusso P M. et al, "Clinical Development of Vascular Disrupting Agents: What Lessons Can We Learn From ASA404?,"Journal of Clinical Oncology, 2011, pp. 2952-2955.
Medivation Reports First Quarter 2010 Financial Results and Provides Corporate Update;—Conference Call Today at 4:30 p.m. Eastern Time, 2010, pp. 1-6.
Mohler J. et al., "Prostate Cancer Clinical Practice Guidelines in Oncology," National Comprehensive Cancer Network, vol. 8, Issue 2, Feb. 2010, pp. 162-200.
Mohler. J. L. et al., "Prostate Cancer, Version 3.2012," Journal of the National Comprehensive Cancer Network, vol. 10, Issue 9, 2012, pp. 1081-1087.
News Release, 'Medivation and Astellas Announce Positive Survival Data from Interim Analysis of Phase 3 Affirm Trial of MDV3100 in Men with Advanced Prostate Cancer,' Nov. 3, 2011.
Opposition—Statement of Grounds and Particulars received for Australian Patent Application No. 2018206695 mailed on Apr. 30, 2021, 12 pages.
Oudard S. et al, "Cabazitaxel Versus Docetaxel As First-Line Therapy for Patients With Metastatic Castration-Resistant Prostate Cancer: A Randomized Phase III Trial—Firstana," Journal of Clinical Oncology, vol. 35, Issue 28, 2017, pp. 3189-3197.
Oudard S. et al, "First-line use of cabazitaxel in chemotherapy-naive patients with metastatic castrationresistant prostate cancer (mCRPC): A three-arm study in comparison with docetaxel," Journal of Clinical Oncology, vol. 30, Issue 15, 2012.
Parente P. et al, "Emerging and second line therapies for the management of metastatic castration-resistant prostate cancer: The Australian perspective," Asia-Pacific Journal of Clinical Oncology, vol. 8, 2012, pp. 31-42.
Parker C. et al, "Updated analysis of the phase III, double-blind, randomized, multinational study of radium-223 chloride in castration-resistant prostate cancer (CRPC) patients with bone metastases (ALSYMPCA)," Journal of Clinical Oncology, vol. 30, Issue 18, 2012.

Pili R. et al, "Phase II Study on the Addition of ASA404 (Vadimezan; 5,6-Dimethylxanthenone-4-Acetic Acid) to Docetaxel in CRMPC," Clin Cancer Res, vol. 16, Issue 10, 2010, pp. 2906-2914.
Rathkopf D E (Cousespondence) et al, "A first-in-human, open-label, phase I/II safety, pharmacokinetic, and proof-of-concept study of ARN-509 in patients with progressive advanced castration-resistant prostate cancer (CRPC )", Journal of Clinical Oncology; ASCO Annual Meeting 2011, American Society of Clinical Oncology, US; Chicago, IL, United States, (May 20, 2011), vol. 29, No. 15, Suppl. 1, ISSN 0732-183X, p. TPS190, XP008166220.
Rathkopf Dana E (Correspondence) et al: "Phase I/II safety and pharmacokinetic (PK) study of ARN-509 in patients with metastatic castration-resistant prostate cancer (mCRPC): Phase I results of a Prostate Cancer Clinical Trials Consortium study", Journal of Clinical Oncology, American Socieiy of Clinical Oncology, US vol. 30, No. 5, Suppl. 1 Feb. 10, 2012 (Feb. 10, 2012).
Rathkopf et al., "A First-In-Human. Open-Label. Phase 1/11 Safety. Pharmacokinetic and Proof-of-Concept Study of ARN-509 in Patients with Progressive Advanced Castration-Resistant Prostate Cancer (CRPC )", J. of Clin. Oncol.; ASCO Annual Meeting, 2011, 29(15), 2 pages.
Rathkopf et al., "A phase II study of the androgen signaling inhibitor ARN-509 in patients with castration-resistant prostate cancer (CRPC)", Journal of Clinical Oncology, Abstract book of the 2012 ASCO Annual Meeting Chicago, USA, vol. 30, issue 15 supplement May 12, 2012, TPS4697.
Rathkopf, D. et al "946TiP—ARN-509 in Men with Metastatic Castration Resistant Prostate Cancer," (CRPC) vol. 23, (2012), (Supplement 9), Annals of Oncology, ix317.
Ryan C. et al., "Impact of prior ketoconazole therapy on response proportion to abiraterone acetate, a 17-alpha hydroxylase C17,20-lyase inhibitor in castration resistant prostate cancer (CRPC)," Journal of Clinical Oncology, vol. 26, Issue 15, 2008, pp. 5018.
Ryan et al., "Impact of prior ketoconazole therapy on response proportion to abiraterone acetate, a 17-alpha hydroxylase C17,20-lyase inhibitor in castration resistant prostate cancer (CRPC)," J. Clin. Oncol. (Meeting abstracts), vol. 26 (May 20 Supplement), abstract No. 5018 (2008).
Ryan et al.., "Prostate Specific Antigen Only Androgen Independent Prostate Cancer: Natural History, Challenges in Management and Clinical Trial Design." J, Urology, vol. 178:S25-S29 (2007).
Ryan, et al., "Phase I Clinical Trial of the CYP17 Inhibitor Abiraterone Acetate Demonstrating Clinical Activity in Patients With Castration-Resistant Prostate Cancer Who Received Prior Ketoconazole Therapy",Janssen Exhibit 2133, Wockhardt vs. Janssen, Case # IPR2016-01582, Journal of Clinical Oncology vol. 28, No. 9. Mar. 20, 2010 pp. 1481-1488.
Sartor O. et al, "Advanced Prostate Cancer 2010: What a Year!," Clinical Genitourinary Cancer, vol. 8, Issue 1, 2010, pp. 8-9.
Sheikh N A. et al, "Sipuleucel-T immune parameters correlate with survival: an analysis of the randomized phase 3 clinical trials in men with castration-resistant prostate cancer," Cancer Immunol Immunother, vol. 62, 2013, pp. 137-147.
Sher, H.I. et al "Increased Survival with Enzalutamide in Prostate Cancer after Chemotherapy," vol. 367, (2012), Issue 13, The New England Journal of Medicine, pp. 1187-1197.
Small E.J. et al, "Prostate Cancer Evolution or Revolution," Journal of Clinical Oncology, vol. 29, Issue 27, 2011, pp. 3595-3598.
Smith et al., "Apalutamide Treatment and Metastasis-free Survival in Prostate Cancer", New England Journal of Medicine, 378, 2018, pp. 1408-1418.
Smith M R. et al, "Disease and Host Characteristics as Predictors of Time to First Bone Metastasis and Death in Men With Progressive Castration-Resistant Nonmetastatic Prostate Cancer," Cancer, 2011, pp. 2077-2085.
"Drugs@FDA: FDA-Approved Drugs," U.S. Food and Drug, retrieved at https://www.accessdata.fda.gov/scripts/cder/daf/index.cfm?event=overview.process&ApplNo=203415, retrieved on Aug. 31, 2012, p. 2.
"Hetero's letter regarding ANDS No. 217185" Apr. 18, 2022, p. 86.
"Zydus Pharmaceuticals letter regarding Erleada® (apalutamide) tablets, 60 mg ANDA No. 217113," Apr. 11, 2022, p. 83.

(56) References Cited

OTHER PUBLICATIONS

"Analysis of 695 Patent Application Claims." Annexure B, Apr. 1, 2021, p. 4.
"Analysis of 695 Patent Application Claims." Annexure C, Apr. 1, 2021, p. 4.
"Inconsistencies in the Mainwaring declaration," Jul. 6, 2021, p. 4.
Anonymous, "Highlights of prescribing information XTANDI", Jul. 1, 2018, pp. 1-29, XP055944718.
Clegg Nicola J et al: "Development of anti-androgen ARN-509 1 Supplemental Materials and Methods", Cancer Research, Mar. 1, 2012 (Mar. 1, 2012), pp. 1-13, XP055944437.
Response to Examination report for Australian Patent Application No. 2018206695 dated Jun. 3, 2020.

* cited by examiner

ANTI-ANDROGENS FOR THE TREATMENT OF NON-METASTATIC CASTRATION-RESISTANT PROSTATE CANCER

CROSS-REFERENCE TO RELATED APPLICATIONS

This application is a continuation of U.S. patent application Ser. No. 15/967,452, filed Apr. 30, 2018, which claims the benefit of U.S. Provisional Application No. 62/630,594, filed Feb. 14, 2018, U.S. Provisional Application No. 62/617,745, filed Jan. 16, 2018, and U.S. Provisional Application No. 62/572,791, filed Oct. 16, 2017, each of which are incorporated herein by reference in their entirety.

FIELD OF THE INVENTION

Disclosed herein are methods of treating non-metastatic castration-resistant prostate cancer with an approved drug product containing an anti-androgen selected from the group consisting of enzalutamide, apalutamide and darolutamide. Also disclosed are methods of selling or offering for sale an approved drug product containing an anti-androgen selected from the group consisting of enzalutamide, apalutamide and darolutamide.

BACKGROUND OF THE INVENTION

Prostate cancer is the second most frequently diagnosed cancer and the sixth leading cause of cancer death in males, accounting for 14% (903,500) of the total new cancer cases and 6% (258,400) of the total cancer deaths in males worldwide. The course of prostate cancer from diagnosis to death is best categorized as a series of clinical stages based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate stage. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal stage of the disease.

Androgen depletion is the standard treatment with a generally predictable outcome: decline in PSA, a period of stability in which the tumor does not proliferate, followed by rising PSA and regrowth as castration-resistant disease. Historically, ADT has been the standard of care for patients with metastatic prostate cancer.

Molecular profiling studies of castration-resistance prostate cancers commonly show increased androgen receptor (AR) expression, which can occur through AR gene amplification or other mechanisms.

There is a need for a next-generation AR antagonist that overcome the potential therapeutic deficiencies of existing therapies. The disclosed methods are directed to these and other important needs.

SUMMARY OF THE INVENTION

Described herein are methods of treating non-metastatic castration-resistant prostate cancer comprising, consisting of, or consisting essentially of administering a safe and effective amount of at least one anti-androgen to a male human who has or is suspected to have a non-metastatic castration-resistant prostate cancer. In some embodiments, the non-metastatic castration-resistant prostate cancer is a high risk non-metastatic castration-resistant prostate cancer. In some embodiments, a male human has said non-metastatic castration-resistant prostate cancer and has a prostate-specific antigen doubling time (PSADT) that is less than or equal to 10 months. In further embodiments, a male human having said non-metastatic castration-resistant prostate cancer has received at least one prior therapy for the treatment of cancer, optionally wherein the prior therapy for the treatment of cancer is bicalutamine or flutamide. In still further embodiments, a male human having said non-metastatic castration-resistant prostate cancer is treatment naïve. In other embodiments, a male human having said non-metastatic castration-resistant prostate cancer is an adult.

In some embodiments, administration of the anti-androgen provides an increase in the metastasis-free survival of a male human. In some embodiments, administration of the anti-androgen provides improved anti-tumor activity as measured by time to metastasis (TTM), progression-free survival (PFS) rate, time to symptomatic progression, overall survival (OS) rate, or time to initiation of cytotoxic chemotherapy. In other embodiments, administration of a safe and effective amount of the anti-androgen results in no more than a grade 3 adverse event.

In some embodiments, the anti-androgen is a second-generation anti-androgen. In certain embodiments, the anti-androgen is apalutamide, enzalutamide or darolutamide. In certain embodiments, the anti-androgen is apalutamide. In certain embodiments, the anti-androgen is enzalutamide. In certain embodiments, the anti-androgen is darolutamide.

In some embodiments, methods of treating non-metastatic castration-resistant prostate cancer comprise, consist or, or consist essentially of administering a safe and effective amount of apalutamide to a male human with a non-metastatic castration-resistant prostate cancer, wherein the apalutamide is administered orally. In some embodiments, the apalutamide is administered daily. In some embodiments, the apalutamide is administered orally on a continuous daily dosage schedule. In further embodiments, the apalutamide is administered orally at a dose of about 240 mg per day. In other embodiments, the apalutamide is administered orally at a dose of about 60 mg four times per day.

In some embodiments, the apalutamide is present in a solid oral dosage form. In some embodiments, the apalutamide is formulated as a tablet. In some embodiments, the apalutamide is formulated as a soft gel. In some embodiments, the apalutamide is formulated as a hard shell capsule.

In some embodiments, the enzalutamide is present in a solid oral dosage form. In some embodiments, the enzalutamide is formulated as a tablet. In some embodiments, the enzalutamide is formulated as a soft gel. In some embodiments, the enzalutamide is formulated as a hard shell capsule.

In some embodiments, the darolutamide is present in a solid oral dosage form. In some embodiments, the darolutamide is formulated as a tablet. In some embodiments, the darolutamide is formulated as a soft gel. In some embodiments, the darolutamide is formulated as a hard shell capsule.

Also provided herein are methods of treating non-metastatic castration-resistant prostate cancer comprising, consisting of, or consisting essentially of administering a approved drug product comprising apalutamide to a male human with a non-metastatic castration-resistant prostate cancer, wherein the dose of apalutamide is reduced when co-administered with one or more of:
 (a) a CYP2C8 inhibitor, preferably gemfibrozil or clopidogrel; or
 (b) a CYP3A4 inhibitor, preferably ketoconazole or ritonavir.

In some embodiments, the apalutamide is not co-administered with:
 (a) medications that are primarily metabolized by CYP3A4, preferably darunavir, felodipine, midazolam or simvastatin;
 (b) medications that are primarily metabolized by CYP2C19, preferably diazepam or omeprazole;
 (c) medications that are primarily metabolized by CYP2C9, preferably warfarin or phenytoin; or
 (d) medications that are substrates of UGT, preferably levothyroxine or valproic acid.

In further embodiments, the apalutamide is not co-administered with:
 (a) medications that are P-gp substrates, preferably fexofenadine, colchicine, dabigatran etexilate or digoxin; or
 (b) BCRP/OATP1B1 substrates, preferably lapatinib, methotrexate, rosuvastatin, or repaglinide.

In another aspect, described herein are methods of selling an anti-androgen comprising, consisting of, or consisting essentially of placing an antiandrogen, e.g., darolutamide, enzalutamide, apalutamide, into the stream of commerce wherein said anti-androgen includes a package insert that contains instructions for treating prostate cancer using the anti-androgen. In certain embodiments, the anti-androgen is apalutamide.

In further aspects, described herein are methods of selling an approved drug product containing an anti-androgen, e.g., darolutamide, enzalutamide, apalutamide, comprising, consisting of, or consisting essentially of placing such drug product into the stream of commerce wherein such drug product includes a package insert that contains instructions for treating prostate cancer using the anti-androgen. In certain embodiments, the anti-androgen is apalutamide.

In still further aspects, described herein are methods of offering for sale an anti-androgen comprising, consisting of, or consisting essentially of offering to place the approved drug product containing an anti-androgen, e.g., darolutamide, enzalutamide, apalutamide into the stream of commerce wherein said anti-androgen includes a package insert that contains instructions for treating prostate cancer using the anti-androgen. In certain embodiments, the anti-androgen is apalutamide In certain embodiments, the invention is directed to a method of selling an approved drug product comprising, consisting of and/or consisting essentially of darolutamide, enzalutamide, apalutamide, said method comprising, consisting of and/or consisting essentially of a sale of such drug product, wherein a label for a reference listed drug for such drug product includes instructions for treating non-metastatic castration resistant prostate cancer. In other embodiments, the drug product is an ANDA drug product or a supplemental New Drug Application drug product. In another aspect, in the case of apalutamide, the label for said reference listed drug includes a daily dose of 240 mg apalutamide and, in the case of enzalutamide, the label for the reference listed drug includes a daily dose of 160 mg enzalutamide. In the case of darolutamide, the label for the reference listed drug includes a daily dose of 1200 mg darolutamide.

In certain embodiments, the invention is directed to a method of offering for sale an approved drug product comprising, consisting of and/or consisting essentially of apalutamide, enzalutamide, or darolutamide, said method comprising, consisting of and/or consisting essentially of offering for sale of such drug product, wherein a label for a reference listed drug for such drug product includes instructions for treating non-metastatic castration resistant prostate cancer. In other embodiments, the drug product is an ANDA drug product or a supplemental New Drug Application drug product.

BRIEF DESCRIPTION OF THE DRAWINGS

The summary, as well as the following detailed description, is further understood when read in conjunction with the appended drawings. For the purpose of illustrating the disclosed methods, the drawings show exemplary embodiments of the methods; however, the methods are not limited to the specific embodiments disclosed. In the drawings.

Figure 1:
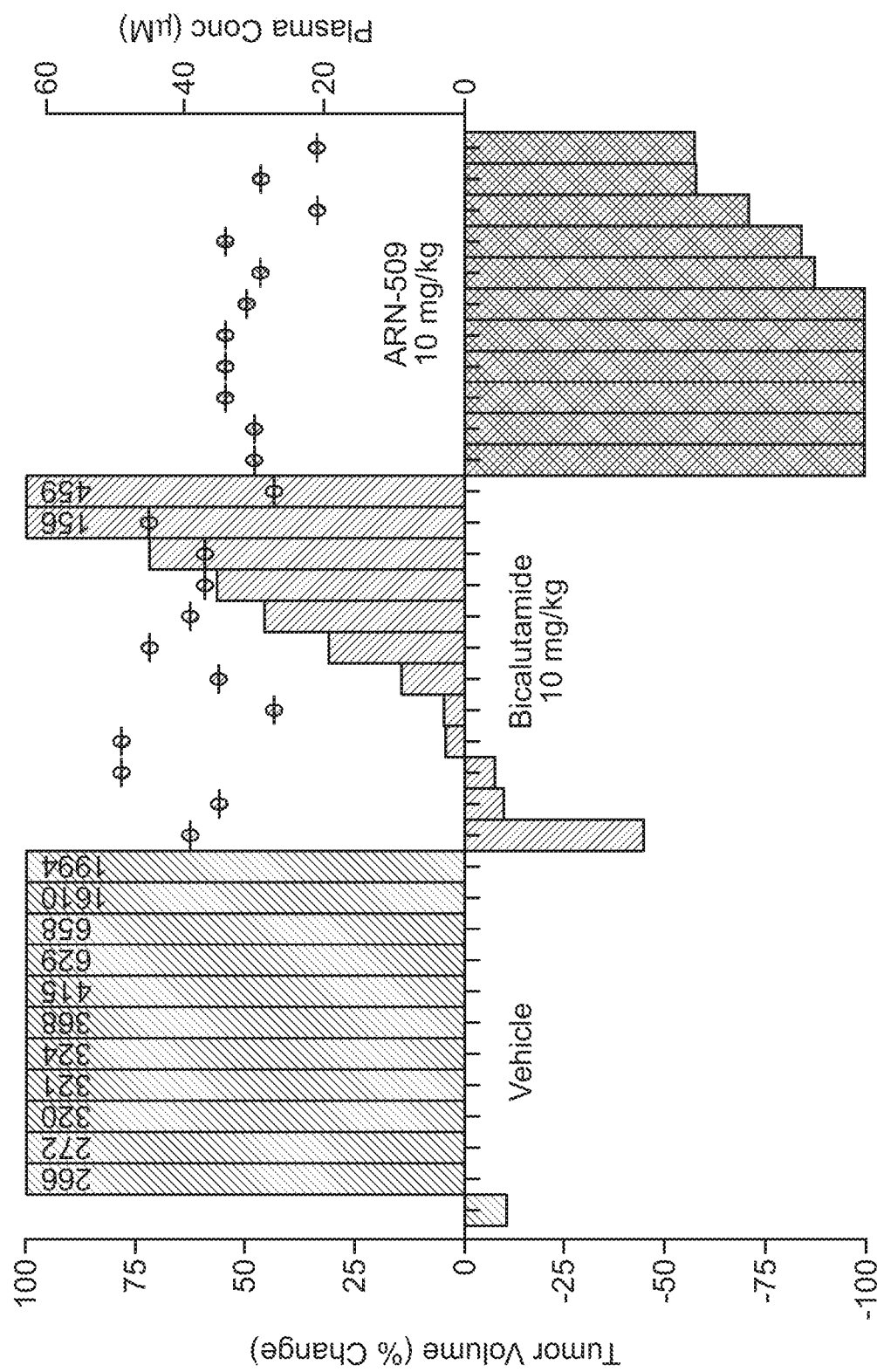
FIG. 1 illustrates tumor growth inhibition in castration-resistant LNCaP/AR-Luc xenograft model after 28 days of treatment with bicalutamide or apalutamide (ARN 509).

[b] S-warfarin was measured in the study. [c] Based on simulations. [d] See Drug Interactions (7.3 and 7.4).

DETAILED DESCRIPTION OF THE INVENTION

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of excludes any element, step, or ingredient not specified in the claim; and (iii) "consisting essentially of limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of and "consisting essentially of."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5-dihydrotestosterone (5a-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (such as using GnRH agonists) continues to be the mainstay of prostate cancer treatment. However, androgen depletion is usually effective for a limited duration and prostate cancer evolves to regain the ability to grow despite low levels of circulating androgens. Castration resistant prostate cancer (CRPC) is a lethal phenotype and almost all of patients will die from prostate cancer. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g., GnRH agonists), alone or in combination with anti-androgens (e.g., bicalutamide), which antagonize the effect of any residual testosterone on AR. The approach is effective as evidenced by a drop in PSA and regression of visible tumor (if present) in some patients; however, this is followed by regrowth as a castration resistant prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (Nat. Med, 2004, 10, 33-39). AR targeting agents with activity in castration sensitive and castration resistant prostate cancer have great promise in treating this lethal disease.

The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state. Although surgery, radiation, or a combination of both can be curative for patients with localized disease, a significant proportion of these patients have recurrent disease as evidenced by a rising level of PSA, which can lead to the development of metastases, especially in the high risk group—a transition to the lethal phenotype of the disease.

Androgen depletion is the standard treatment with a generally predictable outcome: decline in PSA, a period of stability in which the tumor does not proliferate, followed by rising PSA and regrowth as castration-resistant disease. Molecular profiling studies of castration-resistance prostate cancers commonly show increased androgen receptor (AR) expression, which can occur through AR gene amplification or other mechanisms.

Anti-androgens are useful for the treatment of prostate cancer during its early stages. However, prostate cancer often advances to a 'hormone-refractory' state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of anti-androgen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (*Science*, 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (*J Clin Oncol*, 1993. 11(8): p. 1566-72).

Prostate Cancer Stages

In the early stages of prostate cancer, the cancer is localized to the prostate. In these early stages, treatment typically involves either surgical removal of the prostate or radiation therapy to the prostate or observation only with no active intervention therapy in some patients. In the early stages where the prostate cancer is localized and requires intervention, surgery or radiation therapy are curative by eradicating the cancerous cells. About 30% of the time these procedures fail, and the prostate cancer continues to progress, as typically evidenced by a rising PSA level. Men whose prostate cancer has progressed following these early treatment strategies are said to have advanced or recurrent prostate cancer.

Because prostate cancer cells depend on the androgen receptor (AR) for their proliferation and survival, men with advanced prostate cancer are treated with agents that block the production of testosterone (e.g., GnRH agonists), alone or in combination with anti-androgens (e.g., bicalutamide), which antagonize the effect of any residual testosterone on AR. These treatments reduce serum testosterone to castrate levels, which generally slows disease progression for a period of time. The approach is effective as evidenced by a drop in PSA and the regression of visible tumors in some patients. Eventually, however, this is followed by regrowth referred to as castration-resistant prostate cancer (CRPC), to which most patients eventually succumb.

Castration-resistant prostate cancer (CRPC) is categorized as non-metastatic or metastatic, depending on whether or not the prostate cancer has metastasized to other parts of the body.

In some embodiments, prior to treatment with a second-generation anti-androgen men with non-metastatic CRPC are characterized as having the following:

1. Histologically or cytologically confirmed adenocarcinoma of the prostate without neuroendocrine differentiation or small cell features, with high risk for development of metastases.

2. Castration-resistant prostate cancer demonstrated during continuous androgen deprivation therapy (ADT)/post orchiectomy. For example defined as 3 consecutive rises of PSA, 1 week apart, resulting in two 50% increases over the nadir, with the last PSA >2 ng/mL.

3. Maintain castrate levels of testosterone (<50 ng/dL [1.72 nmol/L]) within 4 weeks of randomization and throughout the study.

4. Absence of distant metastasis by bone scan, CT or MRI scans.

Anti-Androgens

As used herein, the term "anti-androgen" refers to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR antagonist. In some embodiments, an anti-androgen is an AR full antagonist. In some embodiments, an anti-androgen is a first-generation anti-androgen. In some embodiments, an anti-androgen is a second-generation anti-androgen.

As used herein, the term "AR antagonist" or "AR inhibitor" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist, which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "first-generation anti-androgen" refers to an agent that exhibits antagonist activity against a wild-type AR polypeptide. However, first-generation anti-androgens differ from second-generation anti-androgens in that first-generation anti-androgens can potentially act as agonists in castration resistant prostate cancers (CRPC). Exemplary first-generation anti-androgens include, but are not limited to, flutamide, nilutamide and bicalutamide.

As used herein, the term "second-generation anti-androgen" refers to an agent that exhibits full antagonist activity against a wild-type AR polypeptide. Second-generation anti-androgens differ from first-generation anti-androgens in that second-generation anti-androgens act as full antagonists in cells expressing elevated levels of AR, such as for example, in castration resistant prostate cancers (CRPC). Exemplary second-generation anti-androgens include 4-[7-(6-cyano-5-trifluoromethylpyridin-3-yl)-8-oxo-6-thioxo-5,7-diazaspiro [3.4]oct-5-yl]-2-fluoro-N-methylbenzamide (also known as apalutamide or ARN-509; CAS No. 956104-408); 4-(3-(4-cyano-3-(trifluoromethyl)phenyl)-5,5-dimethyl-4-oxo-2-thioxoimidazolidin-1-yl)-2-fluoro-N-methylbenzamide (also known as MDV3100 or enzalutamide; CAS No: 915087-33-1) and RD162 (CAS No. 915087-27-3). In some embodiments, a second-generation anti-androgen binds to an AR polypeptide at or near the ligand binding site of the AR polypeptide.

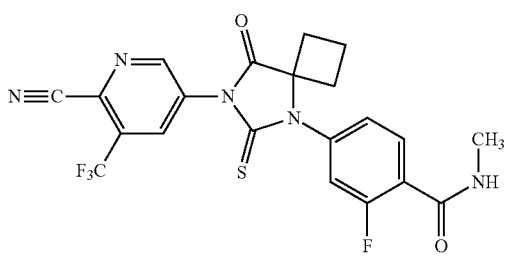 [SMILES: CNC(=O)c1ccc(N2C(=S)N(c3cnc(C#N)c(C(F)(F)F)c3)C(=O)C23CCC3)cc1F]

4-[7-(6-cyano-5-trifluoromethylpyridin-3-yl)-8-oxo-6-thioxo-5,7-diazaspiro[3.4]oct-5-yl]-2-fluoro-N-methylbenzamide (apalutamide)

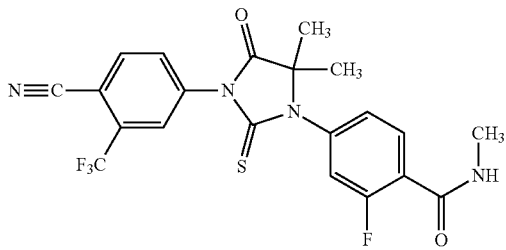 [SMILES: CNC(=O)c1ccc(N2C(=S)N(c3ccc(C#N)c(C(F)(F)F)c3)C(=O)C2(C)C)cc1F]

4-(3-(4-cyano-3-(trifluoromethyl)phenyl)-5,5-dimethyl-4-oxo-2-thioxoimidazolidin-1-yl)-2-fluoro-N-methylbenzamide (enzalutamide)

In some embodiments, an anti-androgen contemplated in the methods described herein inhibits AR nuclear translocation, such as darolutamide, DNA binding to androgen response elements, and coactivator recruitment. In some embodiments, an anti-androgen contemplated in the methods described herein exhibits no agonist activity in AR-overexpressing prostate cancer cells.

Apalutamide is a second-generation anti-androgen that binds directly to the ligand-binding domain of AR, impairing nuclear translocation, AR binding to DNA and AR target gene modulation, thereby inhibiting tumor growth and promoting apoptosis. Apalutamide binds AR with greater affinity than bicalutamide, and induces partial or complete tumor regression in non-castrate hormone-sensitive and bicalutamide-resistant human prostate cancer xenograft models (Clegg et al. *Cancer Res. Mar.* 15, 2012 72; 1494). Apalutamide lacks the partial agonist activity seen with bicalutamide in the context of AR overexpression.

Darolutamide, BAY1841788 or ODM-201, is an AR antagonist that includes two diastereomers—ORM-16497 and ORM-16555. It has activity against known AR mutants that confer resistance to other second-generation antiandrogens. Darolutamide binds to the AR with high affinity, and impairs subsequent androgen-induced nuclear translocation of AR and transcription of AR gene target. Matsubara, N., Mukai, H., Hosono, A. et al. *Cancer Chemother Pharmacol* (2017) 80: 1063.

In one aspect described herein are methods of treating non-metastatic castration-resistant prostate cancer comprising, consisting of, or consisting essentially of administering a safe and effective amount of an anti-androgen to a male human with a non-metastatic castration-resistant prostate cancer. In another aspect described herein are methods of treating a male human having non-metastatic castration-resistant prostate cancer comprising, consisting of, or consisting essentially of administering a safe and effective amount of an anti-androgen to a male human with a non-metastatic castration-resistant prostate cancer. In the following disclosure, "methods of treating non-metastatic castration-resistant prostate cancer," may alternatively be recited as "methods of treating a male human having non-metastatic castration-resistant prostate cancer." For the sake of brevity, each possible alternative is not parsed out.

In a Phase II clinical trial of male humans with high risk non-metastatic CRPC, treatment—naive metastatic CRPC and metastatic CRPC that progressed after prior treatment with abiraterone acetate (ZYTIGA) plus prednisone, oral administration of 240 mg of apalutamide on a continuous daily dosing schedule was very well tolerated and resulted in robust and durable PSA responses, as well as evidence of objective responses. A total of 25 patients with chemotherapy and abiraterone acetate-plus prednisone naive metastatic CRPC who had progressed on standard androgen deprivation therapy (treatment-naive (TN) cohort) and 21 patients who progressed after treatment with abiraterone acetate plus prednisone (PA cohort) were orally administered 240 mg of apalutamide on a continuous daily dosing schedule. The primary objective was to assess antitumor activity and PSA kinetics as defined by the Prostate Cancer Clinical Trials Working Group (PCWG2) criteria. Preliminary results demonstrated 12-week PSA declines of >50% or more from baseline in 88% and 29% of the TN and PA cohorts, respectively. The median time to PSA progression was not reached for the TN cohort during the preliminary 12-week period, and was 16 weeks in the PA cohort. In addition, the objective response rate (by RECIST) was 63%> in the TN patients presenting with measurable disease at baseline, further confirming the antitumor activity of apalutamide.

A total of 47 patients with non-metastatic CRPC were orally administered 240 mg of apalutamide on a continuous daily dosing schedule. At 12 weeks of treatment, 91% of the patients had a >50% decline in PSA as compared to baseline. At 24 weeks, the percentage of patients who had >50% decline in PSA remained at 91% and the percentage of patients who had >90%> decline in PSA was 55%>, confirming the durability of response to apalutamide. The median time to PSA progression was not reached in this observed time period.

Certain Terminology

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "androgen-deprivation therapy (ADT)" refers to the reduction of androgen levels in a prostate cancer patient to castrated levels of testosterone (<50 ng/dL). Such treatments can include orchiectomy or the use of gonadotropin-releasing hormone agonists or antagonists. ADT includes surgical castration (orchiectomy) and/or the administration of luteinizing hormone-releasing hormone ("LHRH") agonists to a human. Examples of LHRH agonists include goserelin acetate, histrelin acetate, leuprolide acetate, and triptorelin palmoate. Physicians can prescribe LHRH agonists in accordance with instructions, recommendations and practices. This may include about 0.01 mg to about 20 mg of goserelin over a period of about 28 days to about 3 months, preferably about 3.6 mg to about 10.8 mg of goserelin over a period of about 28 days to about 3 months; about 0.01 mg to about 200 mg of leuprolide over a period of about 3 days to about 12 months, preferably about 3.6 mg of leuprolide over a period of about 3 days to about 12 months; or about 0.01 mg to about 20 mg of triptorelin over a period of about 1 month, preferably about 3.75 mg of triptorelin over a period of 1 month. About 50 mg of histrelin acetate over a period of 12 months of histrelin acetate or about 50 µg per day of histrelin acetate.

The term "locally advanced prostate cancer" refers to prostate cancer where all actively cancerous cells appear to be confined to the prostate and the associated organs or neighbor organs (e.g., seminal vesicle, bladder neck, and rectal wall).

The term "high-risk localized prostate cancer" refers to locally advanced prostate cancer that has a probability of developing metastases or recurrent disease after primary therapy with curative intent. In some embodiments, high risk for development of metastases is defined as prostate specific antigen doubling time (PSADT) <20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having a high Gleason score or bulky tumor.

The term "castration-sensitive prostate cancer" refers to cancer that is responsive to androgen-deprivation therapy (ADT) either as localized disease, biochemical relapse or in the metastatic setting.

The term "metastatic castration-sensitive prostate cancer" refers to cancer that has spread (metastasized) to other areas of the body, e.g., the bone, lymph nodes or other parts of the body in a male, and that is responsive to androgen-deprivation therapy (ADT).

The term "non-metastatic castration-sensitive prostate cancer" refers to cancer that has not spread (metastasized) in a male, and that is responsive to androgen-deprivation therapy (ADT). In some embodiments, non-metastatic castration-sensitive prostate cancer is assessed with bone scan and computed tomography (CT) or magnetic resonance imaging (MM) scans.

The term "CRPC" as used herein refers to castration-resistant prostate cancer. CRPC is prostate cancer that continues to grow despite the suppression of male hormones that fuel the growth of prostate cancer cells.

The term "metastatic castration-resistant prostate cancer" refers to castration-resistant prostate cancer that has metastasized to other parts of the human body.

The term "NM-CRPC" as used herein refers to non-metastatic castration-resistant prostate cancer. In some embodiments, NM-CRPC is assessed with bone scan and computed tomography (CT) or magnetic resonance imaging (MM) scans.

The term "chemotherapy naive metastatic castration-resistant prostate cancer" refers to metastatic castration-resistant prostate cancer that has not been previously treated with a chemotherapeutic agent.

The term "post-abiraterone acetate-prednisone treated metastatic castration-resistant prostate cancer" refers to metastatic castration-resistant prostate cancer that has already been treated with abiraterone acetate.

In some embodiments, the non-metastatic castration-resistant prostate cancer is a high risk non-metastatic castration-resistant prostate cancer. The term "high risk NM-CRPC" refers to probability of a man with NM-CRPC developing metastases. In some embodiments, high risk for development of metastases is defined as prostate specific antigen doubling time (PSADT)<20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having local-regional recurrence (e.g. primary tumor bed, bladder neck, anastomotic area, pelvic lymph nodes).

The terms "co-administration" or the like, as used herein, encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g., apalutamide and a co-agent, are both administered to a patient simultaneously in the form of a single unit or single dosage form. The term "non-fixed combination" means that the active ingredients, e.g., apalutamide and a co-agent, are administered to a patient as separate units or separate dosage forms, either simultaneously, concurrently or sequentially with no specific intervening time limits, wherein such administration provides safe and effective levels of the two active ingredients in the body of the human male. The latter also applies to cocktail therapy, e.g., the administration of three or more active ingredients.

The term "FDHT-PET" refers to 18F-16P-fluoro-5a-dihydrotestosterone Positron Emission Tomography and is a technique that uses a tracer based on dihydrotestosterone, and allows for a visual assessment of ligand binding to the androgen receptor in a patient. It may be used to evaluate pharmacodynamics of an androgen receptor directed therapy [0099] The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent every day at roughly the same time each day.

The terms "treat" and "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "metastasis-free survival" or "MFS" refers to the percentage of subjects in a study who have survived without cancer spread for a defined period of time or death. MFS is usually reported as time from the beginning of enrollment, randomization or treatment in the study. MFS is reported for an individual or a study population. In the context of treatment of CRPC with an anti-androgen, an increase in the metastasis-free survival is the additional time that is observed without cancer having spread or death, whichever occurs first, as compared to treatment with placebo. In some embodiments, the increase in the metastasis-free survival is about 1 month, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months. In some embodiments, administration of a safe and effective amount of an anti-androgen provides an increase in the metastasis-free survival of a male human, optionally wherein the increase in the metastasis-free survival is relative to the mean survival rate of a population of male humans with the non-metastatic castration-resistant prostate cancer, said population having been treated with a placebo. In some embodiments, metastasis-free survival refers to the time from randomization to the time of first evidence of BICR-confirmed bone or soft tissue distant metastasis or death due to any cause, whichever occurs first.

The term "time to metastasis" is the time from randomization to the time of the scan that shows first evidence of BICR-confirmed radiographically detectable bone or soft tissue distant metastasis. In some embodiments, administration of a safe and effective amount of an anti-androgen provides improved anti-tumor activity as measured by time to metastasis (TTM).

The term "progression-free survival" is based on RECIST v1.1 and is defined as follows: For subjects with at least one measurable lesion, progressive disease is defined as at least a 20% increase in the sum of diameters of target lesions taking as reference the smallest sum on study (this includes the baseline sum if that is the smallest on study). In addition to the relative increase of 20%, the sum must also demonstrate an absolute increase of at least 5 mm. Furthermore, the appearance of one or more new lesions is also considered progression. For subjects with only non-measurable disease observed on CT or MM scans, unequivocal progression (representative of overall disease status change) or the appearance of one or more new lesions was considered progression. For new bone lesions detected on bone scans, a second imaging modality (e.g., CT or MM) was required to confirm progression. In some embodiments, administration of a safe and effective amount of an anti-androgen provides improved anti-tumor activity as measured by progression-free survival rate.

The term "time to symptomatic progression" is defined as the time from randomization to documentation in the CRF of any of the following (whichever occurs earlier): (1) development of a skeletal-related event (SRE): pathologic fracture, spinal cord compression, or need for surgical intervention or radiation therapy to the bone; (2) pain progression or worsening of disease-related symptoms requiring initiation of a new systemic anti-cancer therapy; or (3) development of clinically significant symptoms due to loco-regional tumor progression requiring surgical intervention or radiation therapy. In some embodiments, administration of a safe and effective amount of an anti-androgen provides improved anti-tumor activity as measured by time to symptomatic progression.

The term "overall survival" is defined as the time from randomization to the date of death due to any cause. Survival data for subjects who are alive at the time of the analysis was to be censored on the last known date that they were alive. In addition, for subjects with no post-baseline information survival, data was to be censored on the date of randomization; for subjects who are lost to follow-up or who withdraw consent, data is censored on the last known date that they were alive. In some embodiments, administration of a safe and effective amount of an anti-androgen provides improved anti-tumor activity as measured by overall survival.

The term "time to initiation of cytotoxic chemotherapy" is defined as the time from randomization to documentation of a new cytotoxic chemotherapy being administered to the subject (e.g., survival follow-up CRF). Time to initiation of cytotoxic chemotherapy for subjects who do not start a cytotoxic chemotherapy is censored on the date of last contact. In some embodiments, administration of a safe and effective amount of an anti-androgen provides improved anti-tumor activity as measured by time to cytotoxic chemotherapy.

The term "progression-free survival with the first subsequent therapy (PFS2) is defined as the time from randomization to investigator-assessed disease progression (PSA, radiographic, symptomatic, or any combination) during first subsequent anti-cancer therapy or death (any cause) prior to the start of the second subsequent anti-cancer therapy, whichever occurs first. Progression data for subjects without documented progression after subsequent therapy is censored at the last date known to be progression-free or date of death. In some embodiments, administration of a safe and effective amount of an anti-androgen provides improved anti-tumor activity as measured progression-free survival with the first subsequent therapy.

Prostate specific antigen response and time to PSA progression is assessed at the time of the primary analysis of MFS according to the Prostate Cancer Working Group (PCWG2) criteria. The time to PSA progression is calculated as the time from randomization to the time when the criteria for PSA progression according to PCWG2 are met.

The term "placebo" as used herein means administration of a pharmaceutical composition that does not include a second-generation anti-androgen. In the context of treatment of CRPC, men that are administered an anti-androgen or placebo will need to continue to maintain castrated levels of testosterone by either co-administration of a GnRH agonist/antagonist or orchiectomy.

The term "survival benefit" as used herein means an increase in survival of the patient from time of randomization on the trial of administered drug to death. In some embodiments, the survival benefit is about 1, about 2, about 3, about 4, about 5, about 6, about 7, about 8, about 9, about 10, about 15, about 20, about 25, about 30, about 35, about 40, about 45, about 50, about 55, about 60, about 80, about 100 months or greater than 100 months.

The term "delay in symptoms related to disease progression" as used herein means an increase in time in the development of symptoms such as pain, urinary obstruction and quality of life considerations from the time of randomization on the trial of administered drug.

The term 'randomization' as it refers to a clinical trial refers to the time when the patient is confirmed eligible for the clinical trial and gets assigned to a treatment arm.

The terms "kit" and "article of manufacture" are used as synonyms.

The term "subject" and "patient" and "human" are used interchangeably.

The term, "drug product" or "approved drug product" is product that contains an active pharmaceutical ingredient that has been approved for marketing for at least one indication by a governmental authority, e.g., the Food and Drug Administration or the similar authority in other countries.

The term "Reference Listed Drug (RLD)" is a drug product to which new generic versions are compared to show that they are bioequivalent. 21 CFR 314.3(b)) It is also a medicinal product that has been granted marketing authorization by a Member State of the European Union or by the Commission on the basis of a completed dossier, i.e., with the submission of quality, pre-clinical and clinical data in accordance with Articles 8(3), 10a, 10b or 10c of Directive 2001/83/EC and to which the application for marketing authorization for a generic/hybrid medicinal product refers, by demonstration of bioequivalence, usually through the submission of the appropriate bioavailability studies.

In the United States, a company seeking approval to market a generic equivalent must refer to the RLD in its Abbreviated New Drug Application (ANDA). For example, an ANDA applicant relies on the FDA's finding that a previously approved drug product, i.e., the RLD, is safe and effective, and must demonstrate, among other things, that the proposed generic drug product is the same as the RLD in certain ways. Specifically, with limited exceptions, a drug product for which an ANDA is submitted must have, among other things, the same active ingredient(s), conditions of use, route of administration, dosage form, strength, and (with certain permissible differences) labeling as the RLD. The RLD is the listed drug to which the ANDA applicant must show its proposed ANDA drug product is the same with respect to active ingredient(s), dosage form, route of administration, strength, labeling, and conditions of use, among other characteristics. In the electronic Orange Book, there will is a column for RLDs and a column for reference standards. In the printed version of the Orange Book, the RLDs and reference standards are identified by specific symbol. For an ANDA based on an approved suitability petition (a petitioned ANDA), the reference listed drug generally is the listed drug referenced in the approved suitability petition.

A reference standard is the drug product selected by FDA that an applicant seeking approval of an ANDA must use in conducting an in vivo bioequivalence study required for approval. FDA generally selects a single reference standard that ANDA applicants must use in in vivo bioequivalence testing. Ordinarily, FDA will select the reference listed drug as the reference standard. However, in some instances (e.g., where the reference listed drug has been withdrawn from sale and FDA has determined it was not withdrawn for reasons of safety or effectiveness, and FDA selects an ANDA as the reference standard), the reference listed drug and the reference standard may be different.\

FDA identifies reference listed drugs in the Prescription Drug Product, OTC Drug Product, and Discontinued Drug Product Lists. Listed drugs identified as reference listed drugs represent drug products upon which an applicant can rely in seeking approval of an ANDA. FDA intends to update periodically the reference listed drugs identified in the Prescription Drug Product, OTC Drug Product, and Discontinued Drug Product Lists, as appropriate.

FDA also identifies reference standards in the Prescription Drug Product and OTC Drug Product Lists. Listed drugs identified as reference standards represent the FDA's best judgment at this time as to the appropriate comparator for purposes of conducting any in vivo bioequivalence studies required for approval.

In some instances when FDA has not designated a listed drug as a reference listed drug, such listed drug may be shielded from generic competition. If FDA has not designated a reference listed drug for a drug product the applicant intends to duplicate, the potential applicant may ask FDA to designate a reference listed drug for that drug product.

FDA may, on its own initiative, select a new reference standard when doing so will help to ensure that applications for generic drugs may be submitted and evaluated, e.g., in the event that the listed drug currently selected as the reference standard has been withdrawn from sale for other than safety and efficacy reasons.

In Europe, Applicants identify in the application form for its generic/hybrid medicinal product, which is the same as a ANDA or sNDA drug product, the reference medicinal product (product name, strength, pharmaceutical form, MAH, first authorization, Member State/Community), which is synonymous with a RLD, as follows:

1. The medicinal product that is or has been authorized in the EEA, used as the basis for demonstrating that the data protection period defined in the European pharmaceutical legislation has expired. This reference medicinal product, identified for the purpose of calculating expiry of the period of data protection, may be for a different strength, pharmaceutical form, administration route or presentation than the generic/hybrid medicinal product.

2. The medicinal product, the dossier of which is cross-referred to in the generic/hybrid application (product name, strength, pharmaceutical form, MAH, marketing authorization number). This reference medicinal product may have been authorized through separate procedures and under a different name than the reference medicinal product identified for the purpose of calculating expiry of the period of data protection. The product information of this reference medicinal product will, in principle, serve as the basis for the product information claimed for the generic/hybrid medicinal product.

3. The medicinal product (product name, strength, pharmaceutical form, MAH, Member State of source) used for the bioequivalence study(ies) (where applicable).

The different abbreviated approval pathways for drug products under the FD&C Act the abbreviated approval pathways described in section 505(j) and 505(b)(2) of the FD&C Act (21 U.S.C. 355(j) and 21 U.S.C. 23 355(b)(2), respectively).

According to the FDA (www.fda.gov/downloads/Drugs/GuidanceComplianceRegulatoryInformation/Guidances/UCM579751.pdf), the contents of which is incorporated herein by reference), NDAs and ANDAs can be divided into the following four categories:

(1) A "stand-alone NDA" is an application submitted under section 505(b)(1) and approved under section 505(c) of the FD&C Act that contains full reports of investigations of safety and effectiveness that were conducted by or for the applicant or for which the applicant has a right of reference or use.

(2) A 505(b)(2) application is an NDA submitted under section 505(b)(1) and approved under section 505(c) of the FD&C Act that contains full reports of investigations of safety and effectiveness, where at least some of the information required for approval comes from studies not conducted by or for the applicant and for which the applicant has not obtained a right of reference or use.

(3) An ANDA is an application for a duplicate of a previously approved drug product that was submitted and approved under section 505(j) of the FD&C Act. An ANDA relies on FDA's finding that the previously approved drug product, i.e., the reference listed drug (RLD), is safe and effective. An ANDA generally must contain information to show that the proposed generic product (a) is the same as the RLD with respect to the active ingredient(s), conditions of use, route of administration, dosage form, strength, and labeling (with certain permissible differences) and (b) is bioequivalent to the RLD. An ANDA may not be submitted if studies are necessary to establish the safety and effectiveness of the proposed product.

(4) A petitioned ANDA is a type of ANDA for a drug product that differs from the RLD in its dosage form, route of administration, strength, or active ingredient (in a product with more than one active ingredient) and for which FDA has determined, in response to a petition submitted under section 505(j)(2)(C) of the FD&C Act (suitability petition), that studies are not necessary to establish the safety and effectiveness of the proposed drug product.

A scientific premise underlying the Hatch-Waxman Amendments is that a drug product approved in an ANDA under section 505(j) of the FD&C Act is presumed to be therapeutically equivalent to its RLD. Products classified as therapeutically equivalent can be substituted with the full expectation that the substituted product will produce the same clinical effect and safety profile as the prescribed product when administered to patients under the conditions specified in the labeling. In contrast to an ANDA, a 505(b)(2) application allows greater flexibility as to the characteristics of the proposed product. A 505(b)(2) application will not necessarily be rated therapeutically equivalent to the listed drug it references upon approval.

The term "therapeutically equivalent to a reference listed drug" is means that the drug product is a generic equivalent, i.e., pharmaceutical equivalents, of the reference listed drug product and, as such, is rated an AB therapeutic equivalent to the reference listed drug product by the FDA whereby actual or potential bioequivalence problems have been resolved with adequate in vivo and/or in vitro evidence supporting bioequivalence.

"Pharmaceutical equivalents" means drug products in identical dosage forms and route(s) of administration that contain identical amounts of the identical active drug ingredient as the reference listed drug.

FDA classifies as therapeutically equivalent those products that meet the following general criteria: (1) they are approved as safe and effective; (2) they are pharmaceutical equivalents in that they (a) contain identical amounts of the same active drug ingredient in the same dosage form and route of administration, and (b) meet compendial or other applicable standards of strength, quality, purity, and identity; (3) they are bioequivalent in that (a) they do not present a known or potential bioequivalence problem, and they meet an acceptable in vitro standard, or (b) if they do present such a known or potential problem, they are shown to meet an appropriate bioequivalence standard; (4) they are adequately labeled; and (5) they are manufactured in compliance with Current Good Manufacturing Practice regulations The term "bioequivalent" or "bioequivalence" is the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Section 505 (j)(8)(B) of the FD&C Act describes one set of conditions under which a test and reference listed drug shall be considered bioequivalent:

the rate and extent of absorption of the [test] drug do not show a significant difference from the rate and extent of absorption of the [reference] drug when administered at the same molar dose of the therapeutic ingredient under similar experimental conditions in either a single dose or multiple doses; or the extent of absorption of the [test] drug does not show a significant difference from the extent of absorption of the [reference] drug when administered at the same molar dose of the therapeutic ingredient under similar experimental conditions in either a single dose or multiple doses and the difference from the [reference] drug in the rate of absorption of the drug is intentional, is reflected in its proposed labeling, is not essential to the attainment of effective body drug concentrations on chronic use, and is considered medically insignificant for the drug.

Where these above methods are not applicable (e.g., for drug products that are not intended to be absorbed into the bloodstream), other scientifically valid in vivo or in vitro test methods to demonstrate bioequivalence may be appropriate.

For example, bioequivalence may sometimes be demonstrated using an in vitro bioequivalence standard, especially when such an in vitro test has been correlated with human in vivo bioavailability data. In other situations, bioequivalence may sometimes be demonstrated through comparative clinical trials or pharmacodynamic studies.

The terms "sale" or "selling" means transferring a drug product, e.g., a pharmaceutical composition or an oral dosage form, from a seller to a buyer.

The term "offering for sale" means the proposal of a sale by a seller to a buyer for a drug product, e.g., a pharmaceutical composition and an oral dosage form.

Routes of Administration and Pharmaceutical Compositions

Therapeutic agents described herein are administered in any suitable manner or suitable formulation. Suitable routes of administration of the therapeutic agents include, but are not limited to, oral and parenteral (e.g., intravenous, subcutaneous, intramuscular). All formulations are in dosages suitable for administration to a human. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

The term "safe and effective amount" refers to an amount of an active ingredient that elicits the desired biological or medicinal response in a subject's biological system without the risks outweighing the benefits of such response in accordance with the Federal Food, Drug, and Cosmetic Act, as amended (secs. 201-902, 52 Stat. 1040 et seq., as amended; 21 U.S.C. §§ 321-392). Safety is often measured by toxicity testing to determine the highest tolerable dose or the optimal dose of an active pharmaceutical ingredient needed to achieve the desired benefit. Studies that look at safety also seek to identify any potential adverse effects that may result from exposure to the drug. Efficacy is often measured by determining whether an active pharmaceutical ingredient demonstrates a health benefit over a placebo or other intervention when tested in an appropriate situation, such as a tightly controlled clinical trial.

The term "acceptable" with respect to a formulation, composition or ingredient, as used herein, means that the beneficial effects of that formulation, composition or ingredient on the general health of the male human being treated substantially outweigh its detrimental effects, to the extent any exist.

In some embodiments, administration of a safe and effective amount of the anti-androgen results in no more than a grade 2 adverse event. In other embodiments, administration of a safe and effective amount of anti-androgen results in no more than a grade 3 adverse event. In other embodiments, administration of a safe and effective amount of anti-androgen results in no more than a grade 4 adverse event.

In some embodiments, the anti-androgen is present in a solid oral dosage form. In some embodiments, the anti-androgen is formulated as a tablet. In some embodiments, the anti-androgen is apalutamide. In some embodiments, the anti-androgen is enzalutamide. Solid oral dosage forms containing either apalutamide or enzalutamide may be provided as soft gel capsules as disclosed in WO2014113260 and CN104857157, each of which is incorporated herein by reference, or as tablets as disclosed in WO2016090098, WO2016090101, WO2016090105, and WO2014043208, each of which is incorporated herein by reference. Techniques suitable for preparing solid oral dosage forms of the present invention are described in Remington's Pharmaceutical Sciences, 18th edition, edited by AR. Gennaro, 1990, Chapter 89, and in Remington—The Science, and Practice of Pharmacy, 21st edition, 2005, Chapter 45.

To prepare the pharmaceutical compositions of this invention, the active pharmaceutical ingredient is intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

In solid oral preparations such as, for example, dry powders for reconstitution or inhalation, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, dry powders for reconstitution or inhalation, granules, lozenges, sterile solutions or suspensions, metered aerosol or liquid sprays, drops, or suppositories for administration by oral, intranasal, sublingual, intraocular, transdermal, rectal, vaginal, dry powder inhaler or other inhalation or insufflation means.

These formulations are manufactured by conventional formulation techniques. For preparing solid pharmaceutical compositions such as tablets, the principal active ingredient is mixed with a pharmaceutical carrier, e.g., conventional tableting ingredients such as diluents, binders, adhesives, disintegrants, lubricants, antiadherents, and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL silica available from Cabot, SYLOID silica available from W. R. Grace/Davison, and AEROSIL silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Binders suitable for use in the pharmaceutical compositions provided herein include, but are not limited to, starches, cellulose, and its derivatives (e.g., ethylcellulose, cellulose acetate, carboxymethyl cellulose calcium, sodium carboxymethyl cellulose, methylcellulose, hydroxypropyl methylcellulose), polyviny 1 pyrrolidone, and mixtures thereof.

Examples of fillers suitable for use in the pharmaceutical compositions provided herein include, but are not limited to, microcrystalline cellulose, powdered cellulose, mannitol, lactose, calcium phosphate, starch, pre gelatinized starch, and mixtures thereof.

The binder or filler in pharmaceutical compositions is typically present in from about 50 to about 99 weight percent of the pharmaceutical composition or dosage form.

Disintegrants can be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant. Disintegrants that can be used in the pharmaceutical compositions provided herein include, but are not limited to, croscarmellose sodium, crospovidone, sodium starch glycolate, potato or tapioca starch, pre gelatinized starch, other starches, other celluloses, gums, and mixtures thereof.

Lubricants that can be used in the pharmaceutical compositions provided herein include, but are not limited to, calcium stearate, magnesium stearate, mineral oil, light mineral oil, glycerin, sorbitol, polyethylene glycol, other glycols, stearic acid, sodium lauryl sulfate, sodium stearyl fumarate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Lubricants are typically used in an amount of less than about 1 weight percent of the pharmaceutical compositions or dosage forms into which they are incorporated.

Compressed tablet formulations may optionally be film-coated to provide color, light protection, and/or taste-masking. Tablets may also be coated so as to modulate the onset, and/or rate of release in the gastrointestinal tract, so as to optimize or maximize the biological exposure of the patient to the API.

Hard capsule formulations may be produced by filling a blend or granulation of apalutamide or enzalutamide into shells consisting of, for example, gelatin, or hypromellose.

Soft gel capsule formulations may be produced.

Pharmaceutical compositions intended for oral use may be prepared from the solid dispersion formulations, and blended materials described above in accordance with the methods described herein, and other methods known to the art for the manufacture of pharmaceutical compositions. Such compositions may further contain one or more agents selected from the group consisting of sweetening agents, flavoring agents, coloring agents, and preserving agents in order to provide pharmaceutically elegant and palatable preparations.

Tablets may contain the active ingredient in admixture with non-toxic pharmaceutically acceptable excipients that are suitable for the manufacture of tablets. These excipients may be for example, inert diluents, granulating, and disintegrating agents, binding agents, glidants, lubricating agents, and antioxidants, for example, propyl gallate, butylated hydroxyanisole, and butylated hydroxy toluene. The tablets may be uncoated or they may be film coated to modify their appearance or may be coated with a functional coat to delay disintegration, and absorption in the gastrointestinal tract, and thereby provide a sustained action over a longer period.

Compositions for oral use may also be presented as capsules (e.g., hard gelatin) wherein the active ingredient is mixed with an inert solid diluent, for example, calcium carbonate, calcium phosphate or starch, or as soft gelatin capsules wherein the active ingredient is mixed with liquids or semisolids, for example, peanut oil, liquid paraffin, fractionated glycerides, surfactants or olive oil. Aqueous suspensions contain the active materials in mixture with excipients suitable for the manufacture of aqueous suspensions. Dispersible powders and granules suitable for preparation of an aqueous suspension by the addition of water provide the active ingredient in mixture with a dispersing or wetting agent, suspending agent, and one or more preservatives. In certain embodiments of the invention, the pharmaceutical compositions of the invention include a diluent system, disintegrant, salt, lubricant, glidant, and filmcoat, at concentrations of from about 3% w/w to about 58% w/w, from about 4% w/w to about 20% w/w, from about 4% w/w to about 20% w/w, from about 0.5% w/w to about 4% w/w, from about 0% w/w to about 2% w/w, and from about 1% w/w to about 5% w/w respectively, or at from about 18% w/w to about 40% w/w, from about 7% w/w to about 15% w/w, from about 7% w/w to about 18% w/w, from about 1.0% w/w to about 3.0%, from about 0.1% w/w to about 1.0% w/w, and from about 2.0% w/w to about 4.0% w/w, respectively. In certain embodiments, the solid dispersion formulations are blended with a diluent, one or more disintegrating agents, lubricants, and glidants. An exemplary blended composition or oral dosage form includes mannitol, microcrystalline cellulose, croscarmellose sodium, sodium chloride, colloidal silica, sodium stearyl fumarate, and magnesium stearate.

The disintegrant may be present in a concentration from about 4% w/w to about 20% w/w or from about 7% w/w to about 15% w/w. A salt may be also present, which may be sodium chloride, potassium chloride or a combination thereof. The combination of salts and disintegrant is present at a concentration from about 5% w/w to about 35% w/w of the final pharmaceutical composition.

In certain embodiments, inactive ingredients of the core tablet are: colloidal anhydrous silica, croscarmellose sodium, hydroxypropyl methylcellulose-acetate succinate, magnesium stearate, microcrystalline cellulose, and silicified microcrystalline cellulose. In other embodiments, the tablets are finished with a film-coating consisting of the following excipients: iron oxide black, iron oxide yellow, polyethylene glycol, polyvinyl alcohol, talc, and titanium dioxide In other embodiments, a single unit dosage of the pharmaceutical composition comprises, consists of, or consists essentially of about 60 mg of apalutamide. In some embodiments, multiple doses of the single unit dosage pharmaceutical composition comprising, consisting of, or consisting essentially of about 60 mg of apalutamide, e.g., 4 multiple or individual unit dosage forms, are administered to the human. The total daily dose of apalutamide may be about 240 mg per day.

In some embodiments, a single unit dosage of the pharmaceutical composition comprises, consists of, or consists essentially of about 40 mg of enzalutamide. In some embodiments, multiple doses of the single unit dosage pharmaceutical composition comprising, consisting of, or consisting essentially of about 40 mg of enzalutamide, e.g., 4 multiple or individual unit dosage forms, are administered to the human. The total daily dose of enzalutamide may be about 160 mg per day.

In still further embodiments, a single unit dosage of the pharmaceutical composition comprises, consists of, or consists essentially of about 300 mg of darolutamide. In some embodiments, multiple doses of the single unit dosage pharmaceutical composition comprising, consisting of, or consisting essentially of about 300 mg of enzalutamide, e.g., 2 multiple or individual unit dosage forms, are administered to the human. The total daily dose of darolutamide may be about 1200 mg per day.

All formulations for oral administration are in dosage form suitable for such administration.

Methods of Dosing and Treatment Regimens

In one aspect, described herein are methods of treating non-metastatic castration-resistant prostate cancer comprising, consisting of, or consisting essentially of administering a safe and effective amount of an anti-androgen to a male human with a non-metastatic castration-resistant prostate cancer, wherein the apalutamide or enzalutamide is administered orally. In some embodiments, the anti-androgen is administered daily. In some embodiments, the anti-androgen is administered twice-a-day. In some embodiments, the anti-androgen is administered three times a day. In some embodiments, the anti-androgen is administered four times a day. In some embodiments, the apalutamide is administered every other day. In some embodiments, the anti-androgen is administered weekly. In some embodiments, the anti-androgen is administered twice a week. In some embodiments, the anti-androgen is administered every other week. In some embodiments, the anti-androgen is administered orally on a continuous daily dosage schedule.

In one embodiment, the desired dose is conveniently presented in a single dose or in divided doses administered simultaneously (or over a short period of time) or at appropriate intervals, for example as two, three, four or more sub-doses per day. In some embodiments, the anti-androgen is conveniently presented in divided doses that are administered simultaneously (or over a short period of time) once a day. In some embodiments, the anti-androgen is conveniently presented in divided doses that are administered in equal portions twice-a-day. In some embodiments, the anti-androgen is conveniently presented in divided doses that are administered in equal portions three times a day. In some embodiments, the anti-androgen is conveniently presented in divided doses that are administered in equal portions four times a day.

In some embodiments, the anti-androgen is a second-generation anti-androgen. In certain embodiments, the anti-androgen is enzalutamide or apalutamide. In some embodiments, the anti-androgen is enzalutamide. In some embodiments, the anti-androgen is apalutamide. In some embodiments, the anti-androgen is darolutamide.

In general, doses of apalutamide employed for treatment of the diseases or conditions described herein in humans are typically in the range of 10 mg to 1000 mg per day. In some embodiments, apalutamide, enzalutamide or darolutamide is administered orally to the human at a dose of about 30 mg per day to about 1200 mg per day. In some embodiments, apalutamide is administered orally to the human at a dose of about 30 mg per day to about 600 mg per day. In some embodiments, apalutamide is administered orally to the human at a dose of about 30 mg per day, about 60 mg per day, about 90 mg per day, about 120 mg per day, about 160 mg per day, about 180 mg per day, about 240 mg per day, about 300 mg per day, about 390 mg per day, about 480 mg per day, about 600 mg per day, about 780 mg per day, about 960 mg per day, or about 1200 mg per day.

In some embodiments, apalutamide is administered orally to the human at a dose of about 240 mg per day. In some embodiments, greater than 240 mg per day of apalutamide is administered to the human. In some embodiments, the apalutamide is administered orally to the human at a dose of about 60 mg four times per day. In some embodiments, apalutamide is administered orally to the human on a continuous daily dosing schedule.

In some embodiments, the enzalutamide is administered orally at a dose of about 160 mg per day. In some embodiments, greater than 160 mg per day of enzalutamide is administered.

In some embodiments, the darolutamide is administered orally at a dose of about 1200 mg per day. In some embodiments, greater than 1200 mg per day of darolutamide is administered.

In certain embodiments wherein improvement in the status of the disease or condition in the human is not observed, the daily dose of anti-androgen is increased. In some embodiments, a once-a-day dosing schedule is changed to a twice-a-day dosing schedule. In some embodiments, a three times a day dosing schedule is employed to increase the amount of anti-androgen that is administered.

In some embodiments, the amount of anti-androgen that is given to the human varies depending upon factors such as, but not limited to, condition and severity of the disease or condition, and the identity (e.g., weight) of the human, and the particular additional therapeutic agents that are administered (if applicable).

In certain embodiments, the dose of antiandrogen, e.g., apalutamide, enzalutamide, or darolutamide is reduced when co-administered with one or more of:
 (a) a CYP2C8 inhibitor, preferably gemfibrozil or clopidogrel; or
 (b) a CYP3A4 inhibitor, preferably ketoconazole or ritonavir.

In some embodiments, the apalutamide is not co-administered with:
 (a) medications that are primarily metabolized by CYP3A4, preferably darunavir, felodipine, midazolam or simvastatin;
 (b) medications that are primarily metabolized by CYP2C19, preferably diazepam or omeprazole;
 (c) medications that are primarily metabolized by CYP2C9, preferably warfarin or phenytoin; or
 (d) medications that are substrates of UGT, preferably levothyroxine or valproic acid.

In further embodiments, the apalutamide is not co-administered with:
 (a) medications that are P-gp substrates, preferably fexofenadine, colchicine, dabigatran etexilate or digoxin; or
 (b) BCRP/OATP1B1 substrates, preferably lapatinib, methotrexate, rosuvastatin, or repaglinide.

In further embodiments, a male human having said non-metastatic castration-resistant prostate cancer has received at least one prior therapy for the treatment of cancer, optionally wherein the prior therapy for the treatment of cancer is bicalutamine or flutamide. In still further embodiments, a male human having said non-metastatic castration-resistant prostate cancer is treatment naïve.

Kits/Articles of Manufacture

For use in the methods of use described herein, kits and articles of manufacture are also described. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert.

In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Methods of Sale

In another aspect, described herein are methods of selling an anti-androgen comprising, consisting of, or consisting essentially of placing the anti-androgen into the stream of commerce wherein said anti-androgen includes a package insert that contains instructions for safely and effectively treating prostate cancer using the anti-androgen. In some embodiments, the anti-androgen is a second-generation anti-androgen. In some embodiments, the anti-androgen is darolutamide, enzalutamide or apalutamide. In some embodiments, the anti-androgen is darolutamide. In some embodiments, the anti-androgen is enzalutamide. In some embodiments, the anti-androgen is apalutamide.

In further aspects, described herein are methods of selling a pharmaceutical composition containing anti-androgen comprising, consisting of, or consisting essentially of placing such pharmaceutical composition into the stream of commerce wherein such pharmaceutical composition includes a package insert that contains instructions for safely and effectively treating prostate cancer using anti-androgen. In some embodiments, the anti-androgen is a second-generation anti-androgen. In some embodiments, the anti-androgen is enzalutamide or apalutamide. In some embodiments, the anti-androgen is enzalutamide. In some embodiments, the anti-androgen is apalutamide.

In still further aspects, described herein are methods of offering for sale anti-androgen comprising, consisting of, or consisting essentially of offering to place the anti-androgen into the stream of commerce wherein said anti-androgen includes a package insert that contains instructions for safely and effectively treating prostate cancer using the anti-androgen. In some embodiments, the anti-androgen is a second-generation anti-androgen. In some embodiments, the anti-androgen is darolutamide, enzalutamide or apalutamide. In some embodiments the antiandrogen is darolutamide. In some embodiments, the anti-androgen is enzalutamide In some embodiments, the anti-androgen is apalutamide

EXAMPLES

These examples are provided for illustrative purposes only and not to limit the scope of the claims provided herein.

Example 1: Pre-Clinical Development

ARN 509 (apalutamide) is a next-generation anti-androgen that binds directly to the ligand-binding domain of androgen receptor (AR), impairing nuclear translocation and DNA binding. The mechanism of action of apalutamide is through antagonism of androgen action and inhibition of AR nuclear translocation and DNA binding to androgen response elements, a mechanism that is distinct from the first generation anti-androgen, bicalutamide. Unlike bicalutamide, apalutamide shows no significant agonist properties in an in vitro model of CRPC (e.g., AR-over-expressing prostate cancer cells; LNCaP/AR cells). Gene transcription of the androgen-driven genes, PSA and TMPRSS2, is inhibited by apalutamide and results in concentration-dependent reduction of these protein levels in vitro. Apalutamide was also shown to reduce proliferation of CRPC cells as well as increase apoptosis and necrosis in vivo. These effects are supported by the anti-tumor activity of apalutamide observed in murine tumor models of CRPC. In these models, apalutamide showed dose-dependent tumor growth inhibition and tumor regression that were superior to bicalutamide. FIG. 1 depicts the percent change in tumor volume and plasma concentrations (filled circles above waterfall plot) of bicalutamide and apalutamide on Day 28.

Apalutamide is a low clearance molecule with a moderate volume of distribution and high bioavailability (when dosed with a lipid-based formulation). Apalutamide was found to have a very low turnover when incubated for up to 120 minutes with rat, dog, and human liver S9 fraction and liver microsomes. The primary in vivo metabolites were formed by N-demethylation and amide hydrolysis in the rat and dog. In vitro, CYP3A4 may be partially involved in the metabolism of apalutamide.

Apalutamide and its primary metabolite ARN000308 (M3) are inducers of human CYP2B6 and CYP3A4 in hepatocytes at concentrations up to 30 µM. Apalutamide is a moderately potent inhibitor of human cytochrome P450 isoform CYP2C8 ($IC_{50}$=13.9 but a weak inhibitor of the other major isoforms ($IC_{50}$>25 µM); M3 is also a weak inhibitor of CYP major isoforms ($IC_{50}$>25 µM).

Four metabolites have been identified with different proportions between species. All four were assessed for their on-target effects against the androgen receptor. Metabolite M1 was found to be essentially inactive as an AR antagonist, while metabolites M2 and M4 were approximately 30-fold less potent against AR than apalutamide. Metabolite M3 was the most potent AR antagonist, but was still 3-fold less potent than apalutamide. Metabolite M3 is considered the predominant metabolite, with a longer elimination half-life than apalutamide.

Single-dose and repeat-dose toxicology studies up to 13 weeks of dosing have been conducted in male Sprague Dawley (SD) rats and male Beagle dogs (repeat-dose studies only). Acute administration of apalutamide at 1,000 mg/kg was well tolerated in SD rats, with no morbidity, mortality or significant effects on body weight or serum chemistry markers.

In repeat-dose toxicology studies, apalutamide was well tolerated at doses up to 100 mg/kg/day in the 13-weeks study in SD rats and 10 mg/kg/day in Beagle dogs. In male SD rats, lethality was observed at doses of 150 mg/kg/day and greater. The morbidity/mortality observed at these doses occurred within the first 5 days of dosing; however, animals that did survive at these higher doses, appeared to develop a tolerance for the test article with extended exposure. Clinical signs observed in the moribund animals were pilo-erection, hypothermia, breathing abnormalities, dehydration, and decreased activity. The cause of the morbidity/mortality in male rats could not be determined by pathologic examination. Key clinical pathology changes at doses of 150 mg/kg/day or greater included significant increases in cholesterol (greater than 200% from controls), decreases in erythrocytes, hemoglobin and hematocrit, and increases in reticulocytes, platelets, leukocytes, lymphocytes, basophils, and aPTT. The increase in cholesterol is attributed to the anti-androgen activity of apalutamide and is believed to be responsible for the stated hematologic changes. Examination of red blood cell morphology revealed changes that were consistent with excess cholesterol being transferred to the outer membrane of the erythrocytes, resulting in a mild hemolytic anemia. Pharmacologic effects were also observed in the male accessory sex organs (epididymides, prostate, seminal vesicles and to a lesser degree, the testes) at apalutamide doses as low as 50 mg/kg/day. Other target organs in the rat that were observed at apalutamide doses of 150 mg/kg/day or higher included adrenals (also at 50 mg/kg/day), liver, pituitary, thyroid, spleen, salivary glands, mammary gland, and stomach. With the exception of the salivary glands and stomach, the effects on those organs are also believed to be due to the anti-androgen effect of apalutamide and in many cases are specific to the physiology of the rat.

Once daily oral gavage dosing of apalutamide for 13 weeks was well tolerated in male rats up to 100 mg/kg/day, i.e. the highest dose tested. Pharmacologic changes characteristic of anti-androgen compounds were noted in the adrenal gland, pituitary gland, spleen, mammary gland, seminal vesicles, testes, prostate, and epididymides, while changes in the spleen and bone marrow correlated with a mild regenerative anemia. The 100 mg/kg/day dose level was considered to be the no observed adverse effect level (NOAEL) and was associated with steady-state (Day 91) plasma $C_{max}$ and $AUC_{0-24\,h}$ values of 30.1 µg/mL and 521 µg·h/mL, respectively, for the parent compound.

In male Beagle dogs, seizures necessitating humane euthanasia occurred at apalutamide doses of 25 mg/kg/day and greater, 7 to 14 days after dosing was initiated. Daily administration of 25 mg/kg/day of apalutamide resulted in tremors and seizures in 3 of 8 animals after 1 week of dosing. The average apalutamide concentration at the time of first observation of central nervous system (CNS) toxicity was determined to be 30.2 µg/mL, which was about 4-fold higher than the mean apalutamide steady-state $C_{max}$ (7.55 µg/mL) at the Phase 3 dose of 240 mg/day measured during repeated dosing in subjects with CRPC. It is likely that the convulsive seizures observed in dogs at very high doses are the result of apalutamide's functional antagonism of the GABAA receptor. This is similar to what has been observed with other second generation AR antagonists. The 10 mg/kg/day dose was considered to be the NOAEL in the 28-day study, and was associated with an apalutamide $C_{max}$ of 13.2 µg/mL and an $AUC_{0-24}$ of 290 µg·h/mL. Other clinical pathology and target organ changes were limited to increases in cholesterol (up to 50% compared to controls) and effects on the epididymides, prostate and testes at all doses tested and attributed to the anti-androgen effect of apalutamide.

Once daily oral capsule administration of apalutamide for 13 weeks was well tolerated in male dogs up to 10 mg/kg/day, i.e. the highest dose tested. Gross and microscopic pathology changes and organ weight changes characteristic of anti-androgen compounds were noted in the pituitary gland, prostate, testes, and epididymides; these changes were reversible and were attributable to the expected pharmacologic effect of apalutamide. Based upon the lower body weight performance in the group receiving 10 mg/kg/day, the 5 mg/kg/day dose was considered to be the NOAEL. Corresponding steady-state (Day 91) plasma $C_{max}$ and $AUC_{0-24}h$ values were 10.3 µg/mL and 202 µg·h/mL, respectively, for the parent compound.

Figure 2:
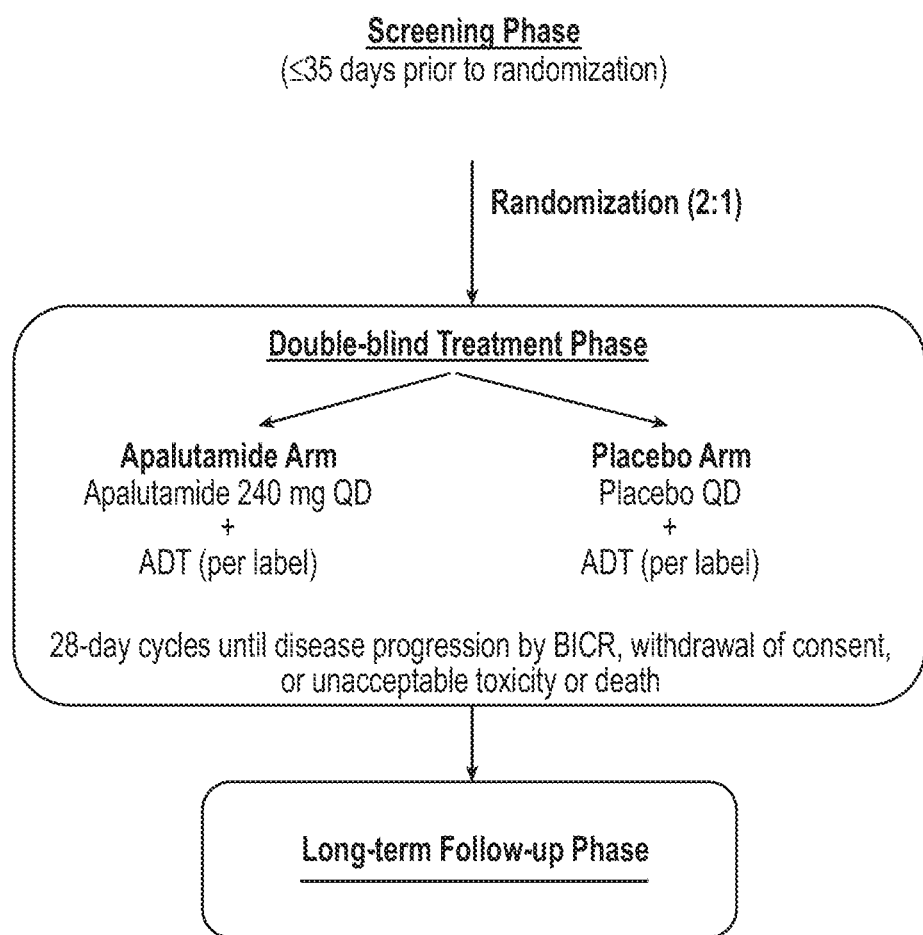
FIG. 2 is a schematic of the apalatamide phase III clinical trial study design. For the screening phase, eligible subjects are men ≥18 years old with high-risk NM-CRPC. Randomization (2:1) is stratified by PSADT, use of bone sparing agent, presence of loc-regional discease (N0-N1). Long-term follow-up phase is every 4 months for survival with continued disease evaluations every 16 weeks until documented disease progression. ADT=androgen deprivation therapy, BICR=blinded independent central review, PSADT=prostate specific antigen doubling time, NM-CRPC=non-metastatic castration-resistant prostate cancer, and * represents high-risk PSADT months.

Example 2: A Multicenter, Randomized, Double-Blind, Placebo-Controlled, Phase III Study of ARN-509 in Men with Non-Metastatic (M0) Castration-Resistant Prostate Cancer Primary Objective
 To demonstrate superiority in the MFS of men with high risk NM-CRPC (i.e., a PSADT of 10 months) treated with apalutamide versus placebo.
Secondary Objectives
 To compare the following parameters in men with NM-CRPC treated with apalutamide versus placebo: time to metastasis (TTM); progression-free survival (PFS); time to symptomatic progression; overall survival (OS); time to initiation of cytotoxic chemotherapy; and safety and tolerability.
Other Objectives
  To compare patient-reported outcomes (PROs) of health-related quality of life and prostate cancer-specific symptoms.
  To compare medical resource utilization (MRU) for men with high risk NM-CRPC treated with apalutamide versus placebo.
  To compare PSA Response Rate for men with high risk NM-CRPC treated with apalutamide versus placebo.
  To compare time to PSA progression for men with high risk NM-CRPC treated with apalutamide versus placebo.
  To compare progression-free survival with the first subsequent therapy (PFS2), for men with high risk NM-CRPC treated with apalutamide versus placebo.
  To evaluate the population pharmacokinetics (PK) of apalutamide.
  To evaluate the effect of apalutamide on ventricular repolarization in a subset of patients from selected clinical sites.
  To evaluate exploratory biomarkers predictive of response and resistance to apalutamide treatment.
Study Design
 This was a multinational, randomized, double-blind, placebo-controlled Phase 3 study of apalutamide compared with placebo in subjects with high risk NM-CRPC. The study consisted of a Screening Phase of up to 35 days before randomization to establish eligibility and document baseline measurements, a double-blind Treatment Phase (28-day treatment cycles; continuous dosing), and a Long-term Follow-up Phase to monitor PFS, survival status, subsequent prostate cancer therapy, PRO, and MRU. A total of 1207 patients with NM-CRPC were randomized in a 2:1 ratio (806 subjects in the apalutamide arm and 401 subjects in the placebo arm) to receive either apalutamide orally at a dose of 240 mg once daily in combination with ADT (medical castration or surgical castration) or placebo with ADT in a multicenter, double-blind, clinical trial (Study 1). A diagrammatic representation of the study design is presented in FIG. 2. The randomization was stratified as follows:

PSADT: <6 months vs. >6 months;
Bone-sparing agent use: Yes vs. No; and
Loco-regional disease: N0 vs. N1 (ie, nodal disease).

To ensure accurate and consistent determination of PSADT, the Interactive Voice Response System (IVRS) provided PSADT calculations (using a linear regression model of the natural logarithm of PSA and time) based on PSA values by date entered by the sites prior to randomization. Factors related to bone-sparing agent use and local-regional disease were entered by the site personnel at the time of randomization. Unblinding of treatment assignment during the study for non-emergency safety reasons occurred for 2 subjects.

Patients enrolled had a Prostate Specific Antigen (PSA) Doubling Time (PSADT)<10 months. All patients who were not surgically castrated received ADT continuously throughout the study. Seventy-three percent (73%) of patients received prior treatment with a first generation anti-androgen; 69% of patients received bicalutamide and 10% of patients received flutamide. Systemic corticosteroids were not allowed at study entry. PSA results were blinded and were not used for treatment discontinuation. Patients randomized to either arm were to continue treatment until disease progression defined by blinded central imaging review (BICR), initiation of new treatment, unacceptable toxicity or withdrawal. Upon BICR-confirmed development of distant metastatic disease, patients were offered ZYTIGA as an option for the first subsequent treatment after study treatment discontinuation.

Study Population

Men 18 years of age or older who had no radiographic evidence of detectable distant metastases as determined by BICR prior to study entry were eligible for the study.

Inclusion Criteria:

Subjects enrolled in this study were required to meet the following key acceptance criteria:

Histologically or cytologically confirmed adenocarcinoma of the prostate without neuroendocrine differentiation or small cell features, with high risk for development of metastases, defined as PSADT <10 months. PSADT is calculated using at least 3 PSA values obtained during continuous ADT;

Castration-resistant prostate cancer demonstrated during continuous ADT, defined as 3 PSA rises at least 1 week apart, with the last PSA >2 ng/mL;

Surgically or medically castrated, with testosterone levels of <50 ng/dL. If the patient is medically castrated, continuous dosing with a GnRH analogue must have been initiated at least 4 weeks prior to randomization and must be continued throughout the study to maintain castrate levels of testosterone;

Patients receiving bone loss prevention treatment with bone-sparing agents indicated for the treatment of osteoporosis at doses and dosing schedule appropriate for the treatment of osteoporosis (e.g., denosumab [PROLIA], zoledronic acid [RECLAST]) must be on stable doses for at least 4 weeks prior to randomization;

Patients who received a first-generation anti-androgen (e.g., bicalutamide, flutamide, nilutamide) must have at least a 4-week washout prior to randomization AND must show continuing disease (PSA) progression (an increase in PSA) after washout;

Resolution of all acute toxic effects of prior therapy or surgical procedure to Grade 1 or baseline prior to randomization;

Adequate organ function;

Signed and dated informed consent document indicating that the patient (or legally acceptable representative) has been informed of all pertinent aspects of the trial prior to randomization.

Exclusion Criteria:

Subjects were not enrolled into the study if it was determined upon pre-study examination that they met the following key criteria:

Presence of distant metastases confirmed by BICR, including central nervous system (CNS) and vertebral or meningeal involvement, or history of distant metastases. Exception: Pelvic lymph nodes <2 cm in short axis (N1) located below the iliac bifurcation are allowed;

Symptomatic loco-regional disease requiring medical intervention, such as moderate or severe urinary obstruction or hydronephrosis, due to primary tumor (e.g., tumor obstruction of bladder trigone);

Prior treatment with next generation anti-androgens (e.g., enzalutamide);

Prior treatment with CYP17 inhibitors (e.g., abiraterone acetate, orteronel, galerterone, ketoconazole, aminoglutethimide);

Prior chemotherapy for prostate cancer, except if administered in the adjuvant/neoadjuvant setting;

History of seizure or condition that may pre-dispose to seizure (e.g., prior stroke within 1 year prior to randomization, brain arteriovenous malformation, Schwannoma, meningioma, or other benign CNS or meningeal disease which may require treatment with surgery or radiation therapy);

Concurrent therapy with medications known to lower the seizure threshold, products that may decrease PSA levels, systemic corticosteroids, or other experimental treatments.

History or evidence of any of the following conditions:

Any prior malignancy (other than adequately treated basal cell or squamous cell skin cancer, superficial bladder cancer, or any other cancer in situ currently in complete remission) within 5 years prior to randomization;

Any of the following within 6 months prior to randomization: Severe/unstable angina, myocardial infarction, symptomatic congestive heart failure, arterial or venous thromboembolic events (e.g., pulmonary embolism, cerebrovascular accident including transient ischemic attacks), or clinically significant ventricular arrhythmias;

Uncontrolled hypertension (systolic blood pressure >160 mmHg or diastolic BP >100 mmHg). Patients with a history of uncontrolled hypertension are allowed provided blood pressure is controlled by anti-hypertensive treatment;

Gastrointestinal disorder affecting absorption;

Active infection, such as human immunodeficiency virus (HIV); and/or

Any other condition that, in the opinion of the Investigator, would impair the patient's ability to comply with study procedures.

Removal of Subjects from Therapy or Assessment:

Subject participation could be discontinued before completing the study for any of the following reasons:

Disease progression (confirmed by BICR);

Subject withdrawal of consent;

Any adverse event that could not be adequately managed with dose modifications (interruptions longer than 28 days required discussion with the Sponsor);
Lost to follow-up;
Any episode of seizure;
Protocol violation requiring discontinuation of study treatment;
Non-compliance with study procedures; and/or
Sponsor request for early termination of study.

Demographics and Baseline Characteristics:

Two thousand one hundred thirty-two (2,132) subjects signed the informed consent and were screened. One thousand two hundred and seven (1207) subjects were randomized. Of the 925 patients who were ineligible, 517 subjects were ineligible due to the presence of metastatic disease at screening. The following patient demographics and baseline disease characteristics were balanced between the treatment arms. The median age was 74 years (range 48-97) and 26% of patients were 80 years of age or older. The racial distribution was 66% Caucasian, 5.6% Black, 12% Asian, and 0.2% other. Seventy-seven percent (77%) of patients in both treatment arms had prior surgery or radiotherapy of the prostate. A majority of patients had a Gleason score of 7 or higher (81%). Fifteen percent (15%) of patients had <2 cm pelvic lymph nodes at study entry. All patients enrolled were confirmed to be non-metastatic by blinded central imaging review and had an Eastern Cooperative Oncology Group Performance Status (ECOG PS) performance status score of 0 or 1 at study entry.

Dosage and Administration

Apalutamide 240 mg (8×30 mg softgel capsules, then 4×60 mg tablets) or matching placebo were taken orally once daily with or without food. With the softgel capsules only, subjects could switch to a twice daily dosing regimen (4 tables each period) if gastrointestinal issues arose with the once daily schedule. If an apalutamide/placebo dose was missed, it was to be omitted and not made up. For the purposes of this study, a treatment cycle consisted of 4 weeks (28 days).

The dose and frequency of administration of the GnRH analogue as ADT followed the prescribing information in the respective label. Choice of GnRH analogue or dose could be adjusted if clinically indicated to achieve and maintain castrate concentrations of testosterone (<50 ng/dL).

Dose Modifications

Intrasubject dose interruptions and/or reductions were permitted provided that study discontinuation criteria had not been met.
Subjects reported with treatment-related seizure of any grade were to have study drug permanently discontinued.
For subjects reported with Grade 1-2 treatment-related adverse events (TEAEs), short treatment breaks were to be instituted per the discretion of the Investigator until the severity of the toxicity decreased to Grade 1 or returned to baseline. If toxicity recurred, dose reductions to the next lower dose level were allowed as per the discretion of the Investigator.
For subjects reported with Grade 3-4 TEAEs other than seizure, study drug was to be held until the severity of the toxicity decreased to Grade 1 or returned to baseline. If toxicity recurred at Grade 3 or higher, the dose of apalutamide was to be reduced to the next lower dose level.
A maximum of 2 dose level reductions was allowed (240 mg to 180 mg; 180 mg to 120 mg).
Any subject requiring >28-day delay in treatment due to TEAEs may have met one of the criteria for study treatment discontinuation described in Section 3.3. Re-starting study treatment after >28-day delay required discussion with the Sponsor.

Doses reduced for study treatment-related toxicities should generally not be re-escalated, however, re-escalation back to the previous dose level may have been permitted in consultation with the Sponsor (or designee).

Prior and Concomitant Therapy

Every medication or treatment taken by the subject during the study and the reason for administration was to be recorded on the CRF. Continuous treatment with a GnRH analogue or surgical castration was mandatory. Salvage radiation for loco-regional pelvic disease and surgical procedures (e.g., transurethral resection of the prostate [TURP], urethral and ureteral stent placement) to treat localized progression or symptoms were allowed. Details of prior prostate cancer related therapies are provided in Table 1.

TABLE 1

Overall Summary of Prior Prostate Cancer Therapy; Intent-to-treat Population

| ITT population | Placebo (401) | Apalutamide (806) | Total (1207) |
|---|---|---|---|
| | Previous prostate cancer therapy | | |
| N | 401 | 803 | 1204 |
| Surgery or radiotherapy | 307 (76.6%) | 617 (76.6%) | 924 (76.6%) |
| Surgery only | 69 (17.2%) | 159 (19.7%) | 228 (18.9%) |
| Radiotherapy only | 85 (21.2%) | 157 (19.5%) | 242 (20.0%) |
| Both surgery and Radiotherapy | 153 (38.2%) | 301 (37.3%) | 454 (37.6%) |
| Hormonal therapy | 400 (99.8%) | 801 (99.4%) | 1201 (99.5%) |
| GnRHa | 387 (96.5%) | 780 (96.8%) | 1167 (96.7%) |
| First generation Anti androgen | 290 (72.3%) | 592 (73.4%) | 882 (73.1%) |
| Orichiectomy | 24 (6.0%) | 47 (5.8%) | 71 (5.9%) |
| Other | 9 (2.2%) | 17 (2.1%) | 26 (2.2%) |
| Chemotherapy | 7 (1.7%) | 17 (2.1%) | 24 (2.0%) |
| Other | 32 (8.0%) | 64 (7.9%) | 96 (8.0%) |

Common concomitant medications, reported for 50% or more subjects included analgesics (apalutamide: 61%; placebo: 57%), agents acting on the renin-angiotensin system (apalutamide: 55%; placebo: 50%), and lipid modifying agents (apalutamide: 50%; placebo: 51%).

Prohibited Therapies

Drugs known to decrease the seizure threshold or cause seizure or both were prohibited while receiving study treatment. Other prohibited medications (per the exclusion criteria) included herbal (e.g., saw palmetto) and non-herbal products that may decrease PSA levels; systemic (oral/IV/IM) corticosteroids other than short term use (<4 weeks); any other experimental treatment; and agents indicated for the prevention of skeletal-related events in patients with solid tumors (e.g. denosumab [XGEVA]). Use of agents for prevention of osteoporosis (e.g., denosumab [PROLIA]) was allowed during the study. Use of 5-α reductase inhibitors, estrogens and any other anti-cancer therapy was to be discontinued at least 4 weeks prior to enrollment to the study.

Restricted Therapies

Investigators were informed of the potential for drug-drug interactions of apalutamide with concomitant medications, particularly strong CYP3A4 inducers or drugs with a narrow therapeutic index that are metabolized by CYP3A4 (apalutamide is an inducer of CYP3A4), and strong CYP2C8 inhibitors (e.g., gemfibrozil). The potential for drug-drug interaction between apalutamide and warfarin was not known. If a subject was taking warfarin, investigators were advised to re-assess prothrombin (PT)/international normalized ratio (INR) as clinically indicated and adjust the dose of warfarin accordingly. Additionally, due to possible resistance mechanisms, the concurrent use of systemic corticosteroids during study treatment was not recommended; short-term use (<4 weeks) was allowed if clinically indicated, however, its use must have been tapered off as soon as possible.

Dose Modification of Apalutamide

The majority of subjects were able to tolerate the full, prescribed dose of the study medication with 79% of subjects in the apalutamide arm and 85% of subjects in the placebo arm receiving no dose modifications. There were more dose reductions reported for subjects in the apalutamide arm (21%) compared with the placebo arm (15%). More subjects in the apalutamide arm had one dose reduction compared with the placebo arm (8.2% vs. 3.5%) while similar proportions of subjects from both treatment arms had two dose reductions (13% vs 11%, respectively). The most common reason for dose reduction for subjects in the apalutamide arm was adverse event (apalutamide arm: 11% vs. placebo arm: 3.3%) while "other" was the most common reason for the placebo arm (apalutamide arm: 9.7%; placebo arm: 12%). There were more dose interruptions due to TEAEs reported for subjects in the apalutamide arm (34%) compared with the placebo arm (19%). More subjects in the apalutamide arm had one dose interruption compared with the placebo arm (22% versus 13%) while similar proportions of subjects from both treatment arms had two or more dose interruptions (6.6% versus 5.3%, respectively, for 2 dose interruptions).

Efficacy Results

Primary Efficacy Analysis: Metastasis-Free Survival

Efficacy analyses were performed using the ITT population, which included 1207 randomized subjects (806 subjects in the apalutamide arm and 401 subjects in the placebo arm). The median survival follow-up time for all subjects was 20.3 months.

The primary efficacy endpoint was metastasis-free survival (MFS), defined as the time from randomization to the time of first evidence of BICR-confirmed bone or soft tissue distant metastasis or death due to any cause, whichever occurred first. Metastasis-free survival data for subjects without metastasis or death were censored on the date of the last tumor assessment (or, if no tumor assessment was performed after the baseline visit, at the date of randomization). Censoring rules based on FDA and CHMP guidance were applied for analyses of MFS (referred to in the text as US censoring or ex-US censoring). Treatment with apalutamide significantly improved MFS.

The appearance of new metastatic lesions denoted disease progression. For new bone lesions detected on bone scans, a second imaging modality (e.g., CT or MRI) was required to confirm progression.

Figure 3:
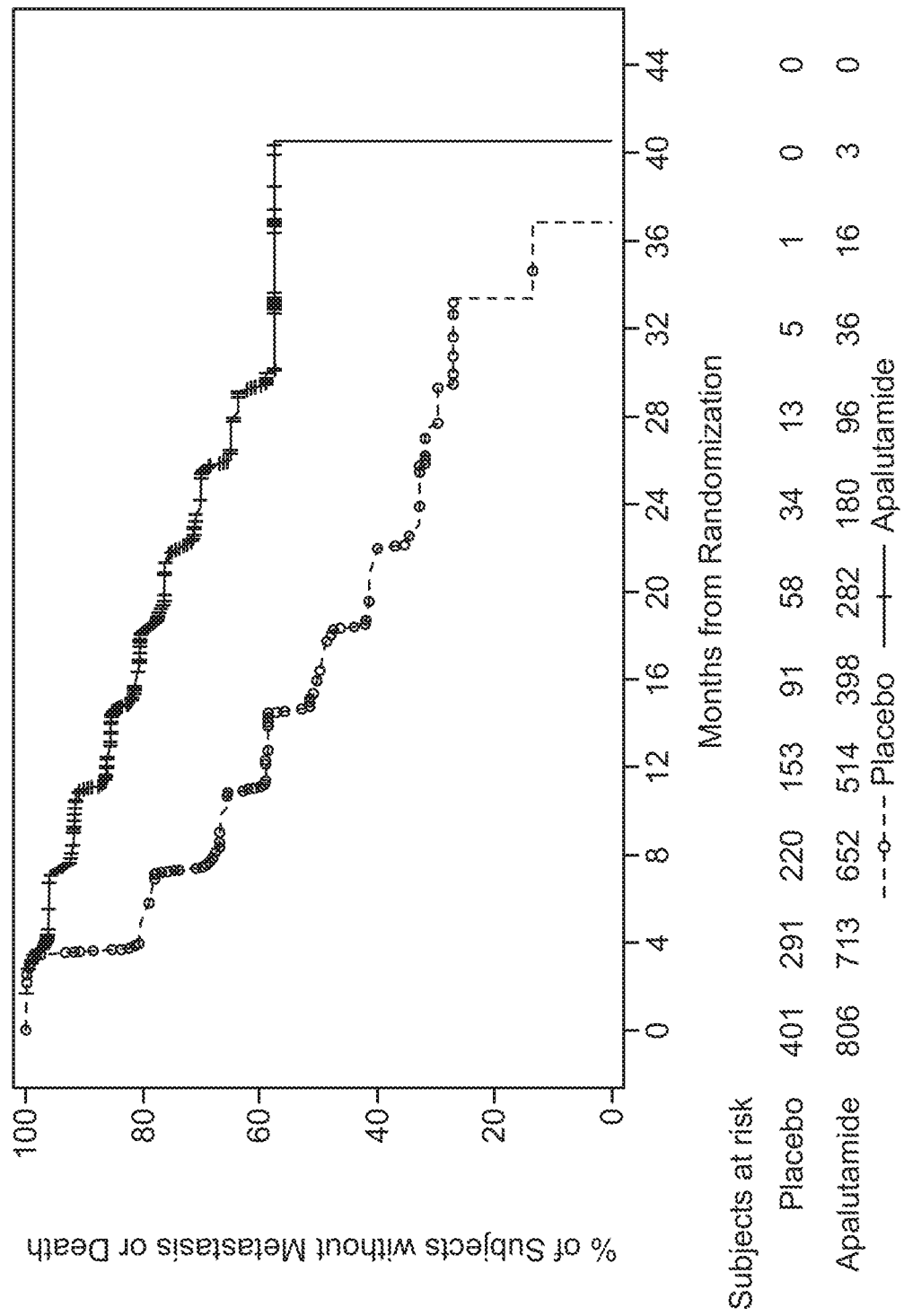
FIG. 3 illustrates a Kaplan-Meier plot of blinded independent central review (BICR) metastasis-free survival (MFS) for the U.S. regulatory, intent-to-treat population.
Figure 4:
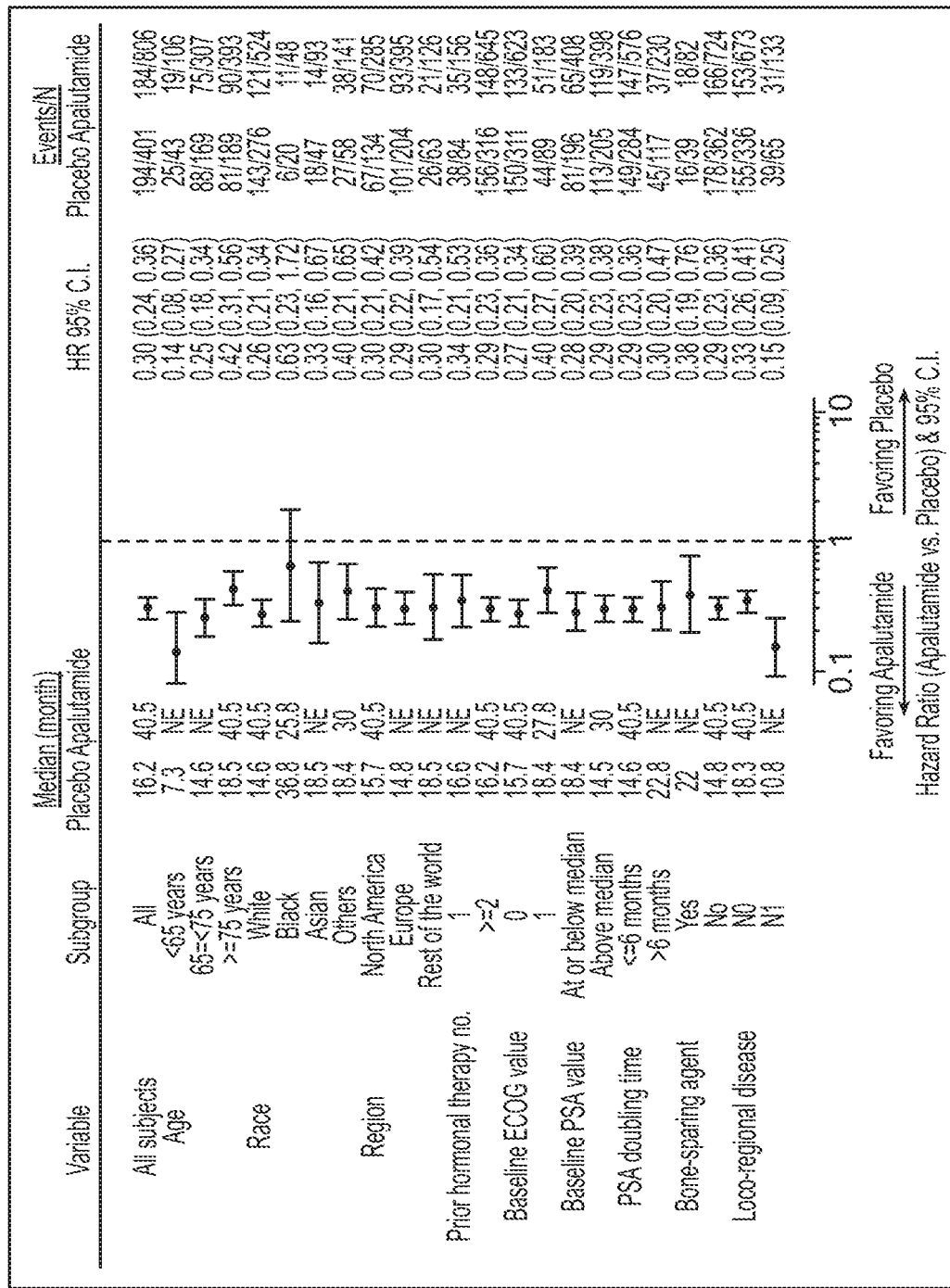
FIG. 4 is a forest plot of blinded independent central review (BICR) metastasis-free survival (MFS) for U.S. regulatory by subgroups defined by baseline clinical disease characteristics intent-to-treat population.

Apalutamide decreased the risk of distant metastasis or death by 72%. The median MFS for apalutamide was 41 months and was 16 months for placebo (see FIG. 3 and FIG. 4). The treatment effect of apalutamide on MFS was favorable across all subgroups and consistent with results for the total population. The non-stratified analysis of MFS by BICR for all subjects and subgroups is presented in FIG. 4. It is noteworthy that MFS for subjects with a PSA doubling time of months (HR=0.29) was consistent with results for subjects with a PSA doubling time of >6 months (HR=0.30) and with results for the total study population (HR=0.30; non-stratified analysis). Additionally, benefit is also noted in all age subgroups, both NO and N1 subgroups, and subjects with 1 or prior hormonal therapies.

Secondary Endpoint Analysis

Patients treated with apalutamide and ADT showed significant improvement over those treated with ADT alone for the following secondary endpoints of time to metastasis (TTM), progression-free survival (PFS), and time to symptomatic progression. In addition, overall survival (OS) and time to initiation of cytotoxic chemotherapy were also improved (see Table 2).

TABLE 1

Summary of Efficacy Analysis

| Endpoint | Apalutamide (n = 806) Median (months) | Placebo (n = 401) Median (months) | HR (95% CI) p value[1] |
|---|---|---|---|
| Metastasis Free Survival (MFS) | 40.5 | 16.2 | 0.28 (0.23-<0.0001 |
| Time to Metastasis (TTM) | 40.5 | 16.6 | 0.27 (0.22-<0.0001 |
| Progression-free Survival (PFS) | 40.5 | 14.7 | 0.29 (0.24-<0.0001 |
| Time to Symptomatic Progression | NR | NR | 0.45 (0.32-<0.0001[2] |
| Overall Survival (OS) | NR | 39.0 | 0.70 (0.47-0.0742 |
| Time to Initiation of Cytotoxic Chemotherapy | NR | NR | 0.44 (0.29-<0.0001 |

Figure 5:
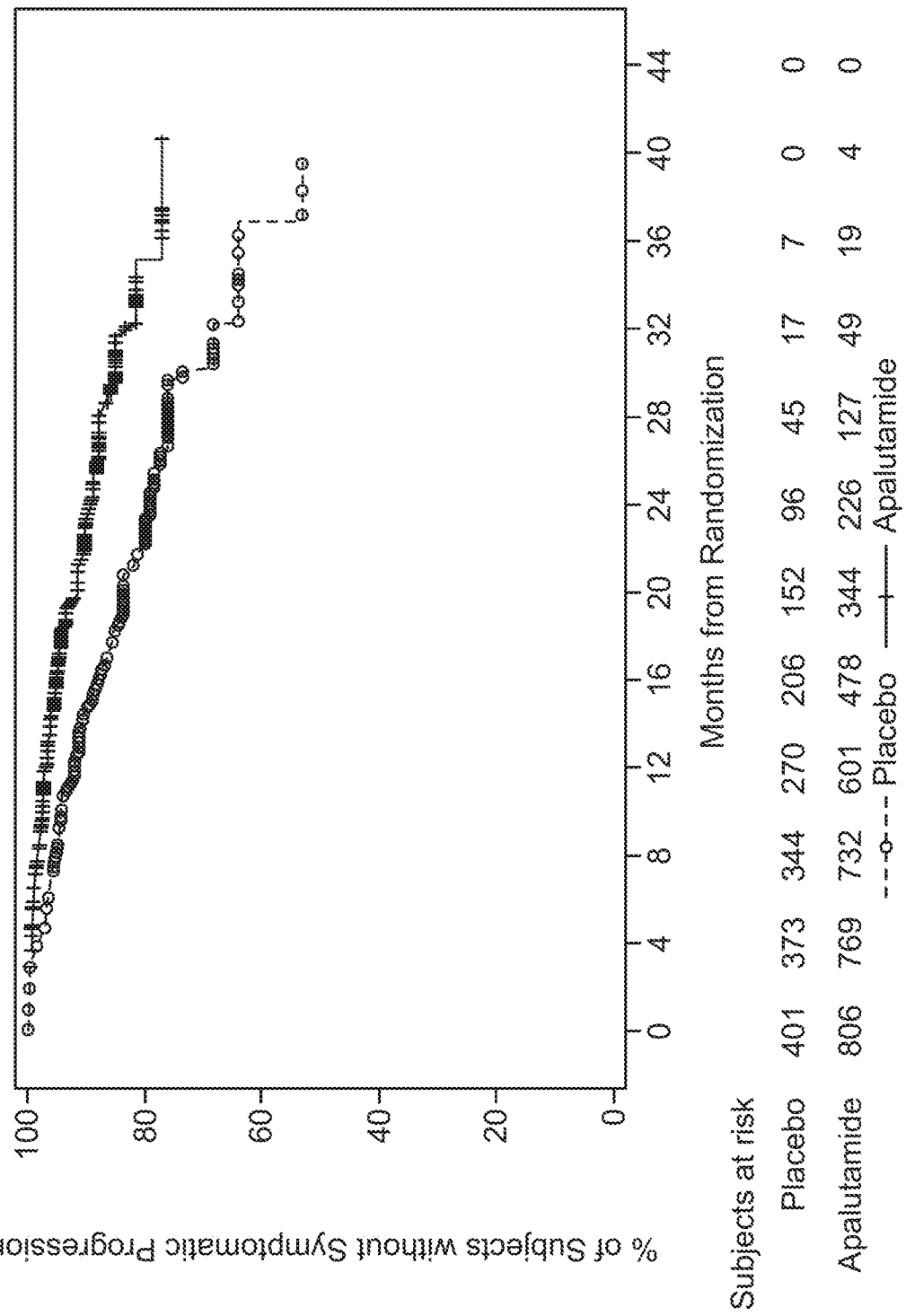
FIG. 5 illustrates a Kaplan-Meier plot of time to symptomatic progression; intent-to-treat population.

NR = Not reached
[1]p value from stratified log-rank test
[2]Actual p value - 0.00000356; hence, OBF-type efficacy boundary of 0.00008 is crossed in the interim analysis for Symptomatic Progression Treatment with apalutamide significantly decreased the risk of symptomatic progression by 55% compared with placebo. The observed p-value (0.00000356) crossed the Obrien-Fleming (OBF) efficacy boundary (p=0.00008) for significance. (see Table 2 and FIG. 5).

Overall survival was longer for apalutamide than placebo with a hazard ratio (HR) of 0.700 (95% CI: 0.472, 1.038). The p-value was 0.0742, which did not meet the pre-specified value for statistical significance.

Thirty-nine percent (39%) of patients treated with apalutamide and 70% of patients treated with placebo discontinued study treatment. A greater proportion (80%) of patients treated with placebo received subsequent therapy compared to patients treated with apalutamide (56%). Post-progression survival (PFS-2, defined as the time to disease progression after first subsequent therapy or death) was longer for patients treated with apalutamide compared to those treated with placebo (HR=0.489; 95% CI: 0.361, 0.662; p<0.0001).

Safety Results

Data Sets Analyzed

Summaries of adverse events and other safety data are based on the Safety Population that comprises the 1201 subjects who received at least 1 dose of either apalutamide or placebo (803 subjects in the apalutamide arm and 398 subjects in the placebo arm).

Adverse Events

The most common adverse reactions (15%) reported in the randomized clinical study that occurred more commonly (>2%) in the apalutamide arm were fatigue, skin rash, weight decreased, arthralgia, and fall. Discontinuations due to adverse events were reported for 11% of patients treated with apalutamide and 7% of patients treated with placebo. There were no statistically significant differences observed in the change from baseline analysis of the Functional Assessment of Cancer Therapy-Prostate (FACT-P) for the total score or any of the subscales between patients on apalutamide added to ADT versus placebo with ADT. At the time of the analysis, 61% of patients were still on apalutamide and 30% of patients were still on placebo. Table 3 shows adverse reactions on the apalutamide arm that occurred with a 2% absolute increase in frequency compared to placebo or were events of special interest.

TABLE 3

Adverse Reactions due to Apalutamide in Study 1

| System/Organ Class Adverse reaction | Apalutamide N = 803 | | Placebo N = 398 | |
|---|---|---|---|---|
| | All Grades % | Grade 3-4 % | All Grades % | Grade 3-4 % |
| General disorders and administration site conditions | | | | |
| Fatigue[4] | 30.4 | 0.9 | 21.1 | 0.3 |
| Musculoskeletal and connective tissue disorders | | | | |
| Arthralgia[4] | 15.9 | 0 | 7.5 | 0 |
| Skin and subcutaneous tissue disorders | | | | |
| Skin rash[1] | 23.8 | 5.2 | 5.5 | 0.3 |
| Pruritus[4] | 6.2 | 0.2 | 1.5 | 0 |
| Nervous system disorders | | | | |
| Seizure | 0.2 | 0 | 0 | 0 |
| Metabolism and nutrition disorders | | | | |
| Hypercholesterolemia | 6.1 | 0 | 1.5 | 0 |
| Hypertriglyceridemia | 3.5 | 0.6 | 0.8 | 0.3 |
| Injury, poisoning and procedural complications | | | | |
| Fracture[2] | 11.7 | 2.7 | 6.5 | 0.8 |
| Fall[4] | 15.6 | 1.7 | 9.0 | 0.8 |
| Investigations | | | | |
| Weight decreased[4] | 16.1 | 1.1 | 6.3 | 0.3 |
| Endocrine disorders | | | | |
| Hypothyroidism[3] | 8.1 | 0 | 2.0 | 0 |

[1]Includes rash, rash maculo-papular, rash generalized, urticaria, rash pruritic, rash macular, conjunctivitis, erythema multiforme, rash papular, skin exfoliation, genital rash, rash erythematous, stomatitis, drug eruption, mouth ulceration, rash pustular, blister, papule, pemphigoid, skin erosion, and rash vesicular
[2]Includes rib fracture, lumbar vertebral fracture, spinal compression fracture, spinal fracture, foot fracture, hip fracture, humerus fracture, thoracic vertebral fracture, upper limb fracture, fractured sacrum, hand fracture, pubis fracture, acetabulum fracture, ankle fracture, compression fracture, costal cartilage fracture, facial bones fracture, lower limb fracture, osteoporotic fracture, wrist fracture, avulsion fracture, fibula fracture, fractured coccyx, pelvic fracture, radius fracture, sternal fracture, stress fracture, traumatic fracture, cervical vertebral fracture, femoral neck fracture, tibia fracture
[3]Includes hypothyroidism, blood thyroid stimulating hormone increased, thyroxine decreased, autoimmune thyroiditis, thyroxine free decreased, tri-iodothyronine decreased
[4]Grade 4 definitions do not exist for these reactions 1. Skin Rash Skin rash associated with apalutamide was most commonly described as macular or maculo-papular. Adverse events of skin rash were reported for 24% of patients treated with apalutamide versus 5.5% of patients treated with placebo. Grade 3 skin rashes (defined as covering >30% body surface area [BSA]) were reported with apalutamide treatment (5.2%) versus placebo (0.3%). There were no reported events of toxic epidermal necrolysis (TEN) or Stevens-Johnson syndrome (SJS).

The onset of skin rash occurred at a median of 82 days of apalutamide treatment and resolved within a median of 60 days from onset of rash for 81% of patients. Medications utilized included topical corticosteroids, systemic corticosteroids and oral anti-histamines. Among patients with skin rash, dose interruption occurred in 28% and dose reduction occurred in 12%. Skin rash recurred in approximately half of patients who were re-challenged, with no serious allergic reactions. Skin rash led to apalutamide treatment discontinuation in 9% of patients who experienced skin rash.

2. Falls and Fractures

Fracture was reported for 11.7% of patients treated with apalutamide and 6.5% of patients treated with placebo. Half of the patients experienced a fall within 7 days before the fracture event in both treatment groups. Falls were reported for 15.6% of patients treated with apalutamide versus 9.0% of patients treated with placebo.

3. Hypothyroidism

Hypothyroidism was reported for 8.1% of patients treated with apalutamide and 2.0% of patients treated with placebo based on assessments of thyroid-stimulating hormone (TSH) every 4 months. There were no grade 3 or 4 adverse events. Hypothyroidism occurred in 28% of patients already receiving thyroid replacement therapy in the apalutamide arm and in 5.9% of patients in the placebo arm. In patients not receiving thyroid replacement therapy, hypothyroidism occurred in 5.7% of patients treated with apalutamide and in 0.8% of patients treated with placebo. Thyroid replacement therapy, when clinically indicated, should be initiated or dose-adjusted.

4. Laboratory Abnormalities

Hypercholesterolemia was observed in 6.1% of patients treated with apalutamide and 1.5% of patients treated with placebo. Hypertriglyceridemia was observed in 3.5% of patients treated with apalutamide and 0.8% of patients treated with placebo.

Conclusion

Apalutamide in combination with ADT showed superior efficacy in comparison with ADT alone for patients with NM-CRPC. Apalutamide plus ADT significantly improved MFS, TTM, PFS, and time to symptomatic progression compared with ADT alone. Though survival data are not yet mature at the time of this analysis for MFS, treatment with apalutamide plus ADT resulted in favorable OS compared with ADT alone. Additionally, a compelling result for time to initiation of cytotoxic chemotherapy was observed. Significant improvements were consistently observed across clinically relevant endpoints including PSA response rate, time to PSA progression, and progression-free survival during first subsequent therapy (PFS2). There was no detrimental effect or worsening of symptoms that impacted the quality of life from the addition of apalutamide to ADT in this population of men with NM-CRPC who are generally asymptomatic. With the exception of small numerical increases in skin rash, fall, fracture, and hypothyroidism, when adjusted for exposure, apalutamide in combination with ADT did not have a clinically meaningful increase in the incidence of TEAEs compared with subjects who received ADT alone. The majority of TEAEs reported were Grade 1 or 2 and were not dose-limiting. Grade 3 events were manageable, being largely related to hypertension (in both treatment arms) and skin rash (as a grouped term) in the apalutamide arm with a low rate of treatment discontinuation due to TEAEs in both treatment arms (11% in the apalutamide arm versus 7% in the placebo arm). Collectively, the data demonstrate a favorable benefit-risk profile of the apalutamide+ADT regimen for the treatment of subjects with NM CRPC at high risk for metastasis.

Example 3: Pharmacodynamics and Pharmacokinetics

Pharmacodynamics
Cardiac Electrophysiology

The effect of apalutamide 240 mg once daily on the QT interval was evaluated in patients with CRPC in a dedicated QT study. There was no difference greater than 20 ms in the mean QT interval change from baseline, based on the Fridericia correction method, across all timepoints at steady-state.

Pharmacokinetics

A population PK analysis of apalutamide and its active metabolite was conducted. Following repeat once-daily dosing, apalutamide exposure ($C_{max}$ and area under the concentration curve [AUC]) increased in a dose-proportional manner across the dose range of 30 to 480 mg. Following administration of 240 mg once daily, apalutamide steady state was achieved after 4 weeks and the mean accumulation ratio was approximately 5-fold relative to a single dose. At steady-state, mean (CV %) $C_{max}$ and AUC values for apalutamide were 6 μg/mL (28%) and 100 μg·h/mL (32%), respectively. Daily fluctuations in apalutamide plasma concentrations were low, with mean peak-to-trough ratio of 1.63. An increase in apparent clearance (CL/F) was observed with repeat dosing, likely due to induction of apalutamide's own metabolism.

At steady-state, the mean (CV %) $C_{max}$ and AUC values for the major active metabolite, N-desmethyl apalutamide, were 5.9 μg/mL (18%) and 124 μg/h/mL (19%), respectively. N-desmethyl apalutamide is characterized by a flat concentration-time profile at steady-state with a mean peak-to-trough ratio of 1.27. Mean (CV %) AUC metabolite/parent drug ratio for N-desmethyl apalutamide following repeat-dose administration was about 1.3 (21%). Based on systemic exposure, relative potency, and pharmacokinetic properties, N-desmethyl apalutamide likely contributed to the clinical activity of apalutamide.

Absorption

After oral administration, median time to achieve peak plasma concentration ($t_{max}$) was 2 hours (range: 1 to 5 hours). Mean absolute oral bioavailability is approximately 100%, indicating that apalutamide is completely absorbed after oral administration.

Administration of apalutamide to healthy patients under fasting conditions and with a high-fat meal resulted in no clinically relevant changes in $C_{max}$ and AUC. Median time to reach $t_{max}$ was delayed about 2 hours with food (see FIG. 3) [see Dosage and Administration (2.1)].

Distribution

The mean apparent volume of distribution at steady-state of apalutamide is about 276 L. The volume of distribution of apalutamide is greater than the volume of total body water, indicative of extensive extravascular distribution.

Apalutamide and N-desmethyl apalutamide are 96% and 95% bound to plasma proteins, respectively, and mainly bind to serum albumin with no concentration dependency.

Elimination

The CL/F of apalutamide is 1.3 L/h after single dosing and increases to 2.0 L/h at steady-state after once-daily dosing. The mean effective half-life for apalutamide in patients is about 3 days at steady-state.

Metabolism

Following single oral administration of $^{14}$C-labeled apalutamide 240 mg, apalutamide, the active metabolite, N-desmethyl apalutamide, and an inactive carboxylic acid metabolite accounted for the majority of the $^{14}$C-radioactivity in plasma, representing 45%, 44%, and 3%, respectively, of the total $^{14}$C-AUC. Metabolism is the main route of elimination of apalutamide. It is metabolized primarily by CYP2C8 and CYP3A4 to form N-desmethyl apalutamide. Apalutamide and N-desmethyl apalutamide are further metabolized to form the inactive carboxylic acid metabolite by carboxylesterase. The contribution of CYP2C8 and CYP3A4 in the metabolism of apalutamide is estimated to be 58% and 13% following single dose but changes to 40% and 37%, respectively at steady-state.

Excretion

Apalutamide, mainly in the form of metabolites, is eliminated primarily via urine. Following a single oral administration of radiolabeled apalutamide, 89% of the radioactivity was recovered up to 70 days post-dose: 65% was recovered in urine (1.2% of dose as unchanged apalutamide and 2.7% as N-desmethyl apalutamide) and 24% was recovered in feces (1.5% of dose as unchanged apalutamide and 2% as N-desmethyl apalutamide).

Specific Populations

Figure 6:
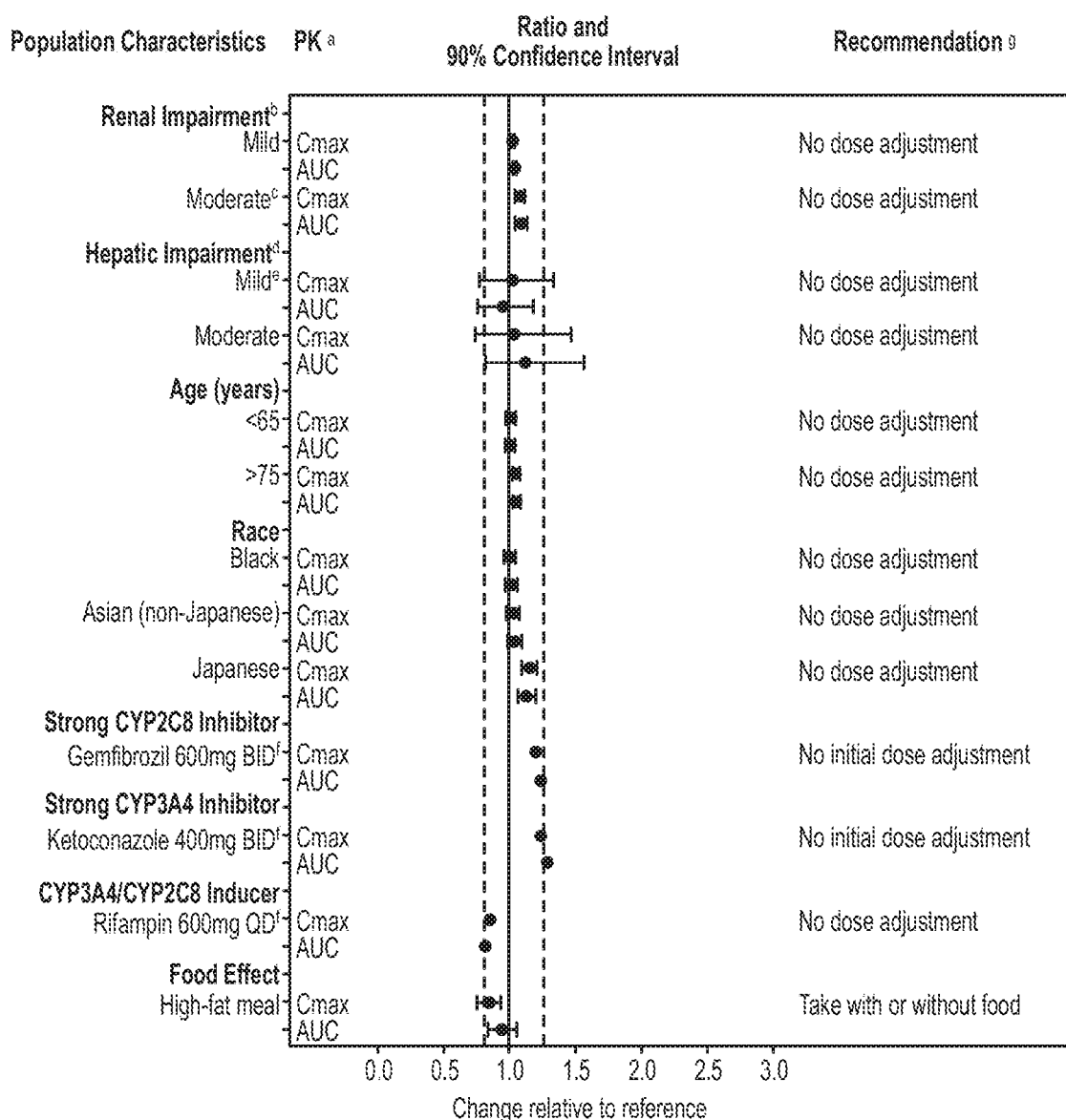
FIG. 6 illustrates the effects of intrinsic/extrinsic factors and other medications on apalutamide. $^a$Pharmacokinetic (PK) parameters (Cmax and AUC) are for apalutamide, except in the drug interaction studies, where they are for active moieties (i.e., unbound apalutamide+potency adjusted unbound N-desmethyl apalutamide). $^b$Degree of renal impairment was determined based on eGFR using the modification of diet in renal disease (MDRD) study equation; normal (≥90 mL/min/1.73 m$^2$), mild (60-89 mL/min/1.73 m$^2$), moderate (30-59 mL/min/1.73 m$^2$). $^c$Data included 2 subjects with severe renal impairment (≤29 mL/min/1.73 m$^2$). $^d$Degree of hepatic impairment was determined based on Child-Pugh classification; mild (Child-Pugh A), moderate (Child-Pugh). $^e$A population PK analysis demonstrated that mild hepatic impairment (based on the National Cancer Institute criteria) does not influence the exposure of apalutamide. $^f$Effect on steady-state PK of active moieties based on simulations. $^g$See Drug Interactions (7.1 and 7.2) and use in Specific Populations (8.6 and 8.7).

The effects of renal impairment, hepatic impairment, age, race, and other extrinsic factors on the pharmacokinetics of apalutamide are summarized in FIG. 6. No clinically significant differences in the pharmacokinetics of apalutamide and N-desmethyl apalutamide were observed in subjects with mild (eGFR 60-89 mL/min/1.73 m$^2$) or moderate renal impairment (eGFR 3059 mL/min/1.73 m$^2$), mild (Child-Pugh A) or moderate (Child-Pugh B) hepatic impairment, age ranging from 18 to 94 years, or between different races. The potential effect of severe renal impairment or end stage renal disease (eGFR 29 mL/min/1.73 m$^2$) have not been established due to insufficient data. Clinical and pharmacokinetic data are not available for patients with severe hepatic impairment (Child-Pugh Class C).

Example 4: Drug Interactions

Drug Interactions
Effect of Other Medications on Apalutamide
1. Strong CYP2C8 Inhibitors In a drug-drug interaction study, the $C_{max}$ of apalutamide decreased by 21% while AUC increased by 68% following co-administration of apalutamide as a 240 mg single dose with gemfibrozil (strong CYP2C8 inhibitor). Simulations suggest that gemfibrozil may increase the steady-state $C_{max}$ and AUC of apalutamide by 32% and 44%, respectively. For the active moieties (sum of unbound apalutamide plus the potency-adjusted unbound active metabolite), the steady-state $C_{max}$ and AUC may increase by 19% and 23%, respectively (see FIG. 6).

2. Strong CYP3A4 Inhibitors

In a drug-drug interaction study, the $C_{max}$ of apalutamide decreased by 22% while AUC was similar following co-administration of apalutamide as a 240 mg single dose with itraconazole (strong CYP3A4 inhibitor). Simulations suggest that ketoconazole (strong CYP3A4 inhibitor) may increase the steady-state $C_{max}$ and AUC of apalutamide by 38% and 51%, respectively. For the active moieties, the steady-state $C_{max}$ and AUC may increase by 23% and 28%, respectively (see FIG. 6).

3. CYP3A4/CYP2C8 Inducers

The effects of CYP3A4 or CYP2C8 inducers on the pharmacokinetics of apalutamide have not been evaluated in vivo. Simulations suggest that rifampin (strong CYP3A4 and moderate CYP2C8 inducer) may decrease the steady-state $C_{max}$ and AUC of apalutamide by 25% and 34%, respectively. For the active moieties, the steady-state $C_{max}$ and AUC may decrease by 15% and 19%, respectively (see FIG. 6).

4. Acid Lowering Agents

Apalutamide is not ionizable under relevant physiological pH condition, therefore acid lowering agents (e.g. proton pump inhibitor, H$_2$-receptor antagonist, antacid) are not expected to affect the solubility and bioavailability of apalutamide.

5. Drugs Affecting Transporters

In vitro, apalutamide and its N-desmethyl metabolite are substrates for P-gp but not BCRP, OATP1B1, and OATP1B3. Because apalutamide is completely absorbed after oral administration, P-gp does not limit the absorption of apalutamide and therefore, inhibition or induction of P-gp is not expected to affect the bioavailability of apalutamide.

Effect of Apalutamide on Other Medications

Figure 7:
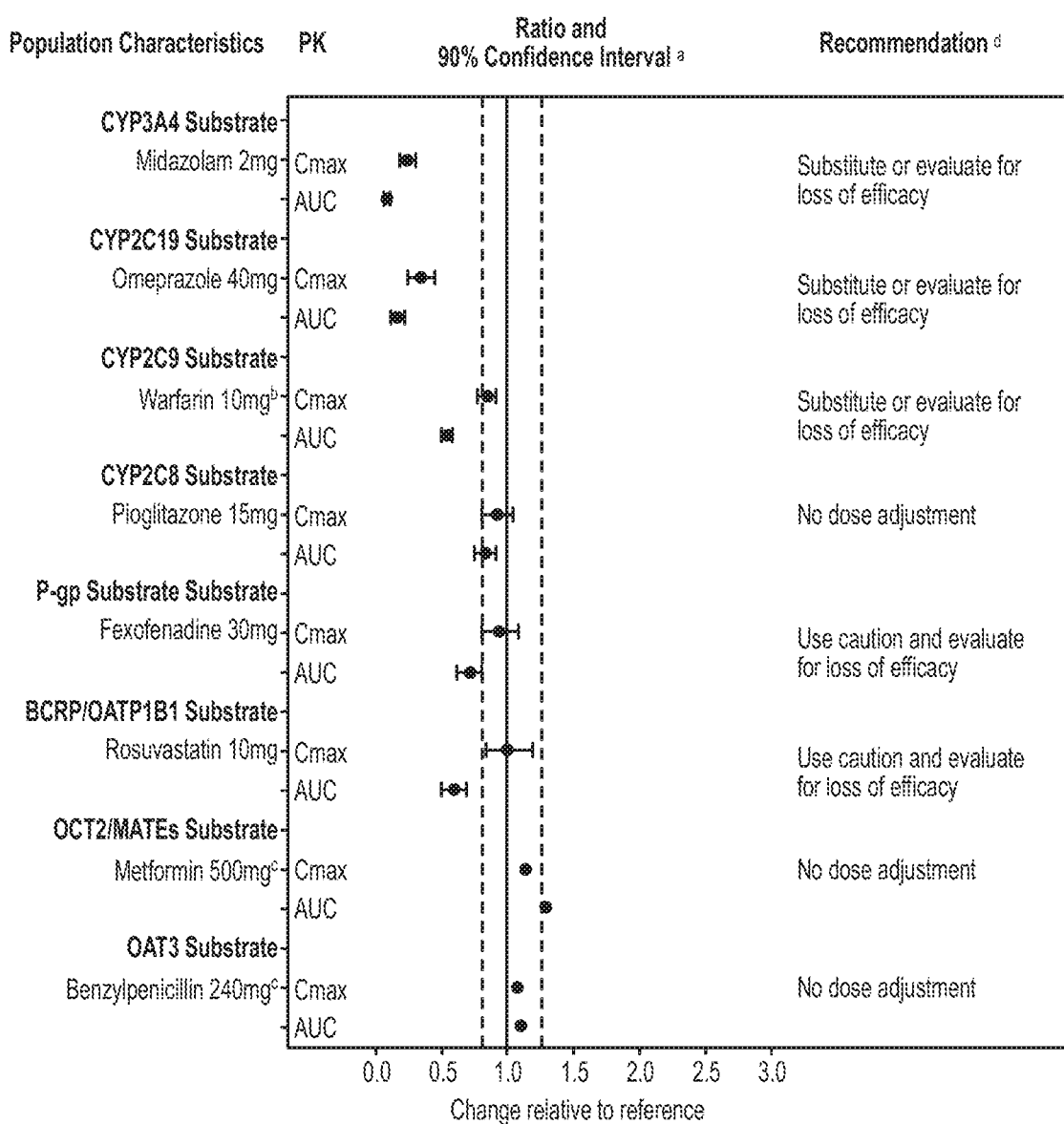
FIG. 7 illustrates the effects of apalutamide on the pharmacokinetics of other drugs. $^a$Combination/no combination.

The effects of apalutamide on the pharmacokinetics of other drugs are summarized in FIG. 7.

1. Major CYP Isoform Substrates

In vitro studies showed that apalutamide and N-desmethyl apalutamide are moderate to strong CYP3A4 and CYP2B6 inducers, are moderate inhibitors of CYP2B6 and CYP2C8, and weak inhibitors of CYP2C9, CYP2C19, and CYP3A4. Apalutamide and N-desmethyl apalutamide do not affect CYP1A2 and CYP2D6 at therapeutically relevant concentrations. In a drug-drug interaction study using a cocktail approach, co-administration of apalutamide with single oral doses of sensitive CYP substrates resulted in a 92% decrease in the AUC of midazolam (CYP3A4 substrate), 85% decrease in the AUC of omeprazole (CYP2C19 substrate), and 46% decrease in the AUC of S-warfarin (CYP2C9 substrate). Apalutamide did not cause clinically meaningful changes in exposure to the CYP2C8 substrate (see FIG. 7).

2. P-Gp, BCRP and OATP1B1 Substrates

Apalutamide was shown to be a weak P-gp and BCRP/OATP1B1 inducer clinically. A drug-drug interaction study using a cocktail approach showed that co-administration of apalutamide with single oral doses of sensitive transporter substrates resulted in a 30% decrease in the AUC of fexofenadine (P-gp substrate) and 41% decrease in the AUC of rosuvastatin (BCRP/OATP1B1 substrate) but had no impact on $C_{max}$ (see FIG. 7).

3. UDP-Glucuronosyl Transferase (UGT) Substrates

Induction of CYP3A4 by apalutamide suggests that UDP-glucuronosyl transferase (UGT) may also be induced via activation of the nuclear pregnane X receptor (PXR). Concomitant administration of apalutamide with medications that are substrates of UGT can result in lower exposure to these medications.

4. OCT2, OAT1, OAT3 and MATEs Substrates

Based on in vitro data, inhibition of organic cation transporter 2 (OCT2), organic anion transporter 3 (OAT3) and multidrug and toxin extrusions (MATEs) by apalutamide and its N-desmethyl metabolite cannot be excluded. No in vitro inhibition of organic anion transporter 1 (OAT1) was observed. Simulations suggest that apalutamide does not cause clinically meaningful changes in exposure to metformin (OCT2/MATEs substrate) and benzylpenicillin (OAT3 substrate) (see FIG. 7).

Example 5: Nonclinical Toxicology

Carcinogenesis, Mutagenesis, Impairment of Fertility

Long-term animal studies have not been conducted to evaluate the carcinogenic potential of apalutamide. Apalutamide did not induce mutations in the bacterial reverse mutation (Ames) assay and was not genotoxic in either in vitro chromosome aberration test, the in vivo rat micronucleus assay or the in vivo rat Comet assay.

Male fertility is likely to be impaired by treatment with apalutamide based on findings in repeat-dose toxicology studies which were consistent with the pharmacological activity of apalutamide. In repeat-dose toxicity studies in male rats (up to 26 weeks) and dogs (up to 39 weeks), atrophy, aspermia/hypospermia, degeneration and/or hyperplasia or hypertrophy in the reproductive system were observed at >25 mg/kg/day in rats (1.4 times the human exposure based on AUC) and >2.5 mg/kg/day in dogs (0.9 times the human exposure based on AUC).

In a fertility study in male rats, a decrease in sperm concentration and motility, copulation and fertility rates (upon pairing with untreated females) along with reduced weights of the secondary sex glands and epididymis were observed following 4 weeks of dosing at >25 mg/kg/day (approximately equal to the human exposure based on AUC). Effects on male rats were reversible after 8 weeks from the last apalutamide administration.

Example 6: Formulation of Apalutamide

Apalutamide/matched placebo were originally formulated as a nonaqueous, lipid-based solution that was filled into 30 mg strength, size 18 softgel oblong-shaped capsules (ARN-509 Softgel Capsules, 30 mg), with a clear to hazy light yellow to yellow color. Each 30 mg softgel capsule of apalutamide/matched placebo contained the following inactive ingredients: vitamin E d-α-tocopheryl polyethylene glycol succinate 1000 NF (Vitamin E TPGS), polyethylene glycol 400 NF/EP (PEG 400), glycerol monocaprylocaprate EP (Capmul MCM), caprylocaproyl macroglycerides NF/EP (Acconon MC8-2), gelatin NF/EP (195 Acid Bloom), a 50:50 sorbitol/glycerin blend USP/EP, purified water USP/EP, medium chain triglycerides NF/EP (fractionated coconut oil), and lecithin, unbleached NF (Capsulec gel 60). The gelatin 195 Acid Bloom NF/EP was derived from bovine origin and certified in accordance with FDA's Guidance for Industry—The Sourcing and Processing of Gelatin to Reduce the Potential Risk Posed by Bovine Spongiform Encephalopathy (BSE) in FDA-regulated Products for Human Use (September 1997). Placebo capsule was matched in size, color, and shape to active study drug in order to maintain the study blind.

Apalutamide/placebo softgel capsules were replaced with tablets (commercial formulation) due to stability issues with the capsule and large capsule burden for subjects (8 capsules compared to 4 tablets). Newly enrolled subjects in the study received tablets only whereas ongoing subjects at the time of the amendment were switched from capsules to tablets. The apalutamide tablet contained 60 mg of apalutamide and the following inactive ingredients: hydroxypropyl methylcellulose-acetate succinate (HPMC-AS), colloidal anhydrous silica, croscarmellose sodium, microcrystalline cellulose, silicified microcrystalline cellulose, and magnesium stearate. Commercially available OPADRY coating powder was used for the film coating, which was comprised of polyvinyl alcohol (partially hydrolyzed), titanium dioxide, polyethylene glycol, talc, and colorants iron oxide yellow and iron oxide black (E172). It was manufactured and provided under the responsibility of the Sponsor. Placebo tablet was matched in size, color, and shape to active study drug in order to maintain the study blind.

Example 7 Final FDA Approved Drug Product Label

The FDA approved the following drug product label on Feb. 14, 2018 for ERLEADA™ (apalutamide), which will be the reference listed drug for apalutamide.

HIGHLIGHTS OF PRESCRIBING INFORMATION
These highlights do not include all the information needed to use ERLEADA safely and effectively. See full prescribing information for ERLEADA.

ERLEADA™ (apalutamide) tablets, for oral use
Initial U.S. Approval – 2018

---------------------------INDICATIONS AND USAGE-------------------------
ERLEADA is an androgen receptor inhibitor indicated for the treatment of patients with non-metastatic castration-resistant prostate cancer. (1)

------------------------DOSAGE AND ADMINISTRATION-------------------
ERLEADA 240 mg (four 60 mg tablets) administered orally once daily. Swallow tablets whole. ERLEADA can be taken with or without food. (2.1)

Patients should also receive a gonadotropin-releasing hormone (GnRH) analog concurrently or should have had bilateral orchiectomy. (2.1)

----------------------DOSAGE FORMS AND STRENGTHS------------------
Tablets: 60 mg (3)

-----------------------------CONTRAINDICATIONS----------------------------
Pregnancy (4, 8.1)

-----------------------WARNINGS AND PRECAUTIONS----------------------
- Falls and Fractures occurred in 16% and 12% of patients receiving ERLEADA, respectively. Evaluate patients for fracture and fall risk, and treat patients with bone targeted agents according to established guidelines. (5.1)

- Seizure occurred in 0.2% of patients receiving ERLEADA. Permanently discontinue ERLEADA in patients who develop a seizure during treatment. (5.2)

------------------------------ADVERSE REACTIONS----------------------------
The most common adverse reactions (≥10%) are fatigue, hypertension, rash, diarrhea, nausea, weight decreased, arthralgia, fall, hot flush, decreased appetite, fracture, and peripheral edema. (6.1)

To report SUSPECTED ADVERSE REACTIONS, contact Janssen Products, LP at 1-800-526-7736 (1-800-JANSSEN or FDA at 1-800-FDA-1088 or *www.fda.gov/medwatch*.

------------------------------DRUG INTERACTIONS------------------------------
- Concomitant use with medications that are sensitive substrates of CYP3A4, CYP2C19, CYP2C9, UGT, P-gp, BCRP, or OATP1B1 may result in loss of activity of these medications. (7.2)

------------------------USE IN SPECIFIC POPULATIONS----------------------
- Females and Males of Reproductive Potential: Advise males with female partners of reproductive potential to use effective contraception. (8.3)

See 17 for PATIENT COUNSELING INFORMATION and FDA-approved patient labeling.

Revised: 02/2018

---

FULL PRESCRIBING INFORMATION: CONTENTS\*

1 INDICATIONS AND USAGE
2 DOSAGE AND ADMINISTRATION
   2.1 Recommended Dosage
   2.2 Dose Modification
3 DOSAGE FORMS AND STRENGTHS
4 CONTRAINDICATIONS
5 WARNINGS AND PRECAUTIONS
   5.1 Falls and Fractures
   5.2 Seizure
6 ADVERSE REACTIONS
   6.1 Clinical Trial Experience
7 DRUG INTERACTIONS
   7.1 Effect of Other Drugs on ERLEADA
   7.2 Effect of ERLEADA on Other Drugs
8 USE IN SPECIFIC POPULATIONS
   8.1 Pregnancy
   8.2 Lactation
   8.3 Females and Males of Reproductive Potential
   8.4 Pediatric Use
   8.5 Geriatric Use 10 OVERDOSAGE
11 DESCRIPTION
12 CLINICAL PHARMACOLOGY
  12.1 Mechanism of Action
  12.2 Pharmacodynamics
  12.3 Pharmacokinetics
13 NONCLINICAL TOXICOLOGY
  13.1 Carcinogenesis, Mutagenesis, Impairment of Fertility
14 CLINICAL STUDIES
16 HOW SUPPLIED/STORAGE AND HANDLING
17 PATIENT COUNSELING INFORMATION

\*Sections or subsections omitted from the full prescribing information are not listed.

FULL PRESCRIBING INFORMATION

1 INDICATIONS AND USAGE

ERLEADA is indicated for the treatment of patients with non-metastatic, castration-resistant prostate cancer (NM-CRPC).

2 DOSAGE AND ADMINISTRATION

2.1 Recommended Dosage

The recommended dose of ERLEADA is 240 mg (four 60 mg tablets) administered orally once daily. Swallow the tablets whole. ERLEADA can be taken with or without food.

Patients should also receive a gonadotropin-releasing hormone (GnRH) analog concurrently or should have had a bilateral orchiectomy.

2.2 Dose Modification

If a patient experiences a greater than or equal to Grade 3 toxicity or an intolerable side effect, hold dosing until symptoms improve to less than or equal to Grade 1 or original grade, then resume at the same dose or a reduced dose (180 mg or 120 mg), if warranted.

3 DOSAGE FORMS AND STRENGTHS

Tablets (60 mg): slightly yellowish to greyish green oblong film-coated tablets, debossed with "AR 60" on one side.

4 CONTRAINDICATIONS

Pregnancy

ERLEADA can cause fetal harm and potential loss of pregnancy *[see Use in Specific Populations (8.1)]*.

5 WARNINGS AND PRECAUTIONS

5.1 Falls and Fractures

Falls and fractures occurred in patients receiving ERLEADA. Evaluate patients for fracture and fall risk. Monitor and manage patients at risk for fractures according to established treatment guidelines and consider use of bone targeted agents.

In a randomized study (SPARTAN), falls occurred in 16% of patients treated with ERLEADA compared to 9% of patients treated with placebo. Falls were not associated with loss of consciousness or seizure. Fractures occurred in 12% of patients treated with ERLEADA and in 7% of patients treated with placebo. Grade 3-4 fractures occurred in 3% of patients treated with ERLEADA and in 1% of patients treated with placebo. The median time to onset of fracture was 314 days (range: 20 to 953 days) for patients treated with ERLEADA. Routine bone density assessment and treatment of osteoporosis with bone targeted agents were not performed in the SPARTAN study.

5.2 Seizure

Seizure occurred in patients receiving ERLEADA. Permanently discontinue ERLEADA in patients who develop a seizure during treatment. It is unknown whether anti-epileptic medications will prevent seizures with ERLEADA. Advise patients of the risk of developing a seizure while receiving ERLEADA and of engaging in any activity where sudden loss of consciousness could cause harm to themselves or others.

In a randomized study (SPARTAN), two patients (0.2%) treated with ERLEADA experienced a seizure. Seizure occurred from 354 to 475 days after initiation of ERLEADA. No seizures occurred in patients treated with placebo. Patients with a history of seizure, predisposing factors for seizure, or receiving drugs known to decrease the seizure threshold or to induce seizure were excluded. There is no clinical experience in re-administering ERLEADA to patients who experienced a seizure.

6 ADVERSE REACTIONS

The following are discussed in more detail in other sections of the labeling:

- Falls and Fractures *[see Warnings and Precautions (5.1)]*.

- Seizure *[see Warnings and Precautions (5.2)]*.

6.1 Clinical Trial Experience

Because clinical trials are conducted under widely varying conditions, adverse reaction rates observed in the clinical trials of a drug cannot be directly compared to rates in the clinical trials of another drug and may not reflect the rates observed in practice.

SPARTAN, a randomized (2:1), double-blind, placebo-controlled, multi-center clinical study, enrolled patients who had non-metastatic, castration-resistant prostate cancer (NM-CRPC). In this study, patients received either ERLEADA at a dose of 240 mg daily or a placebo. All patients in the SPARTAN study received a concomitant gonadotropin-releasing hormone (GnRH) analog or had a bilateral orchiectomy. The median duration of exposure was 16.9 months (range: 0.1 to 42 months) in patients who received ERLEADA and 11.2 months (range: 0.1 to 37 months) in patients who received placebo.

Overall, 8 patients (1%) who were treated with ERLEADA died from adverse reactions. The reasons for death were infection (n=4), myocardial infarction (n=3), and cerebral hemorrhage (n=1). One patient (0.3%) treated with placebo died from an adverse reaction of cardiopulmonary arrest (n=1). ERLEADA was discontinued due to adverse reactions in 11% of patients, most commonly from rash (3%). Adverse reactions leading to dose interruption or reduction of ERLEADA occurred in 33% of patients; the most common (>1%) were rash, diarrhea, fatigue, nausea, vomiting, hypertension, and hematuria. Serious adverse reactions occurred in 25% of ERLEADA-treated patients and 23% in patients receiving placebo. The most common serious adverse reactions (>2%) were fracture (3%) in the ERLEADA arm and urinary retention (4%) in the placebo arm.

Table 1 shows adverse reactions occurring in >10% on the ERLEADA arm in SPARTAN that occurred with a 2% absolute increase in frequency compared to placebo. Table 2 shows laboratory abnormalities that occurred in >15% of patients, and more frequently (>5%) in the ERLEADA arm compared to placebo.

Table 2: Adverse Reactions in SPARAN

| System/Organ Class<br>Adverse reaction | EURLEADA<br>N=803 | | Placebo<br>N=398 | |
|---|---|---|---|---|
| | All Grades % | Grade 3-4 % | All Grades % | Grade 3-4 % |
| General disorders and administration site conditions | | | | |
| Fatigue[1,4] | 39 | 1 | 28 | 0.3 |
| Musculoskeletal and connective tissue disorders | | | | |
| Arthralgia[4] | 16 | 0 | 8 | 0 |
| Skin and subcutaneous tissue disorders | | | | |
| Rash[2] | 24 | 5 | 6 | 0.3 |
| Metabolism and nutrition disorders | | | | |
| Decreased appetite[5] | 12 | 0.1 | 9 | 0 |
| Peripheral edema[6] | 11 | 0 | 9 | 0 |
| Injury, poisoning and procedural complications | | | | |
| Fall[4] | 16 | 2 | 9 | 0.8 |
| Fracture[3] | 12 | 3 | 7 | 0.8 |
| Investigations | | | | |
| Weight decreased[4] | 16 | 1 | 6 | 0.3 |
| Endocrine disorders | | | | |
| Hypertension | 25 | 14 | 20 | 12 |
| Hot flush | 14 | 0 | 9 | 0 |
| Gastrointestinal disorders | | | | |
| Diarrhea | 20 | 1 | 15 | 0.5 |
| Nausea | 18 | 0 | 16 | 0 |

[1] Includes fatigue and asthenia

[2] Includes rash, rash maculo-papular, rash generalized, urticaria, rash pruritic, rash macular, conjunctivitis, erythema multiforme, rash papular, skin exfoliation, genital rash, rash erythematous, stomatitis, drug eruption, mouth ulceration, rash pustular, blister, papule, pemphigoid, skin erosion, and rash vesicular

[3] Includes rib fracture, lumbar vertebral fracture, spinal compression fracture, spinal fracture, foot fracture, hip fracture, humerus fracture, thoracic vertebral fracture, upper limb fracture, fractured sacrum, hand fracture, pubis fracture, acetabulum fracture, ankle fracture, compression fracture, costal cartilage fracture, facial bones fracture, lower limb fracture, osteoporotic fracture, wrist fracture, avulsion fracture, fibula fracture, fractured coccyx, pelvic fracture, radius fracture, sternal fracture, stress fracture, traumatic fracture, cervical vertebral fracture, femoral neck fracture, and tibia fracture

[4] Grade 4 definitions do not exist for these reactions

[5] Includes appetite disorder, decreased appetite, early satiety, and hypophagia

[6] Includes peripheral edema, generalized edema, edema, edema genital, penile edema, peripheral swelling, scrotal edema, lymphedema, swelling, and localized edema Additional clinically significant adverse reactions occurring in 2% or more of patients treated with ERLEADA included hypothyroidism (8.1% versus 2% on placebo), pruritus (6.2% versus 2% on placebo), ischemic heart disease (3.7% versus 2% on placebo), and heart failure (2.2% versus 1% on placebo).

Table 2: Laboratory Abnormalities Occurring in ≥ 15% of ERLEADA-Treated Patients and at a Higher Incidence than Placebo (Between Arm Difference > 5% All Grades) in SPARTAN

| Laboratory Abnormality | EURLEADA N=803 | | Placebo N=398 | |
|---|---|---|---|---|
| | All Grades % | Grade 3-4 % | All Grades % | Grade 3-4 % |
| Hematology | | | | |
| Anemia | 70 | 0.4 | 64 | 0.5 |
| Leukopenia | | | | |
| Lymphopenia | | | | |
| Chemistry | | | | |
| Hypercholesterolemia[1] | | | | |
| Hyperglycemia[1] | | | | |
| Hypertriglyceridemia[1] | | | | |
| Hyperkalemia | | | | |

[1] Does not reflect fasting values

Rash

In SPARTAN, rash associated with ERLEADA was most commonly described as macular or maculo-papular. Adverse reactions of rash were reported for 24% of patients treated with ERLEADA versus 6% of patients treated with placebo. Grade 3 rashes (defined as covering > 30% body surface area [BSA]) were reported with ERLEADA treatment (5%) versus placebo (0.3%).

The onset of rash occurred at a median of 82 days of ERLEADA treatment. Rash resolved in 81% of patients within a median of 60 days (range: 2 to 709 days) from onset of rash. Four (4%) of patients treated with ERLEADA received systemic corticosteroids for treatment of rash. Rash recurred in approximately half of patients who were re-challenged with ERLEADA.

Hypothyroidism

Hypothyroidism was reported for 8% of patients treated with ERLEADA and 2% of patients treated with placebo based on assessments of thyroid-stimulating hormone (TSH) every 4 months.

Elevated TSH occurred in 25% of patients treated with ERLEADA and 7% of patients treated with placebo. The median onset was Day 113. There were no Grade 3 or 4 adverse reactions. Thyroid replacement therapy was initiated in 7% of patients treated with ERLEADA. Thyroid replacement therapy, when clinically indicated, should be initiated or dose-adjusted *[see Drug Interactions (7.2)]*.

7 DRUG INTERACTIONS

7.1 *Effect of Other Drugs on ERLEADA*

Strong CYP2C8 or CYP3A4 Inhibitors

Co-administration of a strong CYP2C8 or CYP3A4 inhibitor is predicted to increase the steady-state exposure of the active moieties (sum of unbound apalutamide plus the potency-adjusted unbound N-desmethyl-apalutamide). No initial dose adjustment is necessary however, reduce the ERLEADA dose based on tolerability *[see Dosage and Administration (2.2)]*. Mild or moderate inhibitors of CYP2C8 or CYP3A4 are not expected to affect the exposure of apalutamide.

7.2 *Effect of ERLEADA on Other Drugs*

CYP3A4, CYP2C9, CYP2C19 and UGT Substrates

ERLEADA is a strong inducer of CYP3A4 and CYP2C19, and a weak inducer of CYP2C9 in humans. Concomitant use of ERLEADA with medications that are primarily metabolized by CYP3A4, CYP2C19, or CYP2C9 can result in lower exposure to these medications. Substitution for these medications is recommended when possible or evaluate for loss of activity if medication is continued. Concomitant administration of ERLEADA with medications that are substrates of UDP-glucuronosyl transferase (UGT) can result in decreased exposure. Use caution if substrates of UGT must be co-administered with ERLEADA and evaluate for loss of activity *[see Clinical Pharmacology (12.3)]*.

P-gp, BCRP or OATP1B1 Substrates

Apalutamide was shown to be a weak inducer of P-glycoprotein (P-gp), breast cancer resistance protein (BCRP), and organic anion transporting polypeptide 1B1 (OATP1B1) clinically. At steady-state, apalutamide reduced the plasma exposure to fexofenadine (a P-gp substrate) and rosuvastatin (a BCRP/OATP1B1 substrate). Concomitant use of ERLEADA with medications that are substrates of P-gp, BCRP, or OATP1B1 can result in lower exposure of these medications. Use caution if substrates of P-gp, BCRP or OATP1B1 must be co-administered with ERLEADA and evaluate for loss of activity if medication is continued *[see Clinical Pharmacology (12.3)]*.

8 USE IN SPECIFIC POPULATIONS

8.1 *Pregnancy*

Risk Summary

ERLEADA is contraindicated for use in pregnant women because the drug can cause fetal harm and potential loss of pregnancy. ERLEADA is not indicated for use in females, so animal embryo-fetal developmental toxicology studies were not conducted with apalutamide. There are no human data on the use of ERLEADA in pregnant women. Based on its mechanism of action, ERLEADA may cause fetal harm when administered during pregnancy.

8.2 Lactation

Risk Summary

ERLEADA is not indicated for use in females. There are no data on the presence of apalutamide or its metabolites in human milk, the effect on the breastfed child, or the effect on milk production.

8.3 Females and Males of Reproductive Potential

Contraception

Males

Based on the mechanism of action and findings in an animal reproduction study, advise male patients with female partners of reproductive potential to use effective contraception during treatment and for 3 months after the last dose of ERLEADA. *[see Use in Specific Populations (8.1)]*.

Infertility

Males

Based on animal studies, ERLEADA may impair fertility in males of reproductive potential *[see Nonclinical Toxicology (13.1)]*.

8.4 Pediatric Use

Safety and effectiveness of ERLEADA in pediatric patients have not been established.

8.5 Geriatric Use

Of the 803 patients who received ERLEADA in SPARTAN, 87% of patients were 65 years and over and 49% were 75 years and over. Grade 3-4 adverse reactions occurred in 46% (323/697) of patients 65 years or older and in 51% (197/391) of patients 75 years or older treated with ERLEADA compared to 35% (124/355) of patients 65 years or older and 37% (70/187) of patients 75 years or older treated with placebo. No overall differences in effectiveness were observed between these patients and younger patients.

10 OVERDOSAGE

There is no known specific antidote for apalutamide overdose. In the event of an overdose, stop ERLEADA, undertake general supportive measures until clinical toxicity has been diminished or resolved.

11 DESCRIPTION

Apalutamide, the active ingredient of ERLEADA, is an androgen receptor inhibitor. The Chemical name is (4-[7-(6-Cyano-5-trifluoromethylpyridin-3-yl)-8-oxo-6-thioxo- 5,7-diazaspiro[3.4]oct-5-yl]-2-fluoro-N-methylbenzamide). Apalutamide is a white to slightly yellow powder. Apalutamide is practically insoluble in aqueous media over a wide range of pH values.

The molecular weight is 477.44 and molecular formula is $C_{21}H_{15}F_4N_5O_2S$. The structural formula is:

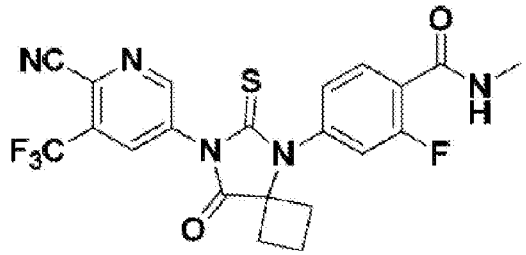

ERLEADA (apalutamide) is supplied as film-coated tablets for oral administration containing 60 mg of apalutamide. Inactive ingredients of the core tablet are: colloidal anhydrous silica, croscarmellose sodium, hydroxypropyl methylcellulose-acetate succinate, magnesium stearate, microcrystalline cellulose, and silicified microcrystalline cellulose.

The tablets are finished with a commercially available film-coating comprising the following excipients: iron oxide black, iron oxide yellow, polyethylene glycol, polyvinyl alcohol, talc, and titanium dioxide.

12  CLINICAL PHARMACOLOGY

12.1  Mechanism of Action

Apalutamide is an Androgen Receptor (AR) inhibitor that binds directly to the ligand-binding domain of the AR. Apalutamide inhibits AR nuclear translocation, inhibits DNA binding, and impedes AR-mediated transcription. A major metabolite, N-desmethyl apalutamide, is a less potent inhibitor of AR, and exhibited one-third the activity of apalutamide in an in vitro transcriptional reporter assay. Apalutamide administration caused decreased tumor cell proliferation and increased apoptosis leading to decreased tumor volume in mouse xenograft models of prostate cancer.

12.2  Pharmacodynamics

Cardiac Electrophysiology

The effect of apalutamide 240 mg once daily on the QTc interval was assessed in an open-label, uncontrolled, multi-center, single-arm dedicated QT study in 45 patients with CRPC. The maximum mean QTcF change from baseline was 12.4 ms (2-sided 90% upper CI: 16.0 ms). An exposure-QT analysis suggested a concentration-dependent increase in QTcF for apalutamide and its active metabolite.

12.3  Pharmacokinetics

Apalutamide pharmacokinetic parameters are presented as the mean [standard deviation (SD)] unless otherwise specified. Apalutamide $C_{max}$ and area under the concentration curve (AUC) increased proportionally following repeated once-daily dosing of 30 to 480 mg (0.125 to 2 times the recommended dosage). Following administration of the recommended dosage, apalutamide steady-state was achieved after 4 weeks and the mean accumulation ratio was approximately 5-fold. Apalutamide $C_{max}$ was 6.0 mcg/mL (1.7) and AUC was 100 mcg·h/mL (32) at steady-state. Daily fluctuations in apalutamide plasma concentrations were low, with mean peak-to-trough ratio of 1.63. An increase in apparent clearance (CL/F) was observed with repeat dosing, likely due to induction of apalutamide's own metabolism. The auto-induction effect likely reached its maximum at the recommended dosage because exposure of apalutamide across the dose range of 30 to 480 mg is dose-proportional.

The major active metabolite N-desmethyl apalutamide $C_{max}$ was 5.9 mcg/mL (1.0) and AUC was 124 mcg·h/mL (23) at steady-state after the recommended dosage. N-desmethyl apalutamide was characterized by a flat concentration-time profile at steady-state with a mean peak-to-trough ratio of 1.27. Mean AUC metabolite/parent drug ratio for N-desmethyl apalutamide following repeat-dose administration was 1.3. Based on systemic exposure, relative potency, and pharmacokinetic properties, N-desmethyl apalutamide likely contributed to the clinical activity of apalutamide.

Absorption

Mean absolute oral bioavailability was approximately 100%. Median time to achieve peak plasma concentration ($t_{max}$) was 2 hours (range: 1 to 5 hours).

Effect of Food

Administration of apalutamide to healthy subjects under fasting conditions and with a high-fat meal (approximately 500 to 600 fat calories, 250 carbohydrate calories, and 150 protein calories) resulted in no clinically relevant changes in $C_{max}$ and AUC. Median time to reach $t_{max}$ was delayed approximately 2 hours with food.

Distribution

The mean apparent volume of distribution at steady-state of apalutamide was approximately 276 L.

Apalutamide was 96% and N-desmethyl apalutamide was 95% bound to plasma proteins with no concentration dependency.

Elimination

The CL/F of apalutamide was 1.3 L/h after single dosing and increased to 2.0 L/h at steady-state after once-daily dosing likely due to CYP3A4 auto-induction. The mean effective half-life for apalutamide in patients was approximately 3 days at steady-state.

Metabolism

Metabolism is the main route of elimination of apalutamide. Apalutamide is primarily metabolized by CYP2C8 and CYP3A4 to form active metabolite, N-desmethyl apalutamide. The contribution of CYP2C8 and CYP3A4 in the metabolism of apalutamide is estimated to be 58% and 13% following single dose but changes to 40% and 37%, respectively at steady-state.

Apalutamide represented 45% and N-desmethyl apalutamide represented 44% of the total AUC following a single oral administration of radiolabeled apalutamide 240 mg.

Excretion

Up to 70 days following a single oral administration of radiolabeled apalutamide, 65% of the dose was recovered in urine (1.2% of dose as unchanged apalutamide and 2.7% as N-desmethyl apalutamide) and 24% was recovered in feces (1.5% of dose as unchanged apalutamide and 2% as N-desmethyl apalutamide).

Specific Populations

No clinically significant differences in the pharmacokinetics of apalutamide or N-desmethyl apalutamide were observed based on age (18-94 years), race (Black, non-Japanese Asian, Japanese), mild to moderate (eGFR 30-89 mL/min/1.73m$^2$, estimated by the modification of diet in renal disease [MDRD] equation) renal impairment, or mild (Child-Pugh A) to moderate (Child-Pugh B) hepatic impairment.

The effect of severe renal impairment or end stage renal disease (eGFR $\leq$29 mL/min/1.73m$^2$, MDRD) or severe hepatic impairment (Child-Pugh C) on apalutamide pharmacokinetics is unknown.

Drug Interactions

Effect of Other Drugs on ERLEADA

Strong CYP2C8 inhibitors

Apalutamide $C_{max}$ decreased by 21% while AUC increased by 68% following co-administration of ERLEADA as a 240 mg single dose with gemfibrozil (a strong CYP2C8 inhibitor). Gemfibrozil is predicted to increase the steady-state apalutamide $C_{max}$ by 32% and AUC by 44%. For the active moieties (sum of unbound apalutamide plus the potency-adjusted unbound N-desmethyl apalutamide), the predicted steady-state $C_{max}$ increased by 19% and AUC by 23%.

Strong CYP3A4 inhibitors

Apalutamide $C_{max}$ decreased by 22% while AUC was similar following co-administration of ERLEADA as a 240 mg single dose with itraconazole (a strong CYP3A4 inhibitor). Ketoconazole (a strong CYP3A4 inhibitor) is predicted to increase the single-dose apalutamide AUC by 24% but have no impact on $C_{max}$. Ketoconazole is predicted to increase the steady-state apalutamide $C_{max}$ by 38% and AUC by 51%. For the active moieties, the predicted steady-state $C_{max}$ increased by 23% and AUC by 28%.

CYP3A4/CYP2C8 inducers

Rifampin (a strong CYP3A4 and moderate CYP2C8 inducer) is predicted to decrease the steady-state apalutamide $C_{max}$ by 25% and AUC by 34%. For the active moieties, the predicted steady-state $C_{max}$ decreased by 15% and AUC by 19%.

*Acid lowering agents*

Apalutamide is not ionizable under relevant physiological pH condition, therefore acid lowering agents (e.g. proton pump inhibitor, $H_2$-receptor antagonist, antacid) are not expected to affect the solubility and bioavailability of apalutamide.

*Drugs affecting transporters*

In vitro, apalutamide and N-desmethyl apalutamide are substrates for P-gp but not BCRP, OATP1B1, and OATP1B3. Because apalutamide is completely absorbed after oral administration, P-gp does not limit the absorption of apalutamide and therefore, inhibition or induction of P-gp is not expected to affect the bioavailability of apalutamide.

Effect of ERLEADA on Other Drugs

CYP substrates

In vitro studies showed that apalutamide and N-desmethyl apalutamide are moderate to strong CYP3A4 and CYP2B6 inducers, are moderate inhibitors of CYP2B6 and CYP2C8, and weak inhibitors of CYP2C9, CYP2C19, and CYP3A4. Apalutamide and N-desmethyl apalutamide do not affect CYP1A2 and CYP2D6 at therapeutically relevant concentrations.

Co-administration of ERLEADA with single oral doses of sensitive CYP substrates resulted in a 92% decrease in the AUC of midazolam (a CYP3A4 substrate), 85% decrease in the AUC of omeprazole (a CYP2C19 substrate), and 46% decrease in the AUC of S-warfarin (a CYP2C9 substrate). ERLEADA did not cause clinically significant changes in exposure to a CYP2C8 substrate.

*P-gp, BCRP and OATP1B1 substrates*

Co-administration of ERLEADA with single oral doses of transporter substrates resulted in a 30% decrease in the AUC of fexofenadine (a P-gp substrate) and 41% decrease in the AUC of rosuvastatin (a BCRP/OATP1B1 substrate) but had no impact on $C_{max}$.

*UGT substrates*

Apalutamide may induce UGT. Concomitant administration of ERLEADA with medications that are substrates of UGT may result in lower exposure to these medications.

*OCT2, OAT1, OAT3 and MATEs substrates*

In vitro, apalutamide and N-desmethyl apalutamide inhibit organic cation transporter 2 (OCT2), organic anion transporter 3 (OAT3) and multidrug and toxin extrusions (MATEs), and do not inhibit organic anion transporter 1. Apalutamide is not predicted to cause clinically significant changes in exposure to an OAT3 substrate.

13 NONCLINICAL TOXICOLOGY

13.1 *Carcinogenesis, Mutagenesis, Impairment of Fertility*

Long-term animal studies have not been conducted to evaluate the carcinogenic potential of apalutamide. Apalutamide did not induce mutations in the bacterial reverse mutation (Ames) assay and was not genotoxic in either in vitro chromosome aberration assay or the in vivo rat bone marrow micronucleus assay or the in vivo rat Comet assay.

In repeat-dose toxicity studies in male rats (up to 26 weeks) and dogs (up to 39 weeks), atrophy of the prostate gland and seminal vesicles, aspermia/hypospermia, tubular degeneration and/or hyperplasia or hypertrophy of the interstitial cells in the reproductive system were observed at > 25 mg/kg/day in rats (1.4 times the human exposure based on AUC) and > 2.5 mg/kg/day in dogs (0.9 times the human exposure based on AUC).

In a fertility study in male rats, a decrease in sperm concentration and motility, increased abnormal sperm morphology, lower copulation and fertility rates (upon pairing with untreated females) along with reduced weights of the secondary sex glands and epididymis were observed following 4 weeks of dosing at > 25 mg/kg/day (0.8 times the human exposure based on AUC). A reduced number of live fetuses due to increased pre- and/or post-implantation loss was observed following 4 weeks of 150 mg/kg/day administration (5.7 times the human exposure based on AUC). Effects on male rats were reversible after 8 weeks from the last apalutamide administration.

14 CLINICAL STUDIES

SPARTAN (NCT01946204) was a multicenter, double-blind, randomized (2:1), placebo-controlled clinical trial in which 1207 patients with NM-CRPC were randomized (2:1) to receive either ERLEADA orally at a dose of 240 mg once daily (N = 806) or placebo once daily (N = 401). All patients in the SPARTAN trial received a concomitant gonadotropin-releasing hormone (GnRH) analog or had a bilateral orchiectomy. Patients were stratified by Prostate Specific Antigen (PSA) Doubling Time (PSADT), the use of bone-sparing agents, and locoregional disease. Patients were required to have a PSADT ≤ 10 months and confirmation of non-metastatic disease by blinded independent central review (BICR). PSA results were blinded and were not used for treatment discontinuation. Patients randomized to either arm discontinued treatment for radiographic disease progression confirmed by BICR, locoregional-only progression, initiation of new treatment, unacceptable toxicity, or withdrawal.

The following patient demographics and baseline disease characteristics were balanced between the treatment arms. The median age was 74 years (range 48-97) and 26% of patients were 80 years of age or older. The racial distribution was 66% Caucasian, 12% Asian, and 6% Black. Seventy-seven percent (77%) of patients in both treatment arms had prior surgery or radiotherapy of the prostate. A majority of patients had a Gleason score of 7 or higher (78%). Fifteen percent (15%) of patients had <2 cm pelvic lymph nodes at study entry. Seventy-three percent (73%) of patients received prior treatment with an anti-androgen; 69% of patients received bicalutamide and 10% of patients received flutamide. All patients had an Eastern Cooperative Oncology Group Performance Status (ECOG PS) score of 0 or 1 at study entry. Among the patients who discontinued study treatment (N = 279 for placebo and N = 314 for ERLEADA), a greater proportion (80%) of patients treated with placebo received subsequent therapy compared to patients treated with ERLEADA (56%). Locoregional-only progression occurred in 2% of patients overall.

The major efficacy outcome measure of the study was metastasis-free survival (MFS), defined as the time from randomization to the time of first evidence of BICR-confirmed distant metastasis, defined as new bone or soft tissue lesions or enlarged lymph nodes above the iliac bifurcation, or death due to any cause, whichever occurred first. Additional efficacy endpoints were time to metastasis (TTM), progression-free survival (PFS) which also includes locoregional progression, time to symptomatic progression, and overall survival (OS).

A statistically significant improvement in MFS was demonstrated in patients randomized to receive ERLEADA compared with patients randomized to receive placebo. Consistent results were observed across patient subgroups including PSADT ($\leq$ 6 months or > 6 months), use of a prior bone-sparing agent (yes or no), and locoregional disease (N0 or N1). The major efficacy outcome was supported by statistically significant improvements in TTM, PFS, and time to symptomatic progression. Overall survival (OS) data were not mature at the time of final MFS analysis (24% of the required number of events). The efficacy results of MFS, TTM, and PFS from SPARTAN are summarized in Figure 3 and Table 3.

Table 3: BICR-assessed Efficacy Results (SPARTAN)

| Endpoint | Number of Events (%) | | Median [Months (95% CI)] | | HR (95% CI) p-value (log-rank test)[1] |
|---|---|---|---|---|---|
| | ERLEADA (N=806) | Placebo (N=401) | ERLEADA | Placebo | |
| Metastasis Free Survival | 184 (23%) | 194 (48%) | 40.51 (NE, NE) | 16.20 (14.59, 18.40) | 0.28 (0.23, 0.35) <0.0001 |
| Time to Metastasis | 175 (22%) | 191 (48%) | 40.51 (NE, NE) | 16.59 (14.59, 18.46) | 0.27 (0.22, 0.34) <0.0001 |
| Progression-Free Survival | 200 (25%) | 204 (51%) | 40.51 (NE, NE) | 14.72 (14.49, 18.37) | 0.29 (0.24, 0.36) <0.0001 |

[1] All analyses stratified by PSA doubling time, bone-sparing agent use, and locoregional disease status.
NE=Not Estimable

16  HOW SUPPLIED/STORAGE AND HANDLING

ERLEADA (apalutamide) 60 mg film-coated tablets are slightly yellowish to greyish green, oblong-shaped tablets debossed with "AR 60" on one side. ERLEADA 60 mg tablets are available in bottles of 120 tablets. Each bottle contains silica gel desiccant.

NDC Number       59676-600-12

Storage and Handling

Store at 20°C to 25°C (68°F to 77°F); excursions permitted to 15°C to 30°C (59°F to 86°F) *[see USP Controlled Room Temperature]*.

Store in the original package. Do not discard desiccant. Protect from light and moisture.

17  PATIENT COUNSELING INFORMATION

*Advise the patient to read the FDA-approved patient labeling (Patient Information).*

Falls and Fractures

- Inform patients that ERLEADA is associated with an increased incidence of falls and fractures *[see Warnings and Precautions (5.1)]*.

Seizures

- Inform patients that ERLEADA has been associated with an increased risk of seizure. Discuss conditions that may predispose to seizures and medications that may lower the seizure threshold. Advise patients of the risk of engaging in any activity where sudden loss of consciousness could cause serious harm to themselves or others. Inform patients to contact their healthcare provider right away if they experience a seizure *[see Warnings and Precautions (5.2)]*.

Rash

- Inform patients that ERLEADA is associated with rashes and to inform their healthcare provider if they develop a rash *[see Adverse Reactions (6.1)]*.

Dosage and Administration

- Inform patients receiving concomitant gonadotropin-releasing hormone (GnRH) analog therapy that they need to maintain this treatment during the course of treatment with ERLEADA.

- Instruct patients to take their dose at the same time each day (once daily). ERLEADA can be taken with or without food. Each tablet should be swallowed whole.

- Inform patients that in the event of a missed daily dose of ERLEADA, they should take their normal dose as soon as possible on the same day with a return to the normal schedule on the following day. The patient should not take extra tablets to make up the missed dose *[see Dosage and Administration (2.1)]*.

Embryo-Fetal Toxicity

- Inform patients that ERLEADA can be harmful to a developing fetus. Advise patients having sex with female partners of reproductive potential to use effective contraception during treatment and for 3 months after the last dose of ERLEADA. Advise male patients to use a condom if having sex with a pregnant woman *[see Use in Specific Populations (8.1, 8.3)]*.

Infertility

- Advise male patients that ERLEADA may impair fertility and not to donate sperm during therapy and for 3 months following the last dose of ERLEADA *[see Use in Specific Populations (8.3)]*.

Manufactured by:
Janssen Ortho LLC
Gurabo, PR 00778

Manufactured for:
Janssen Products, LP
Horsham, PA 19044

© 2018 Janssen Pharmaceutical Companies

| |
|---|
| PATIENT INFORMATION<br>ERLEADA™ (er lee'dah)<br>(apalutamide)<br>Tablets |
| What is ERLEADA?<br>ERLEADA is a prescription medicine used to treat prostate cancer that has not spread to other parts of the body and no longer responds to a medical or surgical treatment that lowers testosterone.<br>It is not known if ERLEADA is safe or effective in children. |
| Do not take ERLEADA if you:<br>• are pregnant or may become pregnant. ERLEADA may harm your unborn baby.<br>• are female. ERLEADA is not for use in women. |
| Before taking ERLEADA, tell your healthcare provider about all your medical conditions, including if you:<br>• have a history of seizures, brain injury, stroke, or brain tumors<br>• have a partner who is pregnant or may become pregnant. Men who are sexually active with a pregnant woman must use a condom during and for 3 months after treatment with ERLEADA. If your sexual partner may become pregnant, an effective birth control (contraception) must be used during and for 3 months after treatment. Talk with your healthcare provider if you have questions about birth control.<br>Tell your healthcare provider about all the medicines you take, including prescription and over-the-counter medicines, vitamins, and herbal supplements. ERLEADA can interact with many other medicines.<br>You should not start or stop any medicine before you talk with the healthcare provider that prescribed ERLEADA.<br>Know the medicines you take. Keep a list of them with you to show to your healthcare provider and pharmacist when you get a new medicine. |
| How should I take ERLEADA?<br>• Take ERLEADA exactly as your healthcare provider tells you.<br>• Take your prescribed dose of ERLEADA 1 time a day, at the same time each day.<br>• Take ERLEADA with or without food.<br>• Swallow ERLEADA tablets whole.<br>• Your healthcare provider may change your dose if needed.<br>• Do not stop taking your prescribed dose of ERLEADA without talking with your healthcare provider first.<br>• If you miss a dose of ERLEADA, take your normal dose as soon as possible on the same day. Return to your normal schedule on the following day. You should not take extra tablets to make up the missed dose.<br>• You should start or continue a gonadotropin-releasing hormone (GnRH) analog therapy during your treatment with ERLEADA unless you had a surgery to lower the amount of testosterone in your body (surgical castration).<br>• If you take too much ERLEADA, call your healthcare provider or go to the nearest hospital emergency room.<br>• Your healthcare provider may do blood tests to check for side effects. |

What are the possible side effects of ERLEADA?
ERLEADA may cause serious side effects including:
- Falls and fractures. ERLEADA treatment can cause bones and muscles to weaken and may increase your risk for falls and fractures. Falls and fractures have happened in people during treatment with ERLEADA. Falls were not caused by loss of consciousness (fainting) or seizures. Your healthcare provider will monitor your risks for falls and fractures during treatment with ERLEADA.
- Seizure. If you take ERLEADA, you may be at risk of having a seizure. You should avoid activities where a sudden loss of consciousness could cause serious harm to yourself or others. Tell your healthcare provider right away if you have a loss of consciousness or seizure. Your healthcare provider will stop ERLEADA if you have a seizure during treatment.

The most common side effects of ERLEADA include:
- feeling very tired
- high blood pressure
- rash
- diarrhea
- nausea
- decreased appetite
- weight loss
- joint pain
- fall
- hot flash
- bone injury (fracture)
- swollen hands, ankles, or feet ERLEADA may cause fertility problems in males, which may affect the ability to father children. Talk to your healthcare provider if you have concerns about fertility. Do not donate sperm during treatment with ERLEADA and for 3 months after the last dose of ERLEADA.

Tell your healthcare provider if you have any side effect that bothers you or that does not go away.
These are not all the possible side effects of ERLEADA.
Call your doctor for medical advice about side effects. You may report side effects to FDA at 1-800-FDA-1088.

How should I store ERLEADA?
- Store ERLEADA at room temperature between 68°F to 77°F (20°C to 25°C).
- Store ERLEADA in the original package.
- The bottle of ERLEADA contains a desiccant packet to help keep your medicine dry (protect it from moisture). Do not throw away (discard) the desiccant.
- Protect ERLEADA from light and moisture.

Keep ERLEADA and all medicines out of the reach of children.

General information about the safe and effective use of ERLEADA.
Medicines are sometimes prescribed for purposes other than those listed in a Patient Information leaflet. Do not use ERLEADA for a condition for which it was not prescribed. Do not give ERLEADA to other people, even if they have the same symptoms that you have. It may harm them.
If you would like more information, talk with your healthcare provider. You can ask your healthcare provider or pharmacist for information about ERLEADA that is written for health professionals.

What are the ingredients in ERLEADA?
Active ingredient:
apalutamide

Inactive ingredients:
colloidal anhydrous silica, croscarmellose sodium, hydroxypropyl methylcellulose-acetate succinate, magnesium stearate, microcrystalline cellulose, and silicified microcrystalline cellulose. The film-coating contains iron oxide black, iron oxide yellow, polyethylene glycol, polyvinyl alcohol, talc, and titanium dioxide.

Manufactured by: Janssen Ortho LLC, Gurabo, PR 00778
Manufactured for: Janssen Products, LP, Horsham, PA 19044
© 2018 Janssen Pharmaceutical Companies
For more information, call Janssen Products, LP at 1-800-526-7736 (1-800-JANSSEN) or go to www.erleada.com.

This Patient Information has been approved by the U.S. Food and Drug Administration.
Issued: February/2018

The examples and embodiments described herein are for illustrative purposes only and various modifications or changes suggested to persons skilled in the art are to be included within the spirit and purview of this application and scope of the appended claims

What is claimed is:

1. A method of improving metastasis free survival in a male human with non-metastatic castration-resistant prostate cancer, said method comprising administering to said male human an approved drug product comprising enzalutamide in combination with androgen deprivation therapy.

2. The method of claim 1, wherein the androgen deprivation therapy consists of orchiectomy or gonadotropin-releasing hormone agonists or antagonists.

3. The method of claim 1, wherein the approved drug product provides an increase in the metastasis-free survival of the male human relative to the mean survival rate of a population of male humans with non-metastatic castration-resistant prostate cancer, said population having been administered a placebo in combination with androgen deprivation therapy.

4. The method of claim 1, wherein a drug product label for a reference listed drug for such approved drug product comprises metastasis free survival data.

5. The method of claim 1, wherein a drug product label for a reference listed drug for such approved drug product includes instructions for treating non-metastatic castration resistant prostate cancer.

6. The method of claim 1, further comprising selling such approved drug product, wherein a drug product label for a reference listed drug for such approved drug product includes instructions for treating non-metastatic castration resistant prostate cancer.

7. The method of claim 6, wherein the drug product label comprises metastasis free survival data.

8. A method of improving metastasis free survival in a male human with nonmetastatic castration-resistant prostate cancer, said method comprising providing to said male human an approved drug product comprising enzalutamide in combination with androgen deprivation therapy, wherein the androgen deprivation therapy consists of orchiectomy or gonadotropin-releasing hormone agonists or antagonists.

9. The method of claim 8, wherein a drug product label for a reference listed drug for such approved drug product comprises metastasis free survival data.

10. The method of claim 8, wherein a drug product label for a reference listed drug for such approved drug product includes instructions for treating non-metastatic castration resistant prostate cancer.

* * * * *

UNITED STATES PATENT AND TRADEMARK OFFICE
CERTIFICATE OF CORRECTION

| | |
|---|---|
| PATENT NO. | : 11,491,149 B2 |
| APPLICATION NO. | : 16/885767 |
| DATED | : November 8, 2022 |
| INVENTOR(S) | : Arturo Molina et al. |

It is certified that error appears in the above-identified patent and that said Letters Patent is hereby corrected as shown below:

On the Title Page

Under item (12) "Molina" should read --Molina et al.--

Item (72) Inventors:
Add inventor - Margaret Yu, Los Angeles, CA (US)

Signed and Sealed this
Twenty-seventh Day of June, 2023

Katherine Kelly Vidal
*Director of the United States Patent and Trademark Office*